United States Patent
Hausheer (12)

(10) Patent No.: US 11,471,431 B2
(45) Date of Patent: *Oct. 18, 2022

(54) INCREASING CANCER PATIENT SURVIVAL TIME BY ADMINISTRATION OF DITHIO-CONTAINING COMPOUNDS

(71) Applicant: Lantern Pharma Inc., Dallas, TX (US)

(72) Inventor: Frederick H. Hausheer, San Antonio, TX (US)

(73) Assignee: LANTERN PHARMA INC., Dallas, TX (US)

( * ) Notice: Subject to any disclaimer, the term of this patent is extended or adjusted under 35 U.S.C. 154(b) by 662 days.

This patent is subject to a terminal disclaimer.

(21) Appl. No.: 14/675,607

(22) Filed: Mar. 31, 2015

(65) Prior Publication Data

US 2016/0287539 A1 Oct. 6, 2016
US 2018/0369173 A9 Dec. 27, 2018

Related U.S. Application Data

(62) Division of application No. 12/807,931, filed on Sep. 16, 2010, now Pat. No. 9,023,805.

(51) Int. Cl.

| A61K 33/24 | (2019.01) |
| A61K 38/09 | (2006.01) |
| A61K 38/20 | (2006.01) |
| A61K 38/21 | (2006.01) |
| A61K 38/50 | (2006.01) |
| A61K 45/06 | (2006.01) |
| A61K 31/185 | (2006.01) |
| A61K 31/337 | (2006.01) |

(52) U.S. Cl.

CPC .......... *A61K 31/185* (2013.01); *A61K 31/337* (2013.01); *A61K 33/24* (2013.01); *A61K 38/09* (2013.01); *A61K 38/20* (2013.01); *A61K 38/21* (2013.01); *A61K 38/50* (2013.01); *A61K 45/06* (2013.01)

(58) Field of Classification Search
CPC ...... A61K 33/24; A61K 31/337; A61K 38/05; A61K 31/095; A61K 31/282; A61K 31/517; A61K 38/212; A61K 45/06; A61K 31/185; A61K 38/50; A61K 38/09; A61K 38/20; A61K 38/21
USPC ............ 514/19.3, 21.91, 100, 108, 449, 492
See application file for complete search history.

(56) References Cited

U.S. PATENT DOCUMENTS

| 6,596,320 B1 * | 7/2003 | Hausheer | A61K 33/24 424/649 |
| 8,026,227 B2 * | 9/2011 | Hausheer | A61K 31/185 514/100 |
| 8,143,236 B2 * | 3/2012 | Hausheer | A61K 31/105 514/100 |
| 9,023,805 B2 * | 5/2015 | Hausheer | A61K 31/517 514/19.3 |
| 9,320,760 B2 * | 4/2016 | Hausheer | A61K 31/095 |
| 2017/0007561 A1 * | 1/2017 | Hausheer | A61K 31/185 |

OTHER PUBLICATIONS

Parker et al., "BNP7787-Mediated Modulation of Paclitaxel- and Cisplatin-Induced Aberrant Microtubule Protein Polymerization In vitro", 2010, Molecular Cancer Therapeutics, 9(9), pp. 2558-2567.*
Masuda et al., "Phase I and pharmacologic study of BNP7787, a novel chemoprotector in patients with advanced non-small cell lung cancer", 2011, Cancer Chemother. Pharmacol., 67(3), pp. 533-542. (Year: 2011).*

* cited by examiner

*Primary Examiner* — My-Chau T. Tran
(74) *Attorney, Agent, or Firm* — Lewis Brisbois Bisgaard & Smith LLP; Nigamnarayan Acharya

(57) ABSTRACT

The present invention discloses and claims compositions, methods of treatment, and kits which cause an increase in the time of survival in cancer patients, wherein the cancer: (i) overexpresses thioredoxin or glutaredoxin and/or (ii) exhibits evidence of thioredoxin- or glutaredoxin-mediated resistance to one or more chemotherapeutic interventions. The present invention also discloses and claims methods and kits for the administration of said compositions to properly treat cancer patients. Additionally, the present invention discloses and claims methods and kits for quantitatively determining the level of expression of thioredoxin or glutaredoxin in the cancer cells of a cancer patient, methods of using those determined levels in the initial diagnosis and/or planning of subsequent treatment methodologies for said cancer patient, as well as ascertaining the potential growth "aggressiveness" of the particular cancer and treatment responsiveness of the particular type of cancer. Further, the present invention discloses and claims novel pharmaceutical compositions, methods, and kits used for the treatment of patients with medical conditions and disease where there is the overexpression of thioredoxin and/or glutaredoxin, and wherein this overexpression is associated with deleterious physiological effects in the patients.

8 Claims, 18 Drawing Sheets

Fig. 5

Peripheral Neuropathy – Mantel Test

| Item | Group | A | B | C | D | E | Total | Degree of freedom | Chi-square statistics | Mantel P value |
|---|---|---|---|---|---|---|---|---|---|---|
| PNQ Q1 & Q2 | BNP7787 | 8 | 45 | 31 | 6 | 1 | 91 | 1 | 0.0296 | 0.8635 |
| | Placebo | 12 | 42 | 23 | 13 | 1 | 91 | | | |

Fig. 6

| Primary Endpoint - PNQ (GEE Method) | | | |
|---|---|---|---|
| Factor | Test of Each Factor | | |
| | Degree of freedom | Chi-square statistics | P - value |
| Drug | 1 | 2.0080 | 0.1565 |
| Cycle | 5 | 63.2192 | <0.0001 |
| Age | 3 | 3.6337 | 0.3038 |
| Drug×Cycle | 5 | 5.4706 | 0.3612 |
| Drug×Age | 3 | 0.1735 | 0.6771 |

Fig. 7

Secondary Endpoint (Hemoglobin↓ · RBC↓ · Hematocrit↓)

| Adverse event | Group | 0 | 1 | 2 | 3 | 4 | Total | Degree of freedom | Chi-square statistics | Mantel P value |
|---|---|---|---|---|---|---|---|---|---|---|
| Hemoglobin ↓ | BNP7787 | 28 | 36 | 25 | 2 | 0 | 91 | 1 | 5.3752 | 0.0204 |
| | Placebo | 22 | 26 | 35 | 8 | 0 | 91 | | | |
| RBC ↓ | BNP7787 | 35 | 39 | 16 | 1 | 0 | 91 | 1 | 2.3289 | 0.1270 |
| | Placebo | 30 | 36 | 20 | 5 | 0 | 91 | | | |
| Hematocrit ↓ | BNP7787 | 36 | 37 | 17 | 1 | 0 | 91 | 1 | 4.5662 | 0.0326 |
| | Placebo | 26 | 37 | 23 | 5 | 0 | 91 | | | |

Fig. 8

Secondary Endpoint - Response Rate

Doctor

| Group | CR | PR | SD | PD | NE | Response rate (%) |
|---|---|---|---|---|---|---|
| BNP7787 | 1 | 38 | 38 | 16 | 0 | 41.9 |
| Placebo | 0 | 30 | 37 | 24 | 0 | 33.0 |
| Total | 1 | 68 | 75 | 40 | 0 | 37.5 |

Independent Radiology Committee (IRC)

| Group | CR | PR | SD | PD | NE | Response rate (%) |
|---|---|---|---|---|---|---|
| BNP7787 | 0 | 31 | 39 | 23 | 0 | 33.3 |
| Placebo | 0 | 26 | 33 | 32 | 0 | 28.6 |
| Total | 0 | 57 | 72 | 55 | 0 | 31.0 |

Fig. 13

| Overall Survival (OS) and Progression-free Survival (PFS) ||||||
|---|---|---|---|---|---|
| | Arm | Patients (n) | Events (n) | Median in Months (95% C.I.) | 1-Year Survival Rates (%) (95% C.I.) |
| PFS | No TAV | 76 | 74 | 5.5 ( 4.3 – 6.9) | 9.2 ( 4.1 - 17.0) |
| | TAV | 75 | 70 | 6.5 ( 5.0 – 7.8) | 18.7 (10.8 - 28.2) |
| OS | No TAV | 76 | 66 | 10.7 ( 8.2 - 12.2) | 39.5 (28.5 - 50.2) |
| | TAV | 75 | 56 | 11.7 ( 7.1 - 17.0) | 50.7 (38.9 - 61.3) |

Fig. 15

| | Grade 3 and 4 Treatment Related Adverse Events by Arm | | |
|---|---|---|---|
| | Arm | Grade 3 n (%) | Grade 4 n (%) |
| Dehydration | NO TAVOCEPT<br>TAVOCEPT | 12 (16)<br>6 (8) | 1 (1)<br>1 (1) |
| Nausea | NO TAVOCEPT<br>TAVOCEPT | 13 (17)<br>8 (10) | 0<br>0 |
| Vomiting | NO TAVOCEPT<br>TAVOCEPT | 7 (9)<br>2 (3) | 0<br>0 |
| Hypomagnesemia | NO TAVOCEPT<br>TAVOCEPT | 9 (12)<br>0 | 0<br>0 |

Table 5

INCREASING CANCER PATIENT SURVIVAL TIME BY ADMINISTRATION OF DITHIO-CONTAINING COMPOUNDS

RELATED APPLICATIONS

The present patent application is a Divisional Application of U.S. patent application Ser. No. 12/807,931, filed on Sep. 16, 2010 and entitled "INCREASING CANCER PATIENT SURVIVAL TIME BY ADMINISTRATION OF DITHIO-CONTAINING COMPOUNDS".

FIELD OF THE INVENTION

The present invention relates to novel pharmaceutical compositions, methods, and kits used for the treatment of cancer and other medical conditions. More specifically, the present invention relates to novel pharmaceutical compositions, methods, and kits comprising medicaments used for the treatment of lung cancer, adenocarcinoma, and other medical conditions. In addition, the present invention also relates to compositions, methods of treatment, and kits which cause an increase in time of survival in cancer patients, wherein the cancer either: (i) overexpresses thioredoxin or glutaredoxin and/or (ii) exhibits evidence of thioredoxin- or glutaredoxin-mediated resistance to one or more chemotherapeutic interventions. The present invention also relates to methods and kits for the administration of said compositions to properly treat cancer patients. Additionally, the present invention relates to methods and kits for quantitatively determining the level of expression of thioredoxin or glutaredoxin in the cancer cells of a cancer patient, methods of using those determined levels in the initial diagnosis and/or planning of subsequent treatment methodologies for said cancer patient, as well as ascertaining the potential growth "aggressiveness" of the particular cancer and treatment responsiveness of the particular type of cancer. Further, the present invention relates to novel pharmaceutical compositions, methods, and kits used for the treatment of patients with medical conditions and diseases where there is the overexpression of thioredoxin and/or glutaredoxin, and wherein this overexpression is associated with deleterious physiological effects in the patients.

BACKGROUND OF THE INVENTION

As the number of agents and treatment regimens for cancer has increased, clinicians and researchers are seeking to fully elucidate the biological, chemical, pharmacological, and cellular mechanisms which are responsible for the pathogenesis and pathophysiology of the various adverse disease manifestations, as well as how chemotherapeutic drugs exert their anti-cancer and cytotoxic or cytostatic activity on a biochemical and pharmacological basis. As described herein, with the exception of the novel conception and practice of the present invention, there are no currently-approved compositions which markedly increase the survival time of a cancer patient via a targeted therapeutic interaction that involves the direct modulation of either the thioredoxin or glutaredoxin pathways, thereby leading to increased anti-cancer and cytotoxic effects of the chemotherapeutic agent(s) within the cancer cells. Moreover, prior to the clinical studies described in the present invention, no clinical studies utilizing the novel treatment methods and compositions disclosed herein have observed "an increase in patient survival time" in a medically-important manner, but rather measured only "patient response" (i.e., tumor response—a shrinkage of tumor that is observed radiographically). These are highly innovative and novel features of the present invention.

It has been increasingly recognized that many different types of cancer cells have been shown to have increased expression and/or activity of thioredoxin and/or glutaredoxin including, but not limited to, lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

Thioredoxin and glutaredoxin are members of the thioredoxin superfamily; that mediate disulfide exchange via their Cys-containing catalytic sites. While glutaredoxins mostly reduce mixed disulfides containing glutathione, thioredoxins are involved in the maintenance of protein sulfhydryls in their reduced state via disulfide bond reduction. See, e.g., Print, W. A., et al., The role of the thioredoxin and glutaredoxin pathways in reducing protein disulfide bonds in the *Escherichia coli* cytoplasm. *J. Biol. Chem.* 272:15661-15667 (1996). The reduced form of thioredoxin is generated by the action of thioredoxin reductase; whereas glutathione provides directly the reducing potential for regeneration of the reduced form of glutaredoxin. Glutaredoxins are oxidized by substrates, and reduced non-enzymatically by glutathione. In contrast to thioredoxins, which are reduced by thioredoxin reductase, no oxidoreductase or substrate, other than those described in the present invention, has been reported to specifically reduce glutaredoxins. Instead, oxidized glutathione is regenerated by glutathione reductase. Together these components comprise the glutathione system. See, e.g., Holmgren, A. and Fernandes, A. P., Glutaredoxins: glutathione-dependent redox enzymes with functions far beyond a simple thioredoxin backup system. *Antioxid. Redox. Signal.* 6:63-74 (2004); Holmgren, A., Thioredoxin and glutaredoxin systems. *J. Biol. Chem.* 264:13963-13966 (1989). The thioredoxin system, together with the glutathione system, is regarded as a main regulator of oxidative metabolism involving the intracellular redox environment, exercising control of the cellular redox state and antioxidant defense, as well as governing the redox regulation of several cellular processes. The system is involved in direct regulation of: (i) several transcription factors, (ii) apoptosis (i.e., programmed cell death) induction, and (iii) many metabolic pathways (e.g., DNA synthesis, glucose metabolism, selenium metabolism, and vitamin C recycling). See, e.g., Amér, E. S. J., et al., Physiological functions of thioredoxin and thioredoxin reductase. *Eur. J. Biochem.* 267:6102-6109 (2000).

In brief, the overexpression (or increased activity, or both) of thioredoxin or glutaredoxin in cancer cells mediates a multi-component and multi-pathway mechanism which confers a survival advantage to cancer cells. Overexpression/increased levels or responsiveness mediated by thioredoxin and/or glutaredoxin in cancer cells can lead to several important biological alterations including, but not limited to: (i) loss of apoptotic sensitivity to therapy (i.e., drug or ionizing radiation resistance); (ii) increased conversion of RNA into DNA (involving ribonucleotide reductase); (iii) altered gene expression; (iv) increased cellular proliferation signals and rates; (v) increased thioredoxin peroxidase; and (vi) increased angiogenic activity (i.e., increased blood supply to the tumor). Accordingly, by pharmacological inactivation or modulation of thioredoxin and/or glutaredoxin by the proper medical administration of effective levels and schedules of the compositions of the present invention, can result in enhancement of chemotherapy effects and thereby lead to increased patient survival.

The compositions of the present invention comprise a medically-sufficient dose of an oxidative metabolism-affecting Formula (I) compound. The compounds of Formula (I) include pharmaceutically-acceptable salts of such compounds, as well as prodrugs, analogs, conjugates, hydrates, solvates and polymorphs, as well as stereoisomers (including diastereoisomers and enantiomers) and tautomers of such compounds. The Formula (I) compounds of the present invention also comprise a medically-sufficient dose of the disodium salt of 2,2'-dithio-bis-ethane sulfonate, which has been referred to in the literature as Tavocept™, dimesna, and BNP7787. The compositions of the present invention also comprise a medically-sufficient dose of the metabolite of disodium 2,2'-dithio-bis-ethane sulfonate, known as 2-mercapto ethane sulfonate sodium (also known in the literature as mesna) and 2-mercapto ethane sulfonate as a disulfide form which is conjugated with a substituent group consisting of:

-Cys, -Homocysteine, -Cys-Gly, -Cys-Glu, -Homocysteine, -Homocysteine-Gly, -Homocysteine-Glu, -Cys-Glu,

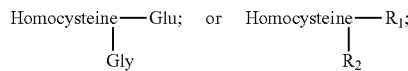

wherein $R_1$ and $R_2$ are any L- or D-amino acids.

The underlying mechanisms of the Formula (I) compounds of the present invention in increasing the survival time of cancer patients involves one or more of several novel pharmacological and physiological factors, including but not limited to, a prevention, compromise and/or reduction in the levels, responsiveness, or in the concentration and/or tumor protective metabolism of various physiological cellular thiols; these antioxidants and enzymes are increased in concentration and/or activity in cancer cells, respectively, due in part to activation and/or overexpression of thioredoxin and/or glutaredoxin levels or activity which are present in many cancer cells, and this increase in concentration and/or activity may be may be further enhanced by exposure to cytotoxic chemotherapeutic agents in tumor cells. The Formula (I) compounds of the present invention may exert therapeutic medicinal and pharmacological activity by the intrinsic composition of the molecule itself (i.e., an oxidized disulfide), as well as by oxidizing free thiols to form oxidized disulfides (i.e., by non-enzymatic SN2-mediated reactions, wherein attack of a thiol/thiolate upon a disulfide leads to the scission of the former disulfide which is accompanied by the facile departure of a thiol-containing group). As the thiolate group is far more nucleophilic than the corresponding thiol, the attack is believed to be via the thiolate, however, in some cases the sulfur atom contained within an attacking free sulfhydryl group may be the nucleophile), and may thereby lead to pharmacological depletion and metabolism of reductive physiological free thiols (e.g., glutathione, cysteine, and homocysteine).

Overexpression/increased levels or increased responsiveness mediated by thioredoxin and/or glutaredoxin in cancer cells leads to loss of apoptotic sensitivity to therapy (i.e., drug or ionizing radiation resistance), increased conversion of RNA into DNA (involving ribonucleotide reductase), increased gene expression, increased thioredoxin peroxidase, and increased angiogenic activity (i.e., increased blood supply to the tumor). Accordingly, pharmacological inactivation or modulation of thioredoxin and/or glutaredoxin by the proper medical administration of effective levels and schedules of the compositions of the present invention can result in increased patient survival.

It is believed by the Applicant of the present invention that these aforementioned mechanisms of action are mediated by the Formula (I) compounds of the present invention and metabolites thereof (e.g., 2-mercapto ethane sulfonate (mesna) and mesna heteroconjugates) and are directly involved in the marked increase in the survival time of patients suffering from cancer including, but not limited to, non-small cell lung carcinoma (NSCLC) or adenocarcinoma who received treatments utilizing the compositions, formulation, and methods of the present invention. This has extremely important implications for advancing the treatment of patients with cancer.

Compositions and formulations comprising the Formula (I) compounds of the present invention may be given using any combination of the following three general treatment methods: (i) in a direct inhibitory or inactivating manner (i.e., direct chemical interactions that inactivate thioredoxin and/or glutaredoxin) and/or depletive manner (i.e., decreasing thioredoxin and/or glutaredoxin concentrations or production rates), thereby increasing the susceptibility of the cancer cells to any subsequent administration of any chemotherapeutic agent or agents that may act directly or indirectly through the thioredoxin- and/or glutaredoxin-mediated pathways in order to sensitize the patient's cancer and thus increase the survival of the patient; and/or (ii) in a synergistic manner, where the anti-thioredoxin and/or glutaredoxin therapy is concurrently administered with chemotherapy administration when a cancer patient begins any chemotherapy cycle, in order to increase and optimize the pharmacological activity directed against thioredoxin- and/or glutaredoxin-mediated mechanisms present while chemotherapy is being concurrently administered; and/or (iii) in a post-treatment manner (i.e., after the completion of chemotherapy dose administration or a chemotherapy cycle) in order to maintain the presence of a pharmacologically-induced depletion, inactivation, or modulation of thioredoxin and/or glutaredoxin in the patient's cancer cells for as long as optimally required. Additionally, the aforementioned compositions and formulations may be given in an identical manner to increase patient survival time in a patient receiving treatment with a cytotoxic or cytostatic anti-cancer agent by any additionally clinically-beneficial mechanism(s).

I. Oxidative Metabolism

In its most simple terms, oxidative metabolism refers to the enzymatic pathways leading to the addition of oxygen (i.e., oxidation) or the removal of electrons or hydrogen (i.e., reduction) from intermediates in the pathways. The redox state of any particular biological environment can be defined as the sum of oxidative and reductive processes occurring within that environment which, in turn, directly relates to the extent to which molecules are oxidized or reduced within it. The redox potential of biological ions or molecules is a measure of their tendency to lose an electron (i.e., thereby becoming oxidized) and is expressed as $E_0$ in volts. The more strongly reducing an ion or molecule, the more negative its $E_0$. As previously stated, under normal physiological circumstances, most intracellular biological systems are predominantly found in a reduced state. Within cells, thiols (R—SH) such as glutathione (GSH), cysteine, homocysteine, and the like, are maintained in their reduced state, as are the nicotinamide nucleotide coenzymes NADH and NADPH. The opposite relationship is found in plasma, where the high partial pressure of oxygen (pO$_2$) promotes an oxidative environment, thereby leading to a high proportion (i.e., greater than 90%) of the physiological sulfur-containing amino acids and peptides (e.g., glutathione (GSH)) existing in stable oxidized (disulfide) forms. In plasma, there are currently no known enzymes that appear to reduce the disulfide forms of these sulfur-containing amino acids and GSH; this further contributes to the plasma vs. cellular disparity in terms of the relative proportions of physiological disulfides vs. thiols. Physiological circumstances can, however, arise which alter the overall redox balance and lead to a more oxidizing environment in the cell. Various complex physiological systems have evolved to remove, repair, and control the normal reducing environment. However, when the oxidizing environment overwhelms these protective mechanisms, oxidative damage and profound biological and toxic activity can occur.

In biological systems, the formation of potentially physiologically-deleterious reactive oxygen species (ROS) and that of reactive nitrogen species (RNS), may be caused from a variety of metabolic and/or environmental processes. By way of non-limiting example, intracellular ROS (e.g., hydrogen peroxide: H$_2$O$_2$; superoxide anion: O$_2^-$; hydroxyl radical: OH$^-$; nitric oxide: NO; and the like) may be generated by several mechanisms: (i) by the activity of radiation, both exciting (e.g., UV-rays) and ionizing (e.g., X-rays); (ii) during xenobiotic and drug metabolism; and (iii) under relative hypoxic, ischemic and catabolic metabolic conditions, as well as by exposure to hyperbaric oxygen. Protection against the harmful physiological activity of ROS and RNS species is mediated by a complex network of overlapping mechanisms and metabolic pathways that utilize a combination of small redox-active molecules and enzymes coupled with the expenditure of reducing equivalents. These complex networks of mechanisms, metabolic pathways, small redox-active molecules, and enzymes will be fully discussed, infra.

Concentrations of ROS and RNS which cannot be adequately dealt with by the endogenous antioxidant system can lead to damage of lipids, proteins, carbohydrates, and nucleic acids. Changes in oxidative metabolism which lead to an increase in the oxidizing environment and the formation of potentially physiologically-deleterious reactive oxygen species (ROS) and that of reactive nitrogen species (RNS) has been generally termed within the literature as "oxidative stress". It has also recently been recognized that cancer cells may respond to such "oxidative stress", induced by chemotherapy or radiation exposure, by decreasing the concentrations of ROS and oxidized thiols and well as by increased concentrations of thiol and anti-oxidants. It should be noted that when either or both of these mechanisms are operative, the subject's tumor cells may become resistant to chemotherapy and radiation therapy, thereby representing an important obstacle to curing or controlling the progression of the subject's cancer.

The putative mechanisms of the Formula (I) compositions of the present invention which function in the potentiation of the anti-cancer activity of chemotherapeutic agents may involve one or more of several novel pharmacological and physiological factors, including but not limited to, a prevention, compromise, and/or reduction in the normal increase, responsiveness, or in the concentration and/or tumor protective metabolism of glutathione/cysteine and other physiological cellular thiols; these antioxidants and enzymes are increased in concentration and/or activity, respectively, in response to the induction of intracellular oxidative stress which may be caused by exposure to cytotoxic chemotherapeutic agents in tumor cells. Additional information regarding certain mechanisms which may be involved in the biological activities of the Formula (I) compounds is disclosed in U.S. patent application Ser. No. 11/724,933, filed Mar. 16, 2007, the disclosure of which is hereby incorporated by reference in its entirety.

II. Physiological Cellular Thiols

Thiol groups are those which contain functional CH$_2$—SH groups within conserved cysteinyl residues. It is these thiol-containing proteins which have been elucidated to play the primary role in redox-sensitive reactions. Their redox-sensing abilities are thought to occur by electron flow through the sulfhydryl side-chain. Thus, it is the unique properties afforded by the sulfur-based chemistry in protein cysteines (in some cases, possibly in conjunction with chelated central metal atoms) that is exploited by transcription factors which "switch" between an inactive and active state in response to elevated concentrations of ROS and/or RNS. It should be noted that the majority of cellular protein thiols are compartmentalized within highly reducing environments and are therefore "protected" from such oxidation. Hence, only proteins with accessible thiol moieties, and higher oxidation potentials are likely to be involved in redox-sensitive signaling mechanisms.

There are numerous naturally-occurring thiols and disulfides that are involved in oxidative metabolism. The most abundant biologically-occurring amino acid is cysteine, along with its disulfide form, cystine. Another important and highly abundant intracellular thiol is glutathione (GSH), which is a tripeptide comprised of γ-glutamate-cysteine-glycine. Thiols can also be formed in those amino acids which contain cysteine residues including, but not limited to, cystathionine, taurine, and homocysteine. Many oxidoreductases and transferases rely upon cysteine residues for their physiological catalytic functions. There are also a large number of low molecular weight cysteine-containing compounds, such a Co-enzyme A and glutathione, which are vital enzymes in maintaining oxidative/reductive homeostasis in cellular metabolism. These compounds may also be classified as non-protein sulfhydryls (NPSH).

Structural and biochemical data has also demonstrated that thiol-containing cysteine residues and the disulfide cystine, play a ubiquitous role in allowing proteins to respond to ROS. The redox-sensitivity of specific cysteine residues imparts specificity to ROS-mediated cellular signaling. By reacting with ROS, cysteine residues function as "detectors" of redox status; whereas the consequent chemical change in the oxidized cysteine can be converted into a protein conformational change, hence providing an activity or response.

Within biological systems, thiols undergo a reversible oxidation/reduction reaction, as illustrated below, which are often catalyzed by transition metals. These reactions can also involve free radicals (e.g., thioyl RS) as intermediates. In addition, proteins which possess SH/SS groups can interact with the reduced form of GSH in a thiol-disulfide exchange. Thiols and their disulfides are reversibly linked, via specific enzymes, to the oxidation and reduction of NADP and NADPH. This reversible oxidation/reduction reaction is shown in

TABLE 1

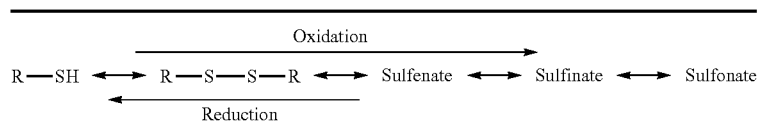

There is increasing experimental evidence that indicates that thiol-containing proteins are sensitive to thiol modification and oxidation when exposed to changes in the redox state. This sensing of the redox potential is thought to occur in a wide range of diverse signal transduction pathways. Moreover, these redox sensing proteins play roles in mediating cellular responses to changes in intracellular oxidative metabolism (e.g., increased cellular proliferation).

One of the primary enzymes involved in the synthesis of cellular thiols is cysteine synthase, which is widely distributed in human tissues, where it catalyzes the synthesis of cysteine from serine. The absorption of cystine and structurally-related amino acids (e.g., ornithine, arginine, and lysine) are mediated by a complex transporter system. The Xc transporter, as well as other enzymes, participate in these cellular uptake mechanisms. Once transported into the cell, cystine is rapidly reduced to cysteine, in an enzymatic reaction which utilizes reduced glutathione (GSH). In the extracellular environment, the concentrations of cystine are typically substantially higher than cysteine, and whereas the reverse is true in the intracellular environment.

III. Lung Cancer

Lung cancer is reported to be the leading cause of smoking- and cancer-related mortality in both sexes. The prevalence of lung cancer is second only to that of prostate cancer in men and breast cancer in women. In the United States, lung cancer was reported recently to surpass heart disease as the leading cause of smoking-related mortality. Most lung carcinomas are diagnosed at an advanced stage, conferring a poorer prognosis. Lung cancer is estimated to be the cause of 921,000 deaths each year worldwide, accounting for approximately 18% of all cancer-related deaths. Lung cancer is highly lethal, with a 5-year patient survival rate of only 14% being observed in the United States. An estimated 164,100 (i.e., 89,500 in men and 74,600 in women) new lung cancer cases will occur this year (2008) in the United States. See, e.g., National Cancer Institute-2008 Lung Cancer Estimates (www.Cancer.gov).

Lung cancer manifests with symptoms produced by the primary tumor, locoregional spread, metastatic disease, or ectopic hormone production. Approximately 7-10% of patients with lung cancer are asymptomatic and their cancers are diagnosed incidentally after a chest x-ray performed for other reasons. The symptoms produced by the primary tumor depend on its location (e.g., central, peripheral).

Of the symptoms produced by the primary tumor, central tumors are generally squamous cell carcinomas and produce symptoms or signs of cough, dyspnea, atelectasis, postobstructive pneumonia, wheezing, and hemoptysis, and peripheral tumors are generally adenocarcinomas or large cell carcinomas and, in addition to causing cough and dyspnea, can cause symptoms or signs from pleural effusion and severe pain as a result of infiltration of parietal pleura and the chest wall. Symptoms due to locoregional spread can include: (i) superior vena cava obstruction; (ii) paralysis of the left recurrent laryngeal nerve and phrenic nerve palsy (causing hoarseness and paralysis of the diaphragm); (iii) pressure on the cervical sympathetic plexus (causing Horner syndrome); (iv) dysphagia resulting from esophageal compression; (v) pericardial effusion and cardiac tamponade; and (vi) superior sulcus apical primary tumors can cause compression of the brachial plexus roots as they exit the neural foramina, causing intense, radiating neuropathic pain in the ipsilateral upper extremity (e.g., Pancoast tumors). Lung cancer is associated with a variety of paraneoplastic syndromes: (i) most of such paraneoplastic syndromes are associated with small cell lung cancer; (ii) squamous cell carcinomas are more likely to be associated with hypercalcemia due to parathyroidlike hormone production; and (iii) clubbing and hypertrophic pulmonary osteoarthropathy and the Trousseau syndrome of hypercoagulability are caused more frequently by adenocarcinomas. Eaton-Lambert myasthenic syndrome is reported in association with small cell and non-small cell lung cancers. Paraneoplastic syndromes can pose debilitating problems in cancer patients and can complicate the medical management of such patients.

Non-small cell lung cancer (NSCLC) accounts for more than 80% of all primary lung cancer, and surgically resectable (with curative intent) cases account for less than 30%. Chemotherapy and radiotherapy are the mainstays of treatment in unresectable cases, but the median survival period is only 15-20 months and the 3-year survival rate is approximately 30-40% in stage IIIA and IIIB cases. The prognosis is even worse in stage IV patients with a median survival period of 8-10 months and a 1-year survival rate of less than 30%. At these advanced stages, the main therapeutic objectives are increasing the survival period and preserving the quality of life; these patients are not generally considered curable. It is important to consider the important concept of increasing the observed survival rate as a prerequisite for achieving a curative outcome in any therapeutic intervention that involves a defined patient population (e.g., non-small cell lung cancer patients) that is considered to be incurable. See, e.g., Cortes-Funes H., New Treatment Approaches for Lung Cancer and Impact on Survival. *Semin. Oncol.* 29:26-29 (2002); Fukuoka, M and Saijoh, N., Practical medicine—Lung cancer, *Nannkodo* (2001). NSCLC is pathologically characterized further into adenocarcinoma, squamous cell carcinoma, large cell carcinoma, and other less common forms. Clinically there are also important differences in NSCLC that can be observed in smokers and non-smokers.

A summary of clinical characteristics by histologic NSCLC subtype include:

Adenocarcinoma is the most frequent non-small cell lung cancer (NSCLC) in the United States, representing 35% to more than 50% of all lung cancers, usually occurring in a peripheral location within the lung and arising from bronchial mucosal glands. Adenocarcinoma is the most common histologic subtype, manifesting as a scar carcinoma. This is a subtype observed most commonly in persons who do not smoke, however, adenocarcinoma is also common in smokers. This type of NSCLC may also manifest as multifocal tumors in a bronchoalveolar form. Bronchoalveolar carcinoma is a distinct subtype of adenocarcinoma with the classic manifestation as an interstitial lung disease upon radiographic imaging. Bronchoalveolar carcinoma arises from type II pneumocytes and grows along alveolar septa. This subtype may manifest as a solitary peripheral nodule, multifocal disease, or a rapidly progressing pneumonic form. A characteristic finding in persons with advanced disease is voluminous watery sputum. Overexpression of thioredoxin and/or glutaredoxin has been noted in adenocarcinomas of the lung.

Squamous cell carcinoma accounts for approximately 25-30% of all lung cancers. The classic manifestation is a cavitary lesion in a proximal bronchus. This type is characterized histologically by the presence of keratin pearls and can be detected based on results from cytologic studies because it has a tendency to exfoliate. It is the type most often associated with hypercalcemia.

Large cell carcinoma accounts for approximately 10-15% of lung cancers, typically manifesting as a large peripheral mass upon radiographic imaging. Histologically, this type has sheets of highly atypical cells with focal necrosis, with no evidence of keratinization (typical of squamous cell carcinoma) or gland formation (typical of adenocarcinomas). Patients with large cell carcinoma are more likely to develop gynecomastia and galactorrhea as paraneoplastic syndromes.

Various types of lung cancer have been shown to have an increased oxidative metabolism and/or increased concentrations of thioredoxin and/or glutaredoxin, and may further overexpress these in response to chemotherapy, thus resulting in tumor-mediated drug resistance to chemotherapy. Therefore, any tumors that possess the characteristics of an increased oxidative metabolism and/or increased concentration of thioredoxin and/or glutaredoxin are more amenable to the therapeutic benefits, including increased survival outcomes that would be mediated by an intervention from a composition or method of the present invention.

IV. Adenocarcinoma

Adenocarcinoma is a histopathological description and classification of cancers that originate primarily from glandular tissue. Glandular tissue comprises organs that synthesize a substance for release such mucin or hormones. Glands can be divided into two general groups: (i) endocrine glands—glands that secrete their product directly onto a surface rather than through a duct, often into the blood stream and (ii) exocrine glands—glands that secrete their products via a duct, often into cavities inside the body or its outer surface. Exocrine glands may be further differentiated into three categories: apocrine, holocrine, and merocrine. However, it should be noted that to be classified as adenocarcinoma, the cells do not necessarily need to be part of a gland, as long as they have secretory properties. Adenocarcinoma may be derived from various tissues including, but not limited to, breast, colon, lung, prostate, salivary gland, esophagus, stomach, liver, gall bladder and bile ducts, pancreas (99% of pancreatic cancers are ductal adenocarcinomas), cervix, vagina, ovary, and uterus, prostate, as well as unknown primary adenocarcinomas, which are not uncommon.

Adenocarcinoma is a neoplasm which frequently presents marked difficulty in differentiating from where and from which type of glandular tissue the tumor(s) arose. Thus, an adenocarcinoma identified in the lung may have had its origins (or may have metastasized) from an ovarian adenocarcinoma. Cancer for which a primary site cannot be found is called cancer of unknown primary, and adenocarcinomas of unknown primary are the most common type of unknown primary cancers. The primary site is identified in only approximately 10-20% of patients during their remaining life times and it frequently is not identified until post-mortem examination. It has been reported that approximately 60% of patients (i.e., over 50,000 patients per annum in the United States) who are diagnosed with carcinoma of unknown primary site suffer from adenocarcinoma.

A diagnosis of adenocarcinoma which is not further described (i.e., adenocarcinoma not otherwise specified; adenocarcinoma NOS) is often a preliminary diagnosis and can frequently be clarified with the use of immunohistochemistry or fluorescent in situ hybridization (FISH) (see, e.g., Dabbs, D. J. and Silverman, J. F., Immunohistochemical and Fluorescent in situ Hybridization Workup of Metastatic Carcinoma of Unknown Primary. *Path. Case Rev.* 6(4):146-153 (2005)), and/or various imaging methodologies including, but not limited to, computerized tomography (CT), magnetic resonance imaging (MRI), and positron emission tomography (PET).

Immunohistochemistry refers to the process of localizing proteins in cells of a tissue section exploiting the principle of antibodies binding specifically to antigens in biological tissues. Immunohistochemistry is also widely used in basic research to understand the distribution and localization of biomarkers in different parts of a tissue.

Immunohistochemical staining is a widely used specialized technique in the diagnosis of cancer and the classification of neoplasms. The antibodies utilized may be either polyclonal or monoclonal in nature and may be directed against cell components or products which can include: (i) enzymes (e.g., prostatic acid phosphatase, neuron-specific enoenzymes); (ii) normal tissue components (e.g., keratin, neurofilaments); and (iii) hormones or hormone receptors (e.g., estrogen receptor, oncofetal antigens, S-100 proteins). It should be noted that specific molecular markers are characteristic of particular cancer types. For example, adenocarcinoma often gives positive immunohistochemical results for thyroid transcription factor-1 (TTF-1). Visualizing an antibody-antigen interaction can be accomplished in a number of ways. In the most common instance, an antibody is conjugated to an enzyme, such as peroxidase, that can catalyze a color-producing reaction, as with immunoperoxidase staining. Alternatively, the antibody can also be tagged to a fluorophore, such as FITC, rhodamine, Texas Red, or DyLight Fluor, as with immunofluorescence.

Fluorescent in situ hybridization (FISH) is a cytogenetic technique that can be used to detect and localize the presence or absence of specific DNA sequences on chromosomes. It utilizes fluorescent-tagged nucleic acid probes that bind to only those parts of the chromosome with which they show a high degree of nucleotide sequence complementarity. Fluorescence microscopy can be used to find out where the fluorescent probe bound to the chromosome.

Adenocarcinomas are quite common and arise in a variety of sites. Similar to NSCLC, it has also been shown that adenocarcinomas have an increased oxidative metabolism and/or increased concentrations of thioredoxin and/or glutaredoxin, and may further overexpress these in response to chemotherapy, resulting in tumor-mediated drug resistance to chemotherapy.

As set forth above, non-small cell lung carcinoma (NSCLC) and adenocarcinoma are highly prevalent forms of cancer and account for a large percentage of the deaths associated with cancer world-wide. Given the relatively refractory nature of NSCLC and adenocarcinoma to many forms of therapy, there remains a need for the development of compositions and treatment regimens that are both generally safe and effective for increasing the survival time of patients receiving chemotherapy, slowing the progression of their tumors, and/or stimulating or maintaining the beneficial physiological function of important bodily processes in normal (i.e., non-cancerous) cells and tissues. It has also been recognized that both NSCLC and adenocarcinomas have an increased oxidative metabolism and/or increased concentrations of thioredoxin and/or glutaredoxin, and may further overexpress these in response to chemotherapy, resulting in tumor-mediated drug resistance to chemotherapy. Therefore, any tumors that possess these characteristics are more amenable to the therapeutic benefits, including increased survival outcomes, which would be mediated by an intervention from a composition or method of the present invention. Recent, surprising and medically-important new finding and functions, based upon recent clinical trial results, have been observed involving the Formula (I) compounds set forth in the present invention. These observations have extremely important implications for the treatment of cancer and various other medical conditions.

In addition to the foregoing considerations regarding cancer, many patients, including cancer patients receiving chemotherapy, are also in need of: maintaining or stimulating hematological function; maintaining or stimulating erythropoietin function or synthesis; mitigating or preventing anemia; and maintaining or stimulating pluripotent, multipotent, and unipotent normal stem cell function or synthesis.

SUMMARY OF THE INVENTION

The invention described and claimed herein has many attributes and embodiments including, but not limited to, those set forth or described or referenced in this Summary section. However, it should be noted that this Summary is not intended to be all-inclusive, nor is the invention described and claimed herein limited to, or by, the features or embodiments identified in said Summary. Moreover, this Summary is included for purposes of illustration only, and not restriction.

As previously discussed, many types of cancer cells have been shown to have increased expression and/or activity of thioredoxin or glutaredoxin including, but not limited to, lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma. The overexpression (or increased activity, or both) of thioredoxin and/or glutaredoxin in cancer cells mediates a multi-component and multi-pathway survival advantage to cancer cells which becomes manifest as chemotherapy drug resistance to apoptosis. Such overexpression of either of these key oxidoreductase pathways thereby results in the lack or impediment of the intended therapeutic effects of medical interventions on cancer cells, and further results in an observed shortened patient survival that is believed to be mediated by the presence and persistence of increased concentrations or expression of thioredoxin or glutaredoxin, which in turn promote tumor-mediated resistance to chemotherapy-induced apoptosis, overexpression of oxidoperoxidases, increased conversion of RNA into DNA, increased nuclear transcription, increased cell proliferation, and/or increased angiogenesis, any of which can act in concert to provide the cancer cells the ability to resist the cytotoxic actions of chemotherapy and radiation therapy and thereby decrease the time of patient survival.

The present invention involves the medicinal and pharmacological inactivation and modulation of the thioredoxin/glutaredoxin system which thereby inactivates, reverses or modulates the drug-resistant properties in the cancer cells that are otherwise imparted by the increased levels or overexpression of thioredoxin/glutaredoxin in said cancer cells. The medicinal and pharmacological inactivation involves the administration of a Formula (I) compound of the present invention. Any of the aforementioned types of cancer that have increased expression or concentrations of thioredoxin and/or glutaredoxin are susceptible to and may benefit from thioredoxin-/glutaredoxin-based intervention by the present invention. The present invention also teaches how to optimize the schedule, dose, and combination of chemotherapy regimens in patients by the identification in-advance and through-out treatment of the thioredoxin/glutaredoxin levels and the metabolic state within a sample of cancer cells isolated from the individual patients. Moreover, the use of kits that enable diagnostic and therapeutic optimization of the compositions and methods of the present invention to further enhance the survival outcome and benefit to patients by, for example, the determination of the optimum chemotherapeutic drug regimen to utilize. The present invention also teaches how to identify, in advance, those patients who would not be likely to benefit from such intervention by the use of diagnostic kits, thereby allowing other treatment approaches that may be more clinically efficacious to be pursued. In addition, the diagnostic kits of the present invention allow for continued monitoring of patients and their biochemical responses to treatment.

In brief, the present invention discloses and claims: (i) compositions which cause an increase in time of survival in patients with cancer; wherein the cancer either overexpresses thioredoxin or glutaredoxin and/or exhibits or possesses thioredoxin- or glutaredoxin-mediated resistance to one or more chemotherapeutic agents or interventions; (ii) methods of treatment which cause an increase in the time of survival in patients with cancer; wherein the cancer either overexpresses thioredoxin or glutaredoxin and/or exhibits or possesses thioredoxin- or glutaredoxin-mediated resistance to one or more chemotherapeutic drugs; (iii) kits for the administration of these compositions to treat patients with cancer; (iv) methods for quantitatively ascertaining the level of expression of thioredoxin or glutaredoxin in patients with cancer; (v) methods of using the level and pattern of expression of thioredoxin or glutaredoxin in the cancer in the initial diagnosis, planning of subsequent treatment methodologies, and/or ascertaining the potential treatment responsiveness of the specific cancer of the patients with cancer; (vi) kits for quantitatively ascertaining the level of expression of thioredoxin or glutaredoxin in the cancer of patients with cancer; (vii) methods of treatment which cause an increase in time of survival in patients with cancer; wherein the cancer either overexpresses thioredoxin or glutaredoxin and/or exhibits or possesses thioredoxin- or glutaredoxin-mediated resistance to one or more chemotherapeutic drugs and the treatment comprises the administration of the chemotherapeutic agents that are sensitive to thioredoxin and/or glutaredoxin overexpression, either of which result in tumor mediated drug resistance and enhanced angiogenesis; and (viii) methods for optimizing the schedule, dose, and combination of chemotherapy regimens in patients by ascertaining, in-advance and throughout the treatment course, the thioredoxin levels, glutaredoxin levels and metabolic state in a sample from the patient with cancer.

It should also be noted that, the Japan Phase III non-small cell lung carcinoma (NSCLC) Clinical Trial and the United States (U.S.) Phase II NSCLC Clinical Trial, that are discussed and described in the present invention represent controlled clinical evidence of a survival increase caused by a thioredoxin and/or glutaredoxin inactivating or modulating medicament (that act pharmacologically in the manner of the oxidative metabolism-affecting Formula (I) compounds of the present invention). These two aforementioned clinical trials will be fully discussed in a later section. However, it is observed from the data from both of these controlled clinical trials that there is a marked increase in patient survival, especially in the non-small cell lung carcinoma, adenocarcinoma sub-type patients receiving a Formula (I) compound of the present invention. For example, there was an increase in median survival time of approximately 138 days (i.e., 4.5 months) and approximately 198 days (i.e., 6.5 months) for adenocarcinoma patients in the Tavocept arm of the Japan Phase III NSCLC Clinical Trial and the U.S. Phase II NSCLC Clinical Trial, respectively.

The compositions of the present invention comprise a medically-sufficient dose of an oxidative metabolism-affecting Formula (I) compound including, but not limited to, the disodium salt of 2,2'-dithio-bis-ethane sulfonate, or a pharmaceutically-acceptable salt or analog thereof. The disodium salt of 2,2'-dithio-bis-ethane sulfonate has also been referred to in the literature as dimesna, Tavocept™, and BNP7787. By way of non-limiting example, disodium 2,2'-dithio-bis-ethane sulfonate (dimesna, Tavocept™, and BNP7787) is a known compound and can be manufactured by methods known in the art. See, e.g., *J. Org. Chem.* 26:1330-1331 (1961); *J. Org. Chem.* 59:8239 (1994). In addition, various salts and analogs of 2,2'-dithio-bis-ethane sulfonate, as well as other dithioethers may also be synthesized as outlined in U.S. Pat. Nos. 5,808,160, 6,160,167 and 6,504,049, the disclosures of which are hereby incorporated by reference in their entirety. Additionally, the compositions of the present invention also comprise a medically-sufficient dose of the metabolite of disodium 2,2'-dithio-bis-ethane sulfonate, known as 2-mercapto ethane sulfonate sodium (also known in the literature as mesna) and 2-mercapto ethane sulfonate conjugated with a substituent group consisting of:
-Cys, -Homocysteine, -Cys-Gly, -Cys-Glu, -Homocysteine, -Homocysteine-Gly, -Homocysteine-Glu,-Cys-Glu,

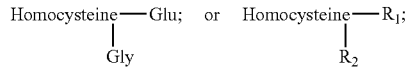

wherein $R_1$ and $R_2$ are any L- or D-amino acids. These aforementioned heteroconjugate compounds may be synthesized as described in Published U.S. Patent Application 2005/0256055, the disclosure of which is incorporated herein, by reference, in its entirety.

The mechanisms of the oxidative metabolism-affecting Formula (I) compounds of the present invention in increasing the survival time of cancer patients may involve one or more of several novel pharmacological and physiological factors, including but not limited to, a prevention, compromise and/or reduction in the normal increase, responsiveness, or in the concentration and/or tumor protective metabolism of various physiological cellular thiols; these antioxidants and enzymes are increased in concentration and/or activity, respectively, in response to the induction of changes in intracellular oxidative metabolism which may be caused by exposure to cytotoxic/cytostatic chemotherapeutic agents in tumor cells. The Formula (I) compounds of the present invention may exert an oxidative activity by the intrinsic composition of the molecule itself (i.e., an oxidized disulfide), as well as by oxidizing free thiols to form oxidized disulfides (i.e., by non-enzymatic SN2-mediated reactions, wherein attack of a thiol/thiolate upon a disulfide leads to the scission of the former disulfide which is accompanied by the facile departure of a thiol-containing group. As the thiolate group is far more nucleophilic than the corresponding thiol, the attack is believed to be via the thiolate, however, in some cases the sulfur atom contained within an attacking free sulfhydryl group may be the nucleophile), and may thereby lead to pharmacological depletion and metabolism of reductive physiological free thiols (e.g., glutathione, cysteine, and homocysteine).

The Applicant has determined that some of the novel principles governing these reactions involve the increased (i.e., greater stability of) solvation free energy of the disulfide and free-thiol products that are formed from the reaction; therefore these reactions appear to be largely driven by the favorable thermodynamics of product formation (i.e., exothermic reactions). One or more of these pharmacological activities will thus have an augmenting (additive or synergistic) effect on the cytotoxic or cytostatic activity of chemotherapeutic agents administered to patients with cancer, with the additional cytotoxic or cytostatic activity resulting from the combined administration of the oxidative metabolism-affecting Formula (I) compounds of the present invention and chemotherapy compounds, thereby leading to: (i) an increase in the cytotoxic and cytoreductive anti-cancer efficacy and decreases in tumor-mediated resistance of the various co-administered chemotherapeutic agents, e.g., platinum- and alkylating agent-based drug efficacy and tumor-mediated drug resistance; (ii) thioredoxin inactivation by the Formula (I) compounds of the present invention, thereby increasing apoptotic sensitivity and decreasing mitogenic/cellular replication signaling in cancer cells; (iii) the killing of cancer cells directly use of a Formula (I) compound, including a key metabolite of disodium 2,2'-dithio-bis-ethane sulfonate (also known in the literature as dimesna, Tavocept™, or BNP7787), 2-mercapto ethane sulfonate sodium (also known in the literature as mesna) which possesses intrinsic cytotoxic or cytostatic activity (i.e., causes apoptosis) in some tumors; and/or (iv) enhancing oxidative metabolism or compromising the anti-oxidative response of cancerous tumor cells, or both, which may thereby enhance their oxidative biological and physiological state by use of a Formula (I) compound, including 2,2'-dithio-bis-ethane sulfonate compounds (and possibly mesna or mesna heteroconjugates). This may serve to subsequently increase the amount of oxidative damage in tumor cells exposed to chemotherapy agent(s), thereby enhancing chemotherapy agent-mediated anti-cancer cytotoxic, cytostatic, and apoptotic effects. Thus, by enhancing oxidative metabolism and/or reducing or compromising the total anti-oxidative capacity or responsiveness of cancer tumor cells, an increase in anti-cancer activity can be achieved—with a resulting increase in the time of patient survival.

As previously discussed, compositions and formulations comprising the oxidative metabolism-affecting Formula (I) compounds of the present invention may be given using any combination of the following three general treatment methods: (i) in a direct inhibitory or inactivating manner (i.e., direct chemical interactions that inactivate thioredoxin and/ or glutaredoxin) and/or depletive manner (i.e., decreasing thioredoxin and/or glutaredoxin concentrations or production rates) to a cancer patient, and thereby increasing the susceptibility of the cancer cells to any subsequent administration of any chemotherapeutic agent or agents that may act directly or indirectly through the thioredoxin and/or glutaredoxin-mediated pathways in order to sensitize the patient's cancer cells and thus to enhance the anti-tumor cytotoxicity of the subsequently-administered chemotherapeutic agent or agents; and/or (ii) in a synergistic manner, where the anti-thioredoxin and/or glutaredoxin therapy is concurrently administered with chemotherapy administration when a cancer patient begins any chemotherapy cycle, in order to augment and optimize the pharmacological activity directed against thioredoxin and/or glutaredoxin mediated mechanisms present while chemotherapy is being concurrently administered; and/or (iii) in a post-treatment manner (i.e., after the completion of chemotherapy dose administration or a chemotherapy cycle) in order to maintain the presence of a pharmacologically-induced depletion, inactivation, or modulation of thioredoxin and/or glutaredoxin in the patient's cancer cells for as long as optimally required. Additionally, the aforementioned compounds may be given in an identical manner to augment or enhance the anti-cancer activity of a cytotoxic or cytostatic agent by any additionally clinically-beneficial mechanism(s).

The oxidative metabolism-affecting Formula (I) compounds of the present invention are compounds which are also capable of increasing the therapeutic efficacy (i.e., therapeutic index) of a chemotherapeutic drug, composition, and/or regimen, thus leading to an overall increase in patient survival by, for example: (i) increasing tumor response rate, increasing the time to tumor progression, and delaying/decreasing the onset of metastatic disease; (ii) causing a lack of interference with the anti-cancer cytotoxic and cytostatic action of an administered chemotherapeutic agent(s); and (iii) causing a lack of tumor desensitization or drug resistance to the cytotoxic and cytostatic activity of an administered chemotherapeutic agent(s).

In one embodiment of the present invention, a composition for increasing survival time in a patient with cancer is disclosed, wherein the cancer, either: (i) overexpress thioredoxin or glutaredoxin and/or (ii) exhibit evidence of thioredoxin-mediated or glutaredoxin-mediated resistance to the chemotherapeutic agent or agents used to treat said patient with cancer; is administered in a medically-sufficient dose to the patient with cancer, either prior to, concomitantly with, or subsequent to the administration of a chemotherapeutic agent or agents whose cytotoxic or cytostatic activity is adversely by effected by either: (i) the overexpression of thioredoxin or glutaredoxin and/or (ii) thioredoxin-mediated or glutaredoxin-mediated treatment resistance.

It should be noted that the exhibition of thioredoxin-mediated or glutaredoxin-mediated treatment resistance is described as "evidence of" due to the fact that it is neither expected, nor possible to prove with 100% certainty that the cancer cells exhibit thioredoxin-mediated or glutaredoxin-mediated treatment resistance, prior to the treatment of the patient. By way of non-limiting example, the current use of, e.g., florescence in situ hybridization (FISH) or immunohistochemistry (IHC) to guide treatment decisions for HER2/neu-based therapy are predicated upon the probability of the overexpression/increased concentrations of HER2/neu being correlated with the probability of a therapeutic response. Such expectation of a therapeutic response is not 100% certain, and is related to many factors, not the least of which is the diagnostic accuracy of the test utilized which, in turn, is also limited by the sampling of the tumor and various other factors (e.g., laboratory methodology/technique, reagent quality, and the like).

In another embodiment, the cancer of origin for treatment with the present invention is selected from the group consisting of any cancer which either: (i) overexpresses thioredoxin or glutaredoxin and/or (ii) exhibits evidence of thioredoxin-mediated or glutaredoxin-mediated resistance to the chemotherapeutic agent or agents being used to treat said patient with cancer.

In another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In one embodiment of the present invention, a composition for increasing survival time in a patient with non-small cell lung carcinoma is disclosed, wherein the non-small cell lung carcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with non-small cell lung carcinoma; is administered in a medically-sufficient dose to the patient with non-small cell lung carcinoma, either prior to, concomitantly with, or subsequent to the administration of a chemotherapeutic agent or agents whose cytotoxic or cytostatic activity is adversely by effected by either: (i) the overexpression of thioredoxin or glutaredoxin and/or (ii) the thioredoxin-mediated or glutaredoxin-mediated treatment resistance.

In another embodiment of the present invention, a composition for increasing survival time in a patient with adenocarcinoma is disclosed, wherein the adenocarcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with adenocarcinoma; is administered in a medically-sufficient dose to the patient with adenocarcinoma, either prior to, concomitantly with, or subsequent to the administration of a chemotherapeutic agent or agents whose cytotoxic or cytostatic activity is adversely by effected by either: (i) the overexpression of thioredoxin or glutaredoxin and/or (ii) the thioredoxin-mediated or glutaredoxin-mediated treatment resistance.

In one embodiment of the present invention, a method of increasing survival time in a patient with cancer is disclosed, wherein the cancer, either: (i) overexpresses thioredoxin or glutaredoxin and/or (ii) exhibits evidence of thioredoxin-mediated or glutaredoxin-mediated resistance to the chemotherapeutic agent or agents used to treat said patient with non-small cell lung carcinoma; wherein said method comprises the administration of a medically-sufficient dose of a Formula (I) compound to said patient with cancer either prior to, concomitantly with, or subsequent to the administration of a chemotherapeutic agent or agents whose cytotoxic or cytostatic activity is adversely by effected by either: (i) the overexpression of thioredoxin or glutaredoxin and/or (ii) the thioredoxin-mediated or glutaredoxin-mediated treatment resistance.

In another embodiment, the cancer of origin for treatment with the present invention is selected from the group consisting of any cancer which either: (i) overexpresses thioredoxin or glutaredoxin and/or (ii) exhibits evidence of thioredoxin-mediated or glutaredoxin-mediated resistance to the chemotherapeutic agent or agents being used to treat said patient with cancer.

In another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In another embodiment of the present invention, a method of increasing survival time in a patient with non-small cell lung carcinoma is disclosed, wherein the non-small lung carcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with non-small cell lung carcinoma; wherein said method comprises the administration of a medically-sufficient dose of a Formula (I) compound to said patient with non-small cell lung carcinoma either prior to, concomitantly with, or subsequent to the administration of a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance.

In yet another embodiment of the present invention, a method of increasing survival time in a patient with adenocarcinoma is disclosed, wherein the adenocarcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with adenocarcinoma; wherein said method comprises the administration of a medically-sufficient dose of an oxidative metabolism-affecting Formula (I) compound to said patient with adenocarcinoma either prior to, concomitantly with, or subsequent to the administration of a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance.

In one embodiment of the present invention, a kit comprising an oxidative metabolism-affecting Formula (I) compound for administration, and instructions for administering said Formula (I) compound to a patient with cancer in an amount sufficient to cause an increase in the survival time of said patient with cancer who is receiving a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance, is disclosed.

In another embodiment, the cancer of origin for treatment with the present invention is selected from the group consisting of any cancer which either: (i) overexpresses thioredoxin or glutaredoxin and/or (ii) exhibits evidence of thioredoxin-mediated or glutaredoxin-mediated resistance to the chemotherapeutic agent or agents being used to treat said patient with cancer.

In another embodiment of the present invention, a kit comprising an oxidative metabolism-affecting Formula (I) compound for administration, and instructions for administering said Formula (I) compound to a patient with non-small cell lung carcinoma in an amount sufficient to cause an increase in the survival time of said patient who is receiving a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance, is disclosed.

In yet another embodiment, a kit comprising a Formula (I) compound for administration, and instructions for administering said Formula (I) compound to a patient with adenocarcinoma in an amount sufficient to cause an increase in the survival time of said patient who is receiving a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance, is disclosed.

In one embodiment of the present invention, a method for quantitatively ascertaining the level of thioredoxin or glutaredoxin DNA, mRNA, or protein in cells which have been isolated from a patient who is suspected of having cancer or has already been diagnosed with cancer is disclosed; wherein the method used to identify levels of thioredoxin or glutaredoxin is selected from the group consisting of: fluorescence in situ hybridization (FISH), nucleic acid microarray analysis, immunohistochemistry (IHC), and radioimmunoassay (RIA).

In another embodiment, the method is used in the initial diagnosis, the planning of subsequent treatment methodologies, and/or determining the potential aggressiveness of cancer growth in a patient suffering from a type of cancer in which the cells comprising the cancer either: (i) overexpress thioredoxin or glutaredoxin and/or (ii) exhibit evidence of thioredoxin-mediated or glutaredoxin-mediated treatment resistance to the chemotherapeutic agents or agents already being administered to the patient with cancer.

In still another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In one embodiment of the present invention, a kit with instructions for quantitatively ascertaining the level of thioredoxin or glutaredoxin DNA, mRNA, or protein in cells which have been isolated from a patient who is suspected of having cancer or has already been diagnosed with cancer is disclosed; wherein the kit uses a method to identify levels of thioredoxin or glutaredoxin which is selected from the group consisting of: fluorescence in situ hybridization (FISH), nucleic acid microarray analysis, immunohistochemistry (IHC), and radioimmunoassay (RIA).

In yet another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In another embodiment of the present invention, a method for increasing survival time in a patient with cancer is disclosed, wherein said cancer, either: (i) overexpresses thioredoxin or glutaredoxin and/or (ii) exhibits evidence of thioredoxin-mediated or glutaredoxin-mediated resistance to the chemotherapeutic agent or agents used to treat said patient with cancer; wherein said method comprises the administration of a medically-sufficient dose of a Formula (I) compound to said patient with cancer either prior to, concomitantly with, or subsequent to the administration of the chemotherapeutic agents cisplatin and docetaxel; wherein the cytotoxic or cytostatic activity of the chemotherapeutic agents is adversely affected by either: (i) the overexpression of thioredoxin or glutaredoxin and/or (ii) the thioredoxin-mediated or glutaredoxin-mediated treatment resistance.

In another embodiment, the cancer of origin for treatment with the present invention is selected from any cancer that either: (i) overexpresses thioredoxin or glutaredoxin and/or (ii) exhibits evidence of thioredoxin-mediated or glutaredoxin-mediated treatment resistance to the chemotherapeutic agents or agents already being administered to said patient with cancer.

In another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In one embodiment of the present invention, a method for increasing survival time in a cancer patient with non-small cell lung carcinoma is disclosed, wherein the non-small cell lung carcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with non-small cell lung carcinoma; wherein said method comprises the administration of a medically-sufficient dose of a Formula (I) compound to said patient with non-small cell lung carcinoma either prior to, concomitantly with, or subsequent to the administration of the chemotherapeutic agents cisplatin and docetaxel; wherein the cytotoxic or cytostatic activity of said chemotherapeutic agents is adversely affected by either: (i) the overexpression of thioredoxin or glutaredoxin and/or (ii) the thioredoxin-mediated or glutaredoxin-mediated treatment resistance.

In another embodiment, a method for increasing survival time in a cancer patient with adenocarcinoma is disclosed, wherein the adenocarcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with adenocarcinoma; wherein said method comprises the administration of a medically-sufficient dose of a Formula (I) compound to said patient with adenocarcinoma either prior to, concomitantly with, or subsequent to the administration of the chemotherapeutic agents cisplatin and docetaxel; wherein the cytotoxic or cytostatic activity of said chemotherapeutic agents is adversely affected by either: (i) the overexpression of thioredoxin or glutaredoxin and/or (ii) the thioredoxin-mediated or glutaredoxin-mediated treatment resistance.

In yet another embodiment, the method is comprised of: (i) the administration of docetaxel at a dose of 75 mg/m² which is given intravenously over a period of approximately 1 hour; (ii) the administration of docetaxel in step (i) is immediately followed by the administration of disodium 2,2'-dithio-bis-ethane sulfonate (Tavocept™) at a dose of approximately 40 grams which is given intravenously over a period of approximately 30 minutes; and (iii) the administration of disodium 2,2'-dithio-bis-ethane sulfonate (Tavocept™) in step (ii) is immediately followed by the administration of cisplatin at a dose of 75 mg/m² which is given intravenously over a period of approximately 1 hour with concomitant sufficient intravenous hydration; wherein steps (i)-(iii) constitute a single chemotherapy cycle which can be repeated every two weeks, for up to a total of six cycles.

In another embodiment, a kit comprising a Formula (I) compound for administration, and instructions for administering said Formula (I) compound to a patient with any medical condition or disease wherein there is overexpression of thioredoxin or glutaredoxin is disclosed, wherein said kit comprises the administration of a medically-sufficient dose of a Formula (I) compound, and wherein the overexpression of thioredoxin or glutaredoxin causes deleterious physiological effects in said patient.

In various embodiments of the present, the composition is a Formula (I) compound having the structural formula:

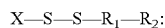

wherein;

$R_1$ is a lower alkylene, wherein $R_1$ is optionally substituted by a member of the group consisting of: lower alkyl, aryl, hydroxy, alkoxy, aryloxy, mercapto, alkylthio or arylthio, for a corresponding hydrogen atom, or

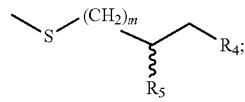

$R_2$ and $R_4$ is sulfonate or phosphonate;
$R_5$ is hydrogen, hydroxy, or sulfhydryl;
m is 0, 1, 2, 3, 4, 5, or 6; and
X is a sulfur-containing amino acid or a peptide consisting of from 2-10 amino acids;
or wherein X is a member of the group consisting of: lower thioalkyl (lower mercapto alkyl), lower alkylsulfonate, lower alkylphosphonate, lower alkenylsulfonate, lower alkyl, lower alkenyl, lower alkynyl, aryl, alkoxy, aryloxy, mercapto, alkylthio or hydroxy for a corresponding hydrogen atom; and
pharmaceutically-acceptable salts, prodrugs, analogs, conjugates, hydrates, solvates, polymorphs, stereoisomers (including diastereoisomers and enantiomers) and tautomers thereof.

In other embodiments of the present invention, the composition is a pharmaceutically-acceptable disodium salt of a Formula (I) compound. In still other embodiments, the composition of the present invention is/are a pharmaceutically-acceptable salt(s) of a Formula (I) compound which include, for example: (i) a monosodium salt; (ii) a sodium potassium salt; (iii) a dipotassium salt; (iv) a calcium salt; (v) a magnesium salt; (vi) a manganese salt; (vii) a monopotassium salt; and (viii) an ammonium salt. It should be noted that mono- and di-potassium salts of 2,2'-dithio-bis-ethane sulfonate and/or an analog thereof are administered to a subject if the total dose of potassium administered at any given point in time is not greater than 100 Meq. and the subject is not hyperkalemic and does not have a condition that would predispose the subject to hyperkalemia (e.g., renal failure).

In embodiments of the present invention, the composition is disodium 2,2'-dithio-bis-ethane sulfonate (also known in the literature as Tavocept™, BNP7787, and dimesna).

In yet other embodiments, the composition is 2-mercapto-ethane sulfonate or 2-mercapto-ethane sulfonate conjugated as a disulfide with a substituent group selected from the group consisting of:
-Cys, -Homocysteine, -Cys-Gly, -Cys-Glu, -Homocysteine, -Homocysteine-Gly, -Homocysteine-Glu, -Cys-Glu,

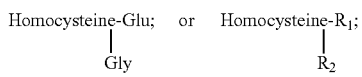

wherein $R_1$ and $R_2$ are any L- or D-amino acids.

In other embodiments, the chemotherapy agent or agents administered are selected from the group consisting of fluropyrimidines; pyrimidine nucleosides; purine nucleosides; anti-folates, platinum agents; anthracyclines/anthracenediones; epipodophyllotoxins; camptothecins; hormones; hormonal complexes; antihormonals; enzymes, proteins, peptides and polyclonal and/or monoclonal antibodies; vinca alkaloids; taxanes; epothilones; antimicrotubule agents; alkylating agents; antimetabolites; topoisomerase inhibitors; aziridine-containing compounds; antivirals; and various other cytotoxic and cytostatic agents.

In embodiments of the present invention, the chemotherapy agent or agents are selected from the group consisting of: cisplatin, carboplatin, oxaliplatin, satraplatin, picoplatin, tetraplatin, platinum-DACH, and analogs and derivatives thereof.

In other embodiments, the chemotherapy agent or agents are selected from the group consisting of: docetaxel, paclitaxel, polyglutamylated forms of paclitaxel, liposomal paclitaxel, and analogs and derivatives thereof.

In yet other embodiments of the present invention, the chemotherapy agents are docetaxel and cisplatin.

Furthermore, in brief, the present invention discloses and claims: (i) compositions, methods, and kits which lead to an increase in patient survival time in cancer patients receiving chemotherapy; (ii) compositions and methods which cause cytotoxic or apoptotic potentiation of the anti-cancer activity of chemotherapeutic agents; (iii) compositions and methods for maintaining or stimulating hematological function in patients in need thereof, including those patients suffering from cancer; (iv) compositions and methods for maintaining or stimulating erythropoietin function or synthesis in patients in need thereof, including those patients suffering from cancer; (v) compositions and methods for mitigating or preventing anemia in patients in need thereof, including those patients suffering from cancer; (vi) compositions and methods for maintaining or stimulating pluripotent, multipotent, and unipotent normal stem cell function or synthesis in patients in need thereof, including those patients suffering from cancer; (vii) compositions and methods which promote the arrest or retardation of tumor progression in cancer patients receiving chemotherapy; (viii) compositions and methods for increasing patient survival and/or delaying tumor progression while maintaining or improving the quality of life in a cancer patient receiving chemotherapy; (ix) novel methods of the administration of taxane and platinum medicaments and a Formula (I) compound of the present invention to a cancer patient; and (x) kits to achieve one or more of the aforementioned physiological effects in a patient in need thereof, including those patients suffering from cancer.

In one embodiment, a patient suffering from lung cancer treated with taxane and/or platinum medicaments is given a medically sufficient dosage of a Formula (I) compound so as to increase patient survival time in said patient suffering from lung cancer.

In another embodiment, the lung cancer is non-small cell lung carcinoma.

In another embodiment, the increase in patient survival time in said patient suffering from lung cancer and treated with a Formula (I) compound is expected to be at least 30 days longer than the expected survival time if said patient was not treated with a Formula (I) compound.

In yet another embodiment, a patient suffering from lung cancer was treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, a patient suffering from lung cancer was treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, a patient suffering from adenocarcinoma treated with taxane and/or platinum medicaments is given a medically sufficient dosage of a Formula (I) compound so as to increase patient survival time in said patient suffering from adenocarcinoma.

In another embodiment, the increase in patient survival time in said patient suffering from adenocarcinoma and treated with a Formula (I) compound is expected to be at least 30 days longer than the expected survival time if said patient was not treated with a Formula (I) compound.

In yet another embodiment, a patient suffering from adenocarcinoma is treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, a patient suffering from adenocarcinoma is treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, a patient suffering from lung cancer treated with taxane and platinum medicaments is given a medically sufficient dosage of a Formula (I) compound so as to potentiate the chemotherapeutic effect in said patient suffering from lung cancer.

In another embodiment, the lung cancer is non-small cell lung carcinoma.

In yet another embodiment, the chemotherapeutic effect is potentiated in a patient suffering from lung cancer treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, the chemotherapeutic effect is potentiated in a patient suffering from lung cancer treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, the chemotherapeutic effect is potentiated in a patient suffering from adenocarcinoma who is treated with taxane and platinum medicaments and is also given a medically sufficient dosage of a Formula (I) compound so as to increase patient survival time in said patient suffering from adenocarcinoma.

In yet another embodiment, the chemotherapeutic effect is potentiated in a patient suffering from adenocarcinoma treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, the chemotherapeutic effect is potentiated in a patient suffering from adenocarcinoma treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, hematological function is maintained or stimulated in a patient in need thereof, by providing to said patient a composition comprised of a Formula (I) compound in a medically sufficient dosage.

In one embodiment, a patient suffering from lung cancer treated with taxane and/or platinum medicaments is given a medically sufficient dosage of a Formula (I) compound so as to maintain or stimulate hematological function in said patient suffering from lung cancer.

In another embodiment, the lung cancer is non-small cell lung carcinoma.

In yet another embodiment, the hematological function is maintained or stimulated in a patient suffering from lung cancer treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, the hematological function is maintained or stimulated in a patient suffering from lung cancer treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, the hematological function is maintained or stimulated in a patient suffering from adenocarcinoma who is treated with taxane and/or platinum medicaments and is also given a medically sufficient dosage of a Formula (I) compound so as to maintain or stimulate hematological function in said patient suffering from adenocarcinoma.

In yet another embodiment, the hematological function is maintained or stimulated in a patient suffering from adenocarcinoma treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, the hematological function is maintained or stimulated in a patient suffering from adenocarcinoma treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, erythropoietin function or synthesis or homeostatic function of erythropoiesis is maintained or stimulated in a patient in need thereof, by providing to said patient a composition comprised of a Formula (I) compound in a medically sufficient dosage.

In one embodiment, a patient suffering from lung cancer treated with taxane and/or platinum medicaments is given a medically sufficient dosage of a Formula (I) compound so as to maintain or stimulate erythropoietin function or synthesis or homeostatic function of erythropoiesis in said patient suffering from lung cancer.

In another embodiment, the lung cancer is non-small cell lung carcinoma.

In yet another embodiment, the erythropoietin function or synthesis or homeostatic function of erythropoiesis is maintained or stimulated in a patient suffering from lung cancer treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, the erythropoietin function or synthesis or homeostatic function of erythropoiesis is maintained or stimulated in a patient suffering from lung cancer treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, the erythropoietin function or synthesis or homeostatic function of erythropoiesis is maintained or stimulated in a patient suffering from adenocarcinoma who is treated with taxane and/or platinum medicaments and is also given a medically sufficient dosage of a Formula (I) compound so as to maintain or stimulate erythropoietin function or synthesis or homeostatic function of erythropoiesis in said patient suffering from adenocarcinoma.

In yet another embodiment, the erythropoietin function or synthesis or homeostatic function of erythropoiesis is maintained or stimulated in a patient suffering from adenocarcinoma treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, the erythropoietin function or synthesis or homeostatic function of erythropoiesis is maintained or stimulated in a patient suffering from adenocarcinoma treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, anemia is mitigated or prevented in a patient in need thereof, by providing to said patient a composition comprised of a Formula (I) compound in a medically sufficient dosage.

In one embodiment, a patient suffering from lung cancer treated with taxane and/or platinum medicaments is given a medically sufficient dosage of a Formula (I) compound so as to mitigate or prevent chemotherapy-induced anemia in said patient suffering from lung cancer.

In another embodiment, the lung cancer is non-small cell lung carcinoma.

In yet another embodiment, chemotherapy-induced anemia is mitigated or prevented in a patient suffering from lung cancer treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, chemotherapy-induced anemia is mitigated or prevented in a patient suffering from lung cancer treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, chemotherapy-induced anemia is mitigated or prevented in a patient suffering from adenocarcinoma who is treated with taxane and/or platinum medicaments and is also given a medically sufficient dosage of a Formula (I) compound so as to mitigate or prevent chemotherapy-induced anemia.

In yet another embodiment, chemotherapy-induced anemia is mitigated or prevented in a patient suffering from adenocarcinoma treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, chemotherapy-induced anemia is mitigated or prevented in a patient suffering from adenocarcinoma treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, pluripotent, multipotent, and unipotent normal stem cell function or synthesis is maintained or stimulated in a patient in need thereof, by providing to said patient a composition comprised of a Formula (I) compound in a medically sufficient dosage.

In one embodiment, a patient suffering from lung cancer treated with taxane and/or platinum medicaments is given a medically sufficient dosage of a Formula (I) compound so as to maintain or stimulate pluripotent, multipotent, and unipotent normal stem cell function or synthesis in said patient suffering from lung cancer.

In another embodiment, the lung cancer is non-small cell lung carcinoma.

In yet another embodiment, pluripotent, multipotent, and unipotent normal stem cell function or synthesis is maintained or stimulated in a patient suffering from lung cancer treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, pluripotent, multipotent, and unipotent normal stem cell function or synthesis is maintained or stimulated in a patient suffering from lung cancer treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, pluripotent, multipotent, and unipotent normal stem cell function or synthesis is maintained or stimulated in a patient suffering from adenocarcinoma who is treated with taxane and/or platinum medicaments and is also given a medically sufficient dosage of a Formula (I) compound so as to maintain or stimulate pluripotent, multipotent, and unipotent normal stem cell function or synthesis in said patient suffering from adenocarcinoma.

In yet another embodiment, pluripotent, multipotent, and unipotent normal stem cell function or synthesis is maintained or stimulated in a patient suffering from adenocarcinoma treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, pluripotent, multipotent, and unipotent normal stem cell function or synthesis is maintained or stimulated in a patient suffering from adenocarcinoma treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In another embodiment, the Formula (I) compounds increase patient survival and/or delay tumor progression while maintaining or improving the quality of life of said patients diagnosed with lung cancer who are being treated with the taxane and/or platinum medicaments of the present invention.

In another embodiment, the lung cancer is non-small cell lung carcinoma.

In another embodiment, the Formula (I) compounds increase patient survival and/or delay tumor progression while maintaining or improving the quality of life of said patients diagnosed with adenocarcinoma who are being treated with the taxane and/or platinum medicaments of the present invention.

In another embodiment, the patients suffering from adenocarcinoma were male or female and smokers or non-smokers.

In another embodiment, the platinum medicaments of the present invention include cisplatin, oxaliplatin, carboplatin, satraplatin, and derivatives and analogs thereof.

In another embodiment, the taxane medicament is selected from the group consisting of docetaxel, paclitaxel, paclitaxel derivatives, polyglutamylated forms of paclitaxel, liposomal paclitaxel, and derivatives and analogs thereof.

In still another embodiment, the compositions of Formula (I) include 2,2'-dithio-bis-ethane sulfonate, a pharmaceutically-acceptable salt thereof, and/or an analog thereof, as well as prodrugs, analogs, conjugates, hydrates, solvates and polymorphs, as well as stereoisomers (including diastereoisomers and enantiomers) and tautomers of such compounds.

In still another embodiment, the dose rate of the taxane and platinum medicaments ranged from approximately 10-20 mg/m$^2$/day and the dose rate of a Formula (I) compound ranged from approximately 4.1-41.0 g/m$^2$ per day; the concentration of the taxane and platinum medicaments and/or Formula (I) compounds is at least 0.01 mg/mL; the infusion time of the taxane and platinum medicaments and/or Formula (I) compounds is from approximately 5 minutes to approximately 24 hours, and can be repeated as needed and tolerated in a given patient; the schedule of administration of the taxane and platinum medicaments and/or Formula (I) compounds is every 2-8 weeks.

In another embodiment, a kit comprising a Formula (I) compound for administration to a patient, and instructions for administering said Formula (I) compound in an amount sufficient to cause one or more of the physiological effects selected from the group consisting of: increasing patient survival time of said cancer patient receiving taxane and/or platinum medicaments; causing a cytotoxic or apoptotic potentiation of the chemotherapeutic effects of said taxane and platinum medicaments; maintaining or stimulating hematological function in said patient, including said patient with cancer receiving chemotherapy; maintaining or stimulating erythropoietin function or synthesis in said patient, including said patient with cancer receiving chemotherapy; mitigating or preventing anemia in said patient, including said patient with cancer receiving chemotherapy; maintaining or stimulating pluripotent, multipotent, and unipotent normal stem cell function or synthesis in said patient, including said patient with cancer receiving chemotherapy; promoting the arrest or retardation of tumor progression in said cancer patient receiving taxane and platinum medicaments; and/or increasing patient survival and/or delaying tumor progression while maintaining or improving the quality of life in said cancer patient receiving taxane and platinum medicaments.

In another embodiment, the cancer patient has lung cancer.

In yet another embodiment, the lung cancer is non-small cell lung cancer.

In still another embodiment, the cancer patient has an adenocarcinoma.

In one embodiment, the kit further contains instructions for administering a taxane medicament and a platinum medicament selected from the group consisting of cisplatin, oxaliplatin, carboplatin, satraplatin, and derivatives and analogs thereof.

In another embodiment, the kit further contains instructions for administering a platinum medicament and a taxane medicament selected from the group consisting of docetaxel, paclitaxel, polyglutamylated forms of paclitaxel, liposomal paclitaxel, and derivatives and analogs thereof.

In yet another embodiment, the platinum and taxane medicaments are cisplatin and paclitaxel.

DESCRIPTION OF THE FIGURES

FIG. 5 illustrates, in tabular form, the Primary Endpoint (i.e., the mitigation or prevention of patient peripheral neuropathy) of the Japan Phase III Clinical Trial, as determined utilizing the Peripheral Neuropathy Questionnaire (PNQ©).

FIG. 6 illustrates, in tabular form, an evaluation of the statistical power observed in the Japan Phase III Clinical Trial with respect to the Primary Endpoint (i.e., the mitigation or prevention of patient peripheral neuropathy), as measured by the Generalized Estimating Equation (GEE) method.

FIG. 7 illustrates, in tabular form, a Secondary Endpoint (i.e., a decrease in patient hemoglobin, erythrocyte, and hematocrit levels) of the Japan Phase III Clinical Trial, in patient populations receiving Tavocept™ (BNP7787) or placebo.

FIG. 8 illustrates, in tabular form, a Secondary Endpoint (i.e., tumor response rate to chemotherapy administration) of the Japan Phase III Clinical Trial, in patient populations receiving either Tavocept™ (BNP7787) or placebo, as measured by the physician or by the Independent Radiological Committee (IRC) criteria.

FIG. 13 illustrates, in tabular form, patient overall survival (OS) and patient progression-free survival (PFS) in the U.S. Phase II NSCLC Clinical Trial, in patient populations diagnosed with non-small cell lung carcinoma receiving chemotherapy with either Tavocept™ (BNP7787) or no Tavocept™ treatment.

FIG. 15 illustrates, in tabular form, the number of patients experiencing Grade 3 and Grade 4 treatment-related adverse events in the U.S. Phase II NSCLC Phase II Clinical Trial, in patient populations diagnosed with non-small cell lung carcinoma receiving chemotherapy with either Tavocept™ (BNP7787) or no Tavocept™ treatment.

DETAILED DESCRIPTION OF THE INVENTION

Figure 1:
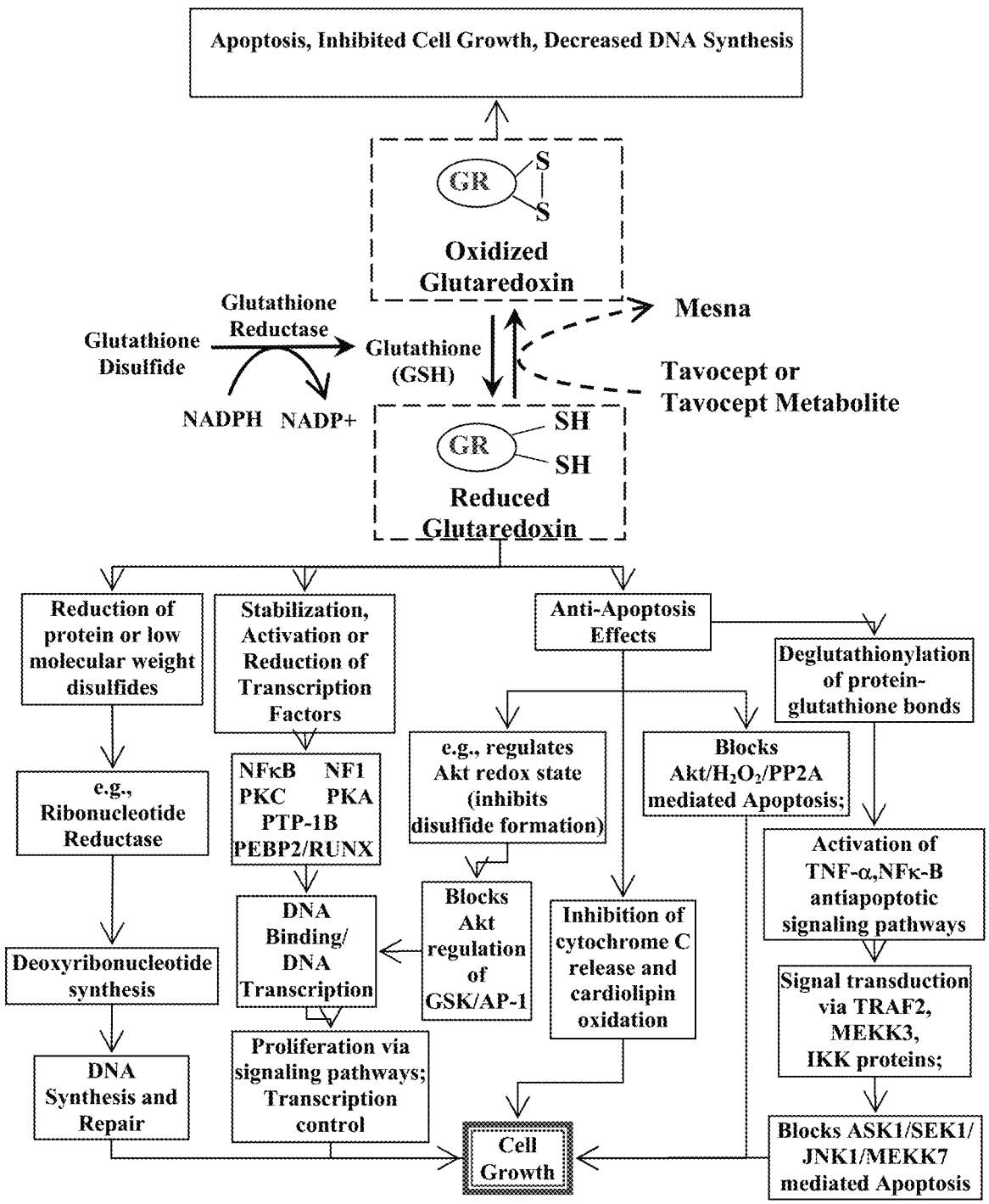
FIG. 1 illustrates the involvement of (reduced) glutaredoxin in promoting cell growth and/or stimulating cell proliferation via several metabolic pathways. The glutaredoxin system consists of glutaredoxin, glutathione and glutathione reductase. It should be noted, however, that glutaredoxin is also involved in many other intracellular pathways.

The descriptions and embodiments set forth herein are not intended to be exhaustive, nor do they limit the present invention to the precise forms disclosed. They are included to illustrate the principles of the invention, and its application and practical use by those skilled in the art.

Definitions

As utilized herein, the term "generic structural formula" refers to the fixed structural part of the molecule of the formula given.

As utilized herein, the term "nucleophile" means an ion or molecule that donates a pair of electrons to an atomic nucleus to form a covalent bond; the nucleus that accepts the electrons is called an electrophile. This occurs, for example, in the formation of acids and bases according to the Lewis concept, as well as in covalent carbon bonding in organic compounds.

As utilized herein the terms "fragments", "moieties" or "substituent groups" are the variable parts of the molecule, designated in the formula by variable symbols, such as $R_x$, X or other symbols. Substituent Groups may consist of one or more of the following:

"$C_x$-$C_y$ alkyl" generally means a straight or branched-chain aliphatic hydrocarbon containing as few as x and as many as y carbon atoms. Examples include "$C_1$-$C_6$ alkyl", particularly "$C_1$-$C_4$ alkyl" (also referred to as "lower alkyl"), which includes a straight or branched chain hydrocarbon with no more than 6 total carbon atoms, and $C_1$-$C_{16}$ alkyl, which includes a hydrocarbon with as few as one up to as many as sixteen total carbon atoms, and the like. In the present application, the term "alkyl" is defined as comprising a straight or branched chain hydrocarbon of between 1 and 20 atoms, which can be saturated or unsaturated, and may include heteroatoms such as nitrogen, sulfur, and oxygen;

"$C_x$-$C_y$ alkylene" means a bridging moiety formed of as few as "x" and as many as "y" —$CH_2$— groups. In the present invention, the term "alkylene" or "lower alkylene" is defined as comprising a bridging hydrocarbon having from 1 to 6 total carbon atoms which is bonded at its terminal carbons to two other atoms (—$CH_2$—)$_x$ where x is 1 to 6;

"$C_x$-$C_y$ alkenyl or alkynyl" means a straight or branched chain hydrocarbon with at least one double bond (alkenyl) or triple bond (alkynyl) between two of the carbon atoms;

"Halogen" or "Halo" means chloro, fluoro, bromo or iodo;

"$C_x$-$C_y$ Cycloalkyl" means a hydrocarbon ring or ring system consisting of one or more rings, fused or unfused, wherein at least one of the ring bonds is completely saturated, with the ring(s) having from x to y total carbon atoms;

"Acyl" means —C(O)—R, where R is hydrogen, $C_x$-$C_y$ alkyl, aryl, $C_x$-$C_y$ alkenyl, $C_x$-$C_y$ alkynyl, and the like;

"Acyloxy" means —O—C(O)—R, where R is hydrogen, $C_x$-$C_y$ alkyl, aryl, and the like;

"Aryl" generally means an aromatic ring or ring system consisting of one or more rings, preferably one to three rings, fused or unfused, with the ring atoms consisting entirely of carbon atoms. In the present invention, the term "aryl" is defined as comprising an aromatic ring system, either fused or unfused, preferably from one to three total rings, with the ring elements consisting entirely of 5-8 carbon atoms;

"Arylalkyl" means an aryl moiety as defined above, bonded to the scaffold through an alkyl moiety (the attachment chain);

"Arylalkenyl" and "Arylalkynyl" mean the same as "Arylalkyl", but including one or more double or triple bonds in the attachment chain;

"Amine" means a class of organic complexes of nitrogen that may be considered as derived from ammonia ($NH_3$) by replacing one or more of the hydrogen atoms with alkyl groups. The amine is primary, secondary or tertiary, depending upon whether one, two or three of the hydrogen atoms are replaced. A "short chain anime" is one in which the alkyl group contains from 1 to 10 carbon atoms;

"Ammine" means a coordination analog formed by the union of ammonia with a metallic substance in such a way that the nitrogen atoms are linked directly to the metal. It should be noted the difference from amines, in which the nitrogen is attached directly to the carbon atom;

"Azide" means any group of complexes having the characteristic formula R($N_3$)x. R may be almost any metal atom, a hydrogen atom, a halogen atom, the ammonium radical, a complex [CO($NH_3$)$_6$], [Hg(CN)$_2$M], (with M=Cu, Zn, Co, Ni) an organic radical like methyl, phenyl, nitrophenol, dinitrophenol, p-nitrobenzyl, ethyl nitrate, and the like. The azide group possesses a chain structure rather than a ring structure;

"Imine" means a class of nitrogen-containing complexes possessing a carbon-to-nitrogen double bond (i.e., R—CH=NH);

"Heterocycle" means a cyclic moiety of one or more rings, preferably one to three rings, fused or unfused, wherein at least one atom of one of the rings is a non-carbon atom. Preferred heteroatoms include oxygen, nitrogen and sulfur, or any combination of two or more of those atoms. The term "Heterocycle" includes furanyl, pyranyl, thionyl, pyrrolyl, pyrrolidinyl, prolinyl, pyridinyl, pyrazolyl, imidazolyl, triazolyl, tetrazolyl, oxathiazolyl, dithiolyl, oxazolyl, isoxazolyl, oxadiazolyl, pyridazinyl, pyrimidinyl, pyrazinyl, piperazinyl, oxazinyl, thiazolyl, and the like; and "Substituted" modifies the identified fragments (moieties) by replacing any, some or all of the hydrogen atoms with a moiety (moieties) as identified in the specification. Substitutions for hydrogen atoms to form substituted complexes include halo, alkyl, nitro, amino (also N-substituted, and N,N di-substituted amino), sulfonyl, hydroxy, alkoxy, phenyl, phenoxy, benzyl, benzoxy, benzoyl, and trifluoromethyl.

As utilized herein, the definitions for the terms "adverse event" (effect or experience), "adverse reaction", and unexpected adverse reaction have previously been agreed to by consensus of the more than thirty Collaborating Centers of the WHO International Drug Monitoring Centre (Uppsala, Sweden). See, Edwards, I. R., et al., Harmonisation in Pharmacovigilance *Drug Safety* 10(2):93-102 (1994). The following definitions, with input from the WHO Collaborative Centre, have been agreed to:

1. Adverse Event (Adverse Effect or Adverse Experience)—Any untoward medical occurrence in a patient or clinical investigation subject administered a pharmaceutical product and which does not necessarily have to have a causal relationship with this treatment. An Adverse Event (AE) can therefore be any unfavorable and unintended sign (including an abnormal laboratory finding, for example), symptom, or disease temporally associated with the use of a medicinal product, whether or not considered related to the medicinal product.

2. Adverse Drug Reaction (ADR)—In the pre-approval clinical experience with a new medicinal product or its new usages, particularly as the therapeutic dose(s) may not be established: all noxious and unintended responses to a medicinal product related to any dose should be considered adverse drug reactions. Drug-related Adverse Events are rated from grade 1 to grade 5 and relate to the severity or intensity of the event. Grade 1 is mild, grade 2 is moderate, grade 3 is severe, grade 4 is life threatening, and grade 5 results in death.

3. Unexpected Adverse Drug Reaction—An adverse reaction, the nature or severity of which is not consistent with the applicable product information.

Serious Adverse Event or Adverse Drug Reaction: A Serious Adverse Event (experience or reaction) is any untoward medical occurrence that at any dose:

(a) Results in death or is life-threatening. It should be noted that the term "life-threatening" in the definition of "serious" refers to an event in which the patient was at risk of death at the time of the event; it does not refer to an event which hypothetically might have caused death if it were more severe.

(b) Requires inpatient hospitalization or prolongation of existing hospitalization.

(c) Results in persistent or significant disability/incapacity, or (d) Is a congenital anomaly/birth defect.

As utilized herein the term "cancer" refers to all known forms of cancer including, solid forms of cancer (e.g., tumors), lymphomas, and leukemias.

As utilized herein, the term "clinical trial" or "trial", refers to:

(i) the Japan Phase III Clinical Trial disclosed in the present invention which was utilized to show the ability of Tavocept™ (also referred to in the literature as disodium 2,2'-dithio-bis-ethane sulfonate, dimesna, or BNP7787) to prevent and/or reduce peripheral neuropathy induced by paclitaxel/cisplatin combination therapy. The incidence and severity of adverse reactions, time to their onset, etc. and the like, were compared between patients treated with Tavocept™ and those given a placebo using Quality of Life (QOL) questionnaires (i.e., Peripheral Neuropathy Questionnaire (PNQ©) and CIPN-20)) and the National Cancer Institute—Common Toxicity Criteria (NCI-CTC). The effects of Tavocept™ on the Quality of Life (QOL) of patients under anticancer treatment were also evaluated using the QOL questionnaire, EORTC QLQ-C30. Whether or not Tavocept™ would affect the efficacy of paclitaxel/cisplatin combination therapy was also evaluated based on the response rate, aggravation-free survival period, and total survival period. In order to make all these evaluations, Tavocept™ (approximately 14-22 $g/m^2$, most preferably approximately 18.4 $g/m^2$) or placebo (0.9% NaCl) was administered to non-small cell lung carcinoma (NSCLC) patients, including adenocarcinoma patients, under chemotherapy with paclitaxel (approximately 160-190 $mg/m^2$, most preferably approximately 175 $mg/m^2$) and cisplatin (approximately 60-100 $mg/m^2$, most preferably approximately 80 $mg/m^2$), every 3 weeks (and repeated for a minimum of 2 cycles); and/or (ii) the United States (U.S.) Phase II non-small cell lung carcinoma (NSCLC) Clinical Study disclosed in the present invention was used to ascertain the effect of a dose-dense administration of docetaxel and cisplatin every two weeks with concomitant administration of pegfilgrastim and darbepoetin alfa with and without administration of Tavocept™ (also referred to in the literature as disodium 2,2'-dithio-bis-ethane sulfonate, dimesna, or BNP7787) in patients with advanced stage (IIIB/IV) non-small cell lung carcinoma (NSCLC), including adenocarcinoma patients. Whether or not Tavocept™ would affect the efficacy of the dose-dense docetaxel/cisplatin combination therapy was also evaluated based on the response rate, aggravation-free survival period, and total survival period. In order to make all these evaluations, in the Tavocept™ arm of the clinical study, docetaxel administration (75 $mg/m^2$; i.v. administration over a period of 1 hour on day one of the chemotherapy cycle) was immediately followed by the administration of Tavocept™ (40 g; i.v. administration over a period of 30 minutes). The Tavocept™ administration was then immediately followed by the administration of cisplatin (75 $mg/m^2$; i.v. administration over a period of 1 hour) with adequate hydration. Darbepoetin alfa (200 µg; subcutaneous administration) was administered on day one of the chemotherapy cycle and pegfilgrastim (6 mg subcutaneous administration) was administered on day two of the chemotherapy cycle if the patient's hemoglobin levels were ≤11 g/dL. The aforementioned chemotherapy cycle was repeated every two weeks, for up to a total of six cycles. The other, non-Tavocept™ administration arm of the study was identical to the previously discussed Tavocept™ arm, with the exception that the docetaxel administration was immediately followed by cisplatin administration without an intermediate administration of Tavocept™. In addition, the incidence and severity of adverse reactions were also compared between patients in the Tavocept™ and non-Tavocept™ arms of the study using the National Cancer Institute-Common Toxicity Criteria (NCI-CTC) questionnaire.

As utilized herein, the term "adenocarcinoma" refers to a cancer that originates in glandular tissue. Glandular tissue comprises organs that synthesize a substance for release such as hormones. Glands can be divided into two general groups: (i) endocrine glands—glands that secrete their product directly onto a surface rather than through a duct, often into the blood stream and (ii) exocrine glands—glands that secrete their products via a duct, often into cavities inside the body or its outer surface. However, it should be noted that to be classified as adenocarcinoma, the tissues or cells do not necessarily need to be part of a gland, as long as they have secretory properties. Adenocarcinoma may be derived from various tissues including, but not limited to, breast, colon, lung, prostate, salivary gland, stomach, liver, gall bladder, pancreas (99% of pancreatic cancers are ductal adenocarcinomas), cervix, vagina, and uterus, as well as unknown primary adenocarcinomas. Adenocarcinoma is a neoplasm which frequently presents marked difficulty in differentiating from where and from which type of glandular tissue the tumor(s) arose. Thus, an adenocarcinoma identified in the lung may have had its origins (or may have metastasized) from an ovarian adenocarcinoma. Cancer for which a primary site cannot be found is called cancer of unknown primary.

As utilized herein, the term "non-small cell lung cancer (NSCLC)" accounts for approximately 75% of all primary lung cancers. NSCLC is pathologically characterized further into adenocarcinoma, squamous cell carcinoma, large cell carcinoma, and various other less common forms.

As utilized herein, the terms "chemotherapy" or "chemotherapeutic regimen(s)" or "chemotherapy cycle" refer to treatment using the above-mentioned chemotherapeutic agents with or without the use of an oxidative metabolism-affecting Formula (I) compound of the present invention.

As used herein, the term "potentiate", "potentiating", "chemotherapy potentiating", "chemotherapeutic effect is potentiated", and "potentiating the chemotherapeutic effects" is defined herein as producing one or more of the following physiological effects: (i) the increase or enhancement of the cytotoxic or cytostatic activity of chemotherapy agents by acting in an additive or synergistic cytotoxic manner with said chemotherapeutic agents within the tumor cells; (ii) reducing, preventing, mitigating, and/or delaying said deleterious physiological manifestations of said cancer in subjects suffering therewith; (iii) selectively sensitizing cancer cells to the anti-cancer activity of chemotherapeutic agents; and/or (iv) restoring apoptotic effects or sensitivity in tumor cells.

As used herein, the term "chemotherapeutic agent" or "chemotherapy agent" or "chemotherapeutic drug" refer to an agent that reduces, prevents, mitigates, limits, and/or delays the growth of metastases or neoplasms, or kills neoplastic cells directly by necrosis or apoptosis of neoplasms or any other mechanism, or that can be otherwise used, in a pharmaceutically-effective amount, to reduce, prevent, mitigate, limit, and/or delay the growth of metastases or neoplasms in a subject with neoplastic disease. Chemotherapeutic agents include, for example, fluropyrimidines; pyrimidine nucleosides; purine nucleosides; antifolates, platinum agents; anthracyclines/anthracenediones; epipodophyllotoxins; camptothecins; hormones; hormonal complexes; antihormonals; enzymes, proteins, peptides and polyclonal and/or monoclonal antibodies; vinca alkaloids;

taxanes; epothilones; antimicrotubule agents; alkylating agents; antimetabolites; topoisomerase inhibitors; aziridine-containing compounds; antivirals; and various other cytotoxic and cytostatic agents.

As utilized herein, the terms "chemotherapy", "chemotherapeutic regimen(s)", or "chemotherapy cycle" refer to treatment using the above-mentioned chemotherapeutic agents with or without the Formula (I) compounds of the present invention.

As utilized herein, the term "chemotherapeutic effect" refers to the ability of an agent to reduce, prevent, mitigate, limit, and/or delay the growth of metastases or neoplasms, or kill neoplastic cells directly by necrosis or apoptosis of neoplasms or any other mechanism, or that can be otherwise used to reduce, prevent, mitigate, limit, and/or delay the growth of metastases or neoplasms in a subject with neoplastic disease.

As utilized herein, the term "cycle" refers to the administration of a complete regimen of medicaments to the patient in need thereof in a defined time period. By way of non-limiting example, in the Japan Phase III Clinical Trial disclosed herein, a cycle would comprise the administration of taxane and platinum medicaments, an oxidative metabolism-affecting Formula (I) compound, and any associated medications which may be required (e.g., pre-hydration, anti-emesis drugs, and the like) to the patient within a defined time period.

As used herein, the term "cytostatic agents" are mechanism-based agents that slow the progression of neoplastic disease and include drugs, biological agents, and radiation.

As used herein the term "cytotoxic agents" are any agents or processes that kill neoplastic cells and include drugs, biological agents, and radiation. In addition, the term "cytotoxic" is inclusive of the term "cytostatic".

As used herein, the term "platinum medicaments" or "platinum compounds" include all compounds, compositions, and formulations which contain a platinum ligand in the structure of the molecule. By way of non-limiting example, the valence of the platinum ligand contained therein may be platinum II or platinum IV. The platinum medicaments or platinum compounds of the present invention include, in a non-limiting manner, cisplatin, oxaliplatin, carboplatin, satraplatin, and analogs and derivatives thereof.

As used herein, the term "taxane medicaments" include, in a non-limiting manner, docetaxel or paclitaxel (including the commercially-available paclitaxel derivatives Taxol® and Abraxane®), polyglutamylated forms of paclitaxel (e.g., Xyotax®), liposomal paclitaxel (e.g., Tocosol®), and analogs and derivatives thereof.

As utilized herein, the term "colony-stimulating factor" (CSF) are secreted glycoproteins which bind to receptor proteins on the surfaces of hematopoietic stem cells and thereby activate intracellular signaling pathways which can cause the cells to proliferate and differentiate into a specific kind of blood cell (usually white blood cells). Hematopoietic stem cells (HSC) are stem cells (i.e., cells retain the ability to renew themselves through mitotic cell division and can differentiate into a diverse range of specialized cell types) that give rise to all the blood cell types including myeloid (e.g., monocytes, macrophages, neutrophils, basophils, eosinophils, erythrocytes, megakaryocytes/platelets, dendritic cells, and the like) and lymphoid lineages (e.g., T-cells, B-cells, NK-cells, and the like). Colony-stimulating factors include: macrophage colony-stimulating factor (CSF-1); granulocyte-macrophage colony-stimulating factor (CSF-2); and granulocyte colony-stimulating factor (GCSF or CSF-3).

As used herein the term "erythropoiesis" refers to the process by which red blood cells (erythrocytes) are produced. In the early fetus, erythropoiesis takes place in the mesodermal cells of the yolk sac. By the third or fourth month of fetal development, erythropoiesis moves to the spleen and liver. In human adults, erythropoiesis generally occurs within the bone marrow. The long bones of the arm (tibia) and leg (femur) cease to be important sites of hematopoiesis by approximately age 25; with the vertebrae, sternum, pelvis, and cranial bones continuing to produce red blood cells throughout life. However, it should be noted that in humans with certain diseases and in some animals, erythropoiesis also occurs outside the bone marrow, within the spleen or liver. This is termed extramedullary erythropoiesis. In the process of red blood cell maturation, a cell undergoes a series of differentiations. The following stages of development all occur within the bone marrow: (i) pluripotent hematopoietic stem cell; (ii) multipotent stem cell; (iii) unipotent stem cell; (iv) pronormoblast; (v) basophilic normoblast/early normoblast; (vi) polychrmatophilic normoblast/intermediate normoblast; (vii) orthochromic normoblast/late normoblast; and (viii) reticulocyte. Following these stages, the cell is released from the bone marrow, and ultimately becomes an "erythrocyte" or mature red blood cell circulating in the peripheral blood.

As used herein, the term "erythropoietin" is a glycoprotein hormone that is a cytokine for erythrocyte (red blood cell) precursors in the bone marrow which regulates the process of red blood cell production (i.e., erythropoiesis). Erythropoietin (EPO) is produced mainly by peritubular fibroblasts of the renal cortex. Regulation is believed to rely on a feed-back mechanism measuring blood oxygenation. Constitutively synthesized transcription factors for EPO, known as hypoxia inducible factors (HIFs), are hydroxylized and proteosomally-digested in the presence of oxygen.

As used herein, the term "darbepoetin alfa" is an synthetic form of erythropoietin. It is an erythropoiesis stimulating (i.e., increases red blood cell levels) protein, comprised of 165-amino acid residues, and is used to treat anemia, commonly associated with chronic renal failure and cancer chemotherapy. Darbepoetin is marketed by Amgen under the trade name Aranesp. It is produced by recombinant DNA technology in modified Chinese hamster ovary cells. It differs from endogenous erythropoietin by containing two more N-linked oligosaccharide chains.

As utilized herein, the term "pegfilgrastim" is an immunostimulator which functions as a pegylated granulocyte colony-stimulating factor (GCSF). Amgen manufactures pegfilgrastim under the brand name Neulasta. GCSF is a colony-stimulating factor hormone. It is a glycoprotein, growth factor or cytokine produced by endothelium, macrophages, and a number of other immune cells, which stimulates the bone marrow to produce granulocytes and stem cells. GCSF then stimulates the bone marrow to release them into the blood. It also stimulates the survival, proliferation, differentiation, and function of neutrophil precursors and mature neutrophils. GCSF is also known as colony-stimulating factor 3 (CSF 3). The natural human glycoprotein exists in two forms; a 174- and 180-amino acid residue protein with a molecular weight of 19.6 kDa. The more-abundant and more-active 174 amino acid residue form has been used in the development of pharmaceutical products by recombinant DNA (rDNA) technology. Pegylation is the process of covalent attachment of polyethylene glycol (PEG) polymer chains to another molecule, normally a drug or therapeutic protein. Pegylation is routinely achieved by incubation of a reactive derivative of PEG with the target macromolecule. The covalent attachment of PEG to a drug or therapeutic protein can facilitate the "masking" of the agent from the host's immune system (i.e., causing reduced immunogenicity and antigenicity) and increase the hydrodynamic size (i.e., size in solution) of the agent which prolongs its circulatory time by reducing renal clearance. Pegylation can also provide water solubility to hydrophobic drugs and proteins.

As used herein, the term "evidence of" as it applies to the exhibition of thioredoxin-mediated or glutaredoxin-mediated treatment resistance in the present invention means that it is probable or likely that thioredoxin-mediated or glutaredoxin-mediated treatment resistance has occurred or will occur. It is described in that manner due to the fact that it is neither expected, nor possible to prove with 100% certainty that the cancer cells exhibit thioredoxin-mediated or glutaredoxin-mediated treatment resistance, prior to the actual treatment of the patient. By way of non-limiting example, the current use of, e.g., florescence in situ hybridization (FISH) or immunohistochemistry (IHC) to guide treatment decisions for HER2/neu-based therapy are predicated upon the probability of the overexpression/increased concentrations of HER2/neu being correlated with the probability of a therapeutic response. Such expectation of a therapeutic response is not 100% certain, and is related to many factors, not the least of which is the diagnostic accuracy of the test utilized which, in turn, is also limited by the sampling of the tumor and various other factors (e.g., laboratory methodology/technique, reagent quality, and the like).

As used herein, the terms "Formula (I) compound" or "Formula (I) composition" include all molecules, unless specifically identified otherwise, that share substantial structural and/or functional characteristics with the 2,2'-dithio-bis-ethane sulfonate parent compound and includes the compounds of Formula (I) which refers to compounds possessing the generic structural formula:

X—S—S—$R_1$—$R_2$:

wherein;
$R_1$ is a lower alkylene, wherein $R_1$ is optionally substituted by a member of the group comprising: lower alkyl, aryl, hydroxy, alkoxy, aryloxy, mercapto, alkylthio or arylthio, for a corresponding hydrogen atom, or

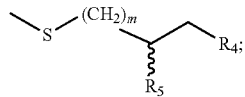

$R_2$ and $R_4$ is sulfonate or phosphonate;
$R_5$ is hydrogen, hydroxy, or sulfhydryl;
m is 0, 1, 2, 3, 4, 5, or 6; and
X is a sulfur-containing amino acid or a peptide comprising from 2-10 amino acids;
or wherein X is a member of the group comprising a: lower thioalkyl (lower mercapto alkyl), lower alkylsulfonate, lower alkylphosphonate, lower alkenylsulfonate, lower alkyl, lower alkenyl, lower alkynyl, aryl, alkoxy, aryloxy, mercapto, alkylthio or hydroxy for a corresponding hydrogen atom.
The Formula (I) compounds or compositions of the present invention also include pharmaceutically-acceptable salts, prodrugs, analogs, conjugates, hydrates, solvates, polymorphs, stereoisomers (including diastereoisomers and enantiomers) and tautomers thereof.

By way of non-limiting example, the Formula (I) compounds or compositions of the present invention include the disodium salt of 2,2'-dithio-bis-ethane sulfonate (which has also been referred to in the literature as dimesna, Tavocept™, and BNP7787). Additionally, by way of non-limiting example, the Formula (I) compounds or compositions of the present invention include the metabolite of disodium 2,2'-dithio-bis-ethane sulfonate, known as 2-mercapto ethane sulfonate sodium (also known in the literature as mesna) or 2-mercapto ethane sulfonate conjugated with a substituent group consisting of:
-Cys, -Homocysteine, -Cys-Gly, -Cys-Glu, -Homocysteine, -Homocysteine-Gly, -Homocysteine-Glu, -Cys-Glu,

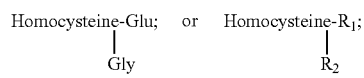

wherein $R_1$ and $R_2$ are any L- or D-amino acids.

It should be noted that all of the aforementioned chemical entities and compounds in the previous two (2) paragraphs are included in Formula (I) compounds of the present invention. The compounds of Formula (I) include pharmaceutically-acceptable salts of such compounds, as well as prodrugs, analogs, conjugates, hydrates, solvates and polymorphs, as well as stereoisomers (including diastereoisomers and enantiomers) and tautomers of such compounds. Compounds of Formula (I), and their synthesis are described in, e.g., U.S. Pat. Nos. 5,808,160, 5,922,902, 6,160,167, and 6,504,049; and Published U.S. Patent Application No. 2005/0256055, the disclosures of which are hereby incorporated by reference in their entirety.

As used herein, the terms "heteroconjugates", "mesna heteroconjugate", "mesna conjugate", or "mesna derivative" represent the metabolite of disodium 2,2'-dithio-bis-ethane sulfonate, known as 2-mercapto ethane sulfonate sodium (mesna), as a disulfide form which is conjugated with a substituent group consisting of:
-Cys, -Homocysteine, -Cys-Gly, -Cys-Glu, -Homocysteine, -Homocysteine-Gly, -Homocysteine-Glu, -Cys-Glu,

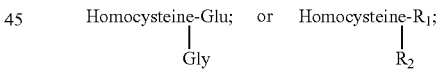

wherein $R_1$ and $R_2$ are any L- or D-amino acids. Mesna heteroconjugate compounds are included in the Formula (I) compounds and may be synthesized as described in Published U.S. Patent Application 2005/0256055, the disclosure of which is incorporated herein, by reference, in its entirety.

As utilized herein, the term "oxidative metabolism-affecting compound" is a compound, formulation, or agent which is capable of: mitigating or preventing: (i) the overexpression (or increased activity, or both) of thioredoxin or glutaredoxin in cancer cells; (ii) the loss of apoptotic sensitivity to therapy (i.e., drug or ionizing radiation resistance); (iii) increased conversion of RNA into DNA (involving ribonucleotide reductase); (iv) altered gene expression; (v) increased cellular proliferation signals and rates; (vi) increased thioredoxin peroxidase; and/or (vii) increased angiogenic activity (i.e., increased blood supply to the tumor). Accordingly, by pharmacological inactivation or modulation of thioredoxin and/or glutaredoxin by the proper medical administration of effective levels and schedules of the oxidative metabolism-affecting compounds of the present invention, can result in enhancement of chemotherapy effects and thereby lead to increased patient survival.

As used herein, a "medically-sufficient dose" or a "medically-sufficient amount" in reference to the compounds or compositions of the instant invention refers to the dosage that is sufficient to induce a desired biological, pharmacological, or therapeutic outcome in a subject with neoplastic disease. That result can be: (i) cure or remission of previously observed cancer(s); (ii) shrinkage of tumor size; (iii) reduction in the number of tumors; (iv) delay or prevention in the growth or reappearance of cancer; (v) selectively sensitizing cancer cells to the anti-cancer activity of chemotherapeutic agents; (vi) restoring or increasing apoptotic effects or sensitivity in tumor cells; and/or (vii) increasing the time of survival of the patient, alone or while concurrently experiencing reduction, prevention, mitigation, delay, shortening the time to resolution of, alleviation of the signs or symptoms of the incidence or occurrence of an expected side-effect(s), toxicity, disorder or condition, or any other untoward alteration in the patient.

As used herein, the term "g/m$^2$" represents the amount of a given compound or formulation in grams per square meter of the total body surface area of the subject to whom the compound or formulation is administered.

As used herein, the term "mg/m$^2$" represents the amount of a given compound or formulation in milligrams per square meter of the total body surface area of the subject to whom the compound or formulation is administered.

As utilized herein, the term "patient" refers to any individual or subject, without limitation, who is in need of treatment with a compound, composition, medicament, formulation, method, or kit which is disclosed in the present invention.

As used herein, the term "pre-treatment" comprises the administration of one or more medications, said administration occurring at any time prior chemotherapy administration in accordance with both the methods known within the art and the patient's medical condition.

As used herein, the term "pharmaceutically-acceptable salt" means salt derivatives of drugs which are accepted as safe for human administration. In the present invention, the Formula (I) compounds of the present invention include pharmaceutically-acceptable salts, which include but are not limited to: (i) a monosodium salt; (ii) a disodium salt; (iii) a sodium potassium salt; (iv) a dipotassium salt; (v) a calcium salt; (vi) a magnesium salt; (vii) a manganese salt; (viii) an ammonium salt; and (ix) a monopotassium salt.

As used herein the term "Quality of Life" or "QOL" refers, in a non-limiting manner, to a maintenance or increase in a cancer patient's overall physical and mental state (e.g., cognitive ability, ability to communicate and interact with others, decreased dependence upon analgesics for pain control, maintenance of ambulatory ability, maintenance of appetite and body weight (lack of cachexia), lack of or diminished feeling of "hopelessness"; continued interest in playing a role in their treatment, and other similar mental and physical states).

As used herein the terms "reactive oxygen species (ROS)" and "reactive nitrogen species (RNS)" refer to ionic species which may result from a variety of metabolic and/or environmental processes. By way of non-limiting example, intracellular ROS (e.g., hydrogen peroxide: $H_2O_2$, superoxide anion: $O_2^-$, hydroxyl radical: $OH^-$, nitric oxide, and the like) may be generated by several mechanisms: (i) by the activity of radiation; (ii) during xenobiotic and drug metabolism; and (iii) under relative hypoxic, ischemic and catabolic metabolic conditions.

As used herein, the term "reducing" includes preventing, attenuating the overall severity of, delaying the initial onset of, and/or expediting the resolution of the acute and/or chronic pathophysiology associated with malignancy in a subject.

As used herein the term "redox state", "redox potential", "oxidative/reductive state" of any particular biological environment can be defined as the sum of oxidative and reductive processes occurring within that environment, which affects the extent to which molecules are oxidized or reduced within it. The redox potential of biological ions or molecules is a measure of their tendency to lose an electron (i.e., thereby becoming oxidized). Under normal physiological circumstances, most intracellular biological systems are predominantly found in a reduced state. Within cells, thiols (R—SH) such as glutathione (GSH) are maintained in their reduced state, as are the nicotinamide nucleotide coenzymes NADH and NADPH. Conversely, plasma is generally an oxidizing environment due to the high partial pressure of oxygen and the relative absence of disulfide reducing enzymes. Physiological circumstances can, however, arise which alter the overall redox balance and lead to a more oxidizing environment on cells. In biological systems, this activity arises as a result of changes in intracellular oxidative metabolism and physiological systems have evolved to preserve, protect, and control the normal reducing environment. However, when the changes overwhelm these protective mechanisms, oxidative damage and profound biological changes can occur. Cancer cells have been observed to have the ability to mount more effective anti-oxidative responses to changes in intracellular oxidative metabolism (e.g., oxidative stress) in comparison to normal, non-cancerous, cells, thereby leading to a survival advantage and the ability to resist or escape the anti-cancer and cytotoxic action of chemotherapeutic agent(s).

As utilized herein, the term "redox response" refers to the biological response to induce antioxidant systems against changes in oxidative metabolism to maintain the homeostasis in the intracellular redox balance.

As used herein, the term "receive" or "received" refers to a subject who has cancer and who has received, is currently receiving, or will receive one or more chemotherapeutic agents and/or an oxidative metabolism-affecting Formula (I) compound of the present invention.

As used herein the term "synergism" or "synergistic" means the anti-cancer activity achieved by the above-defined Formula (I) compounds in combination with chemotherapeutic agent(s) is greater than the anti-cancer activity achieved by either form of treatment individually. For example, this may be mathematically expressed as the synergistic result of treatment with Drugs A+B administered together (as taught herein)=Result C>Drug A Result, alone+Drug B Result, alone. In contrast, a purely additive result may be mathematically expressed as: Drugs A+B administered together=Result C=Drug A Result, alone+Drug B Result, alone. In the foregoing examples, Drug A can represent Formula (I) compounds and the observed treatment result alone or combined, and Drug B can represent any single chemotherapy agent or combination of chemotherapy agents that are administered alone.

The term "solvate" or "solvates" refers to a molecular complex of a compound such as an oxidative metabolism-affecting Formula (I) compound of the present invention with one or more solvent molecules. Such solvent molecules are those commonly used in the pharmaceutical art (e.g., water, ethanol, and the like). The term "hydrate" refers to the complex where the solvent molecule is water.

As used herein, the term "treat" or "treated", with respect to a patient without cancer, refers to a patient, who is in need thereof, and who has received, is currently receiving, or will receive Formula (I) compounds of the present invention.

As used herein, the term "treat" or "treated", with respect to a patient with cancer, refers to a patient who has received, is currently receiving, or will receive one or more chemotherapeutic agents and/or Formula (I) compounds of the present invention.

As used herein, "treatment schedule time" means the difference in schedule of administration time, including: (i) the amount of drug administered per day or week; (ii) the amount of drug administered per day or week per $m^2$ of body surface area; and (iii) the amount of drug administered per day or week per kg of body weight.

As used herein, "difference in administration of drug treatment time", means permitting administration of treatment to occur in materially less time (a reduction in time from, e.g., 4 hours to 1 hour, from one day to 6 hours, and the like) thereby allowing the patient to minimize time in the outpatient or hospitalized treatment time.

As used herein, "treatment schedule time" or "treatment regimen" means the difference in schedule of administration time, including: (i) the amount of drug administered per day or week; (ii) the amount of drug administered per day or week per $m^2$ of body surface area; or (iii) the amount of drug administered per day or week per kg of body weight.

Many types of cancer cells have been shown to have increased expression and/or activity of thioredoxin and/or glutaredoxin including, but not limited to, lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma. The overexpression (and possibly increased activity) of thioredoxin and/or glutaredoxin in cancer cells results in chemotherapy drug resistance to apoptosis. Such overexpression leads, e.g., to shortened patient survival that is believed to be mediated by increased concentrations or expression of thioredoxin/glutaredoxin, which in turn promote tumor-mediated resistance to chemotherapy-induced apoptosis, overexpression of oxidoperoxidases, increased conversion of RNA into DNA, increased nuclear transcription, increased cell proliferation, and/or increased angiogenesis, any of which can act in concert to provide the cancer cells the ability to resist chemotherapy and radiation therapy.

The present invention involves the medicinal and pharmacological inactivation and modulation of the thioredoxin/glutaredoxin system which thereby inactivates, reverses or modulates the drug-resistant properties in the cancer cells that are otherwise imparted by the increased levels or overexpression of thioredoxin/glutaredoxin in said cancer cells. The medicinal and pharmacological inactivation involves the administration of an oxidative metabolism-affecting Formula (I) compound of the present invention. Any of the aforementioned types of cancer that have increased expression or concentrations of thioredoxin and/or glutaredoxin are susceptible to and may benefit from thioredoxin-/glutaredoxin-based intervention by the present invention. The present invention also teaches how to optimize the schedule, dose, and combination of chemotherapy regimens in patients by the identification in-advance of and through-out treatment of the thioredoxin/glutaredoxin levels and the metabolic state within a sample of cancer cells isolated from the individual patients. Moreover, the use of kits that enable diagnostic and therapeutic optimization of the compositions and methods of the present invention to further enhance the survival outcome and benefit to patients by, for example, the determination of the optimum chemotherapeutic drug regimen to utilize. The present invention also teaches how to identify patients, in advance, who would not be likely to benefit from such intervention by the use of diagnostic kits, thereby allowing other treatment approaches that may be more clinically efficacious to be pursued.

I. Glutathione and Cysteine

Glutathione (GSH), a tripeptide (γ-glutamyl-cysteinyl-glycine) serves a highly important role in both intracellular and extracellular redox balance. It is the main derivative of cysteine, and the most abundant intracellular non-protein thiol, with an intracellular concentration approximately 10-times higher than other intracellular thiols. Within the intracellular environment, glutathione (GSH) is maintained in the reduced form by the action of glutathione reductase and NADPH. Under conditions of oxidative stress, however, the concentration of GSH becomes markedly depleted. Glutathione functions in many diverse roles including, but not limited to, regulating antioxidant defenses, detoxification of drugs and xenobiotics, and in the redox regulation of signal transduction. As an antioxidant, glutathione may serve to scavenge intracellular free radicals directly, or act as a co-factor for various other protection enzymes. In addition, glutathione may also have roles in the regulation of immune response, control of cellular proliferation, and prostaglandin metabolism. Glutathione is also particularly relevant to oncology treatment because of its recognized roles in tumor-mediated drug resistance to chemotherapeutic agents and ionizing radiation. Glutathione is able to conjugate electrophilic drugs such as alkylating agents and cisplatin under the action of glutathione S-transferases. Recently, GSH has also been linked to the efflux of other classes of agents such as anthracyclines via the action of the multidrug resistance-associated protein (MRP). In addition to drug detoxification, GSH enhances cell survival by functioning in antioxidant pathways that reduce reactive oxygen species, and maintain cellular thiols (also known as non-protein sulfhydryls (NPSH)) in their reduced states. See, e.g., Kigawa J, et al., Gamma-glutamyl cysteine synthetase up-regulates glutathione and multidrug resistance-associated protein in patients with chemoresistant epithelial ovarian cancer. *Clin. Cancer Res.* 4:1737-1741 (1998).

Cysteine, another important NPSH, as well as glutathione are also able to prevent DNA damage by radicals produced by ionizing radiation or chemical agents. Cysteine concentrations are typically much lower than GSH when cells are grown in tissue culture, and the role of cysteine as an in vivo cytoprotector is less well-characterized. However, on a molar basis cysteine has been found to exhibit greater protective activity on DNA from the side-effect(s) of radiation or chemical agents. Furthermore, there is evidence that cysteine concentrations in tumor tissues can be significantly greater than those typically found in tissue culture.

A number of studies have examined GSH levels in a variety of solid human tumors, often linking these to clinical outcome See, e.g., Hochwald, S. N., et al., Elevation of glutathione and related enzyme activities in high-grade and metastatic extremity soft tissue sarcoma. *American Surg. Oncol.* 4:303-309 (1997); Ghazal-Aswad, S., et al., The relationship between tumour glutathione concentration, glutathione S-transferase isoenzyme expression and response to single agent carboplatin in epithelial ovarian cancer patients. *Br. J. Cancer* 74:468-473 (1996); Berger, S. J., et al., Sensitive enzymatic cycling assay for glutathione: Measurement of glutathione content and its modulation by buthionine sulfoximine in vivo and in vitro human colon cancer. *Cancer Res.* 54:4077-4083 (1994). Wide ranges of tumor GSH concentrations have been reported, and in general these have been greater (i.e., up to 10-fold) in tumors compared to adjacent normal tissues. Most researchers have assessed the GSH content of bulk tumor tissue using enzymatic assays, or GSH plus cysteine using HPLC.

In addition, cellular thiols/non-protein sulfhydryls (NPSH), e.g., glutathione, have also been associated with increased tumor resistance to therapy by mechanisms that include, but are not limited to: (i) conjugation and excretion of chemotherapeutic agents; (ii) direct and indirect scavenging of reactive oxygen species (ROS) and reactive nitrogen species (RNS); and (iii) maintenance of the "normal" intracellular redox state. Low levels of intracellular oxygen within tumor cells (i.e., tumor hypoxia) caused by aberrant structure and function of the associated tumor vasculature, has also been shown to be associated with chemotherapy therapy-resistance and biologically-aggressive malignant disease. Oxidative stress, commonly found in regions of intermittent hypoxia, has been implicated in regulation of glutathione metabolism, thus linking increased NPSH levels to tumor hypoxia. Therefore, it is also important to characterize both NPSH expression and its relationship to tumor hypoxia in tumors and other neoplastic tissues.

The heterogeneity of NPSH levels was examined in multiple biopsies obtained from patients with cervical carcinomas who were entered into a study investigating the activity of cellular oxidation and reduction levels (specifically, hypoxia) on the response to radical radiotherapy. See, e.g., Fyles, A., et al., (Oxygenation predicts radiation response and survival in patients with cervix cancer. *Radiother. Oncol.* 48:149-156 (1998). The major findings from this study were that the intertumoral heterogeneity of the concentrations of GSH and cysteine exceeds the intratumoral heterogeneity, and that cysteine concentrations of approximately 21 mM were found in some samples, confirming an earlier report by Guichard, et al., (Glutathione and cysteine levels in human tumour biopsies. *Br. J. Radiol.* 134:63557-635561 (1990)). These levels of cysteine are much greater than those typically seen in tissue culture, suggesting that cysteine might exert a significant radioprotective activity in cervical carcinomas and possibly other types of cancer.

There is also extensive literature showing that elevated cellular glutathione levels can produce drug resistance in experimental models, due to drug detoxification or to the antioxidant activity of GSH. In addition, radiation-induced DNA radicals can be repaired non-enzymatically by GSH and cysteine, indicating a potential role for NPSH in radiation resistance. While cysteine is the more effective radioprotective agent, it is usually present in lower concentrations than GSH. Interestingly, under fully aerobic conditions, this radioprotective activity appears to be relatively minor, and NPSH compete more effectively with oxygen for DNA radicals under the hypoxic conditions that exist in some solid tumors, which might play a significant role in radiation resistance.

Radiotherapy has traditionally been a major treatment modality for cervical carcinomas. Randomized clinical trials (Rose, D., et al., Concurrent cisplatin-based radiotherapy and chemotherapy for locally advanced cervical cancer. *New Engl. J. Med.* 340:1144-1153 (1999)) show that patient outcome is significantly improved when radiation therapy is combined with cisplatin-based chemotherapy, and combined modality therapy is now widely being utilized in treatment regimens. It is important to establish the clinical relevance of GSH and cysteine levels to drug and radiation resistance because of the potential to modulate these levels using agents such as buthionine sulfoximine; an irreversible inhibitor of γ-glutanylcysteine synthetase that can produce profound depletion of GSH in both tumor and normal tissues. See, e.g., Bailey, T., et al., Phase I clinical trial of intravenous buthionine sulfoximine and melphalan: An attempt at modulation of glutathione. *J. Clin. Oncol.* 12:194-205 (1994). Evaluation of GSH concentrations have reported elevated tumor GSH relative to adjacent normal tissue, and intertumoral heterogeneity in GSH content. These findings are consistent with the idea that GSH could play a clinically significant role in drug resistance. although it should be noted that relatively few studies have the sample size and follow up duration necessary to detect a significant relation between tumor GSH content and response to chemotherapy, hence there are no consistent clinical data to support this idea.

Koch and Evans (Cysteine concentrations in rodent tumors: unexpectedly high values may cause therapy resistance. *Int. J. Cancer* 67:661-667 (1996)) have shown that cysteine concentrations in established tumor cell lines can be much greater when these are grown as in vivo tumors, as compared to the in vitro values, suggesting that cysteine might play a more significant role in therapy resistance than previously considered. Although relatively few studies have reported on cysteine levels in human cancers, an earlier HPLC-based study of cervical carcinomas by Guichard, D. G., et al., (Glutathione and cysteine levels in human tumour biopsies. *Br. J. Radiol.* 134:63557-635561 (1990) reported cysteine concentrations greater than 1 mM in a significant number of cases. Thus, the fact that the variability in cysteine levels is greater than that for GSH suggests that these two thiols are regulated differently in tumors. By way of non-limiting example, the inhibition of γ-glutamylcysteine synthetase with the intravenous administration of buthionine sulfoximine (BSO) could result in elevated cellular levels of cysteine, due to the fact that the γ-glutamylcysteine synthetase is not being utilized for GSH de novo synthesis. Similar to GSH, cysteine possesses the ability to repair radiation-induced DNA radicals and cysteine also has the potential to detoxify cisplatin; a cytotoxic agent now routinely combined with radiotherapy to treat locally-advanced cervical carcinomas.

II. Glutaredoxin

Glutaredoxin and thioredoxin (TX) are members of the thioredoxin superfamily; that mediate disulfide exchange via their Cys-containing catalytic sites. While glutaredoxins mostly reduce mixed disulfides containing glutathione, thioredoxins are involved in the maintenance of protein sulfhydryls in their reduced state via disulfide bond reduction. See, e.g., Print, W. A., et al., The role of the thioredoxin and glutaredoxin pathways in reducing protein disulfide bonds in the *Escherichia coli* cytoplasm. *J. Biol. Chem.* 272:15661-15667 (1996). The reduced form of thioredoxin is generated by the action of thioredoxin reductase; whereas glutathione provides directly the reducing potential for regeneration of the reduced form of glutaredoxin.

Glutaredoxins are small redox enzymes of approximately 100 amino acid residues, which use glutathione as a cofactor. Glutaredoxins are oxidized by substrates, and reduced non-enzymatically by glutathione. In contrast to thioredoxins, which are reduced by thioredoxin reductase, no oxidoreductase, other than described in the present invention, exists that specifically reduces glutaredoxins. Instead, oxidized glutathione is regenerated by glutathione reductase. Together these components comprise the glutathione system. See, e.g., Holmgren, A. and Fernandes, A. P., Glutaredoxins: glutathione-dependent redox enzymes with functions far beyond a simple thioredoxin backup system. *Antioxid. Redox. Signal.* 6:63-74 (2004); Holmgren, A., Thioredoxin and glutaredoxin systems. *J. Biol. Chem.* 264: 13963-13966 (1989).

Glutaredoxins basically function as electron carriers in the glutathione-dependent synthesis of deoxyribonucleotides by the enzyme ribonucleotide reductase. Like thioredoxin, which functions in a similar way, glutaredoxin possesses an active catalytic site disulfide bond. It exists in either a reduced or an oxidized form where the two cysteine residues are linked in an intramolecular disulfide bond. Human proteins containing this domain include: glutaredoxin thioltransferase (GLRX); glutaredoxin 2 (GLRX2); thioredoxin-like 2 (GLRX3); GLRX5; PTGES2; and TXNL3. See, e.g., Nilsson, L. and Foloppe, N., The glutaredoxin —C—P—Y—C— motif: influence of peripheral residues. *Structure* 12:289-300 (2004).

At least two glutaredoxin proteins exist in mammalian cells (12 or 16 kDa), and glutaredoxin, like thioredoxin, cycles between disulfide and dithiol forms. The conversion of glutaredoxin from the disulfide form (oxidized) to the dithiol (reduced) form is catalyzed non-enzymatically by glutathione and is illustrated, below. In turn, glutathione cycles between a thiol form (glutathione) that can reduce glutaredoxin and a disulfide form (glutathione disulfide); glutathione reductase enzymatically reduces glutathione disulfide to glutathione. This reaction is illustrated below:

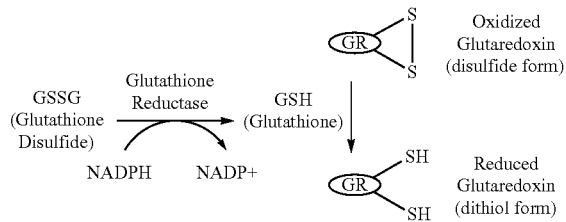

While the -CysXaaXaaCys- intramolecular disulfide bond is an essential part of the catalytic cycle for thioredoxin and protein disulfide isomerase, the most important oxidized species for glutaredoxins is a glutathionylated form.

III. The Thioredoxin Reductase (TRX)/Thioredoxin (TX) System Thioredoxin Reductase (TRX)

The thioredoxin system is comprised of thioredoxin reductase (TXR) and its main protein substrate, thioredoxin (TX), where the catalytic site disulfide of TX is reduced to a dithiol by TXR at the expense of NADPH. The thioredoxin system, together with the glutathione system (comprising NADPH, the flavoprotein glutathione reductase, glutathione, and glutaredoxin), is regarded as a main regulator of the intracellular redox environment, exercising control of the cellular redox state and antioxidant defense, as well as governing the redox regulation of several cellular processes. The system is involved in direct regulation of: (i) several transcription factors, (ii) apoptosis (i.e., programmed cell death) induction, and (iii) many metabolic pathways (e.g., DNA synthesis, glucose metabolism, selenium metabolism, and vitamin C recycling). See, e.g., Amér, E. S. J., et al., Physiological functions of thioredoxin and thioredoxin reductase. *Eur. J. Biochem.* 267:6102-6109 (2000). In addition to TXs, other endogenous substrates have been demonstrated for TXRs including, but not limited to, lipoic acid; lipid hydroperoxides; the cytotoxic peptide NK-lysin; vitamin K; dehydroascorbic acid; the ascorbyl free radical; and the tumor-suppressor protein p53. See, e.g., Reed, D. J., *Molecular and Cellular Mechanisms of Toxicity* (DeMatteis, F. and Smith, L. L., eds.), pp. 35-68, CRC Press, Boca Raton (2002). However, the exact physiological role that TXRs play in the reduction of most of these substrates has not yet been fully defined.

The mammalian thioredoxin reductases (TXRs) are enzymes belonging to the avoprotein family of pyridine nucleotide-disulfide oxidoreductases that includes lipoamide dehydrogenase, glutathione reductase, and mercuric ion reductase. Members of this family are homodimeric proteins in which each monomer includes an FAD prosthetic group, an NADPH binding site and an active site containing a redox-active disulfide. Electrons are transferred from NADPH via FAD to the active-site disulfide of TXR, which then reduces the substrate. See, e.g., Williams, C. H., *Chemistry and Biochemistry of Flavoenzymes* (Muller, F., ed.), pp. 121-211, CRC Press, Boca Raton (1995).

TXRs are named for their ability to reduce oxidized thioredoxins (TXs), a group of small, ubiquitous redox-active peptides that undergoes reversible oxidation/reduction of two conserved cysteine (Cys) residues within the catalytic site. The mammalian TXRs are selenium-containing flavoproteins that possess: (i) a conserved -Cys-Val-Asn-Val-Gly-Cys-catalytic site; (ii) an NADPH binding site; and (iii) a C-terminal Cys-Selenocysteine sequence that communicates with the catalytic site and is essential for its redox activity. See, e.g., Powis, G. and Monofort, W. R. Properties and biological activities of thioredoxins. *Ann. Rev. Pharmacol. Toxicol.* 41:261-295 (2001). These proteins exist as homodimers and undergo reversible oxidation/reduction. The activity of TXR is regulated by NADPH, which in turn is produced by glucose-6-phosphate dehydrogenase (G6DP), the rate-limiting enzyme of the oxidative hexose monophosphate shunt (HMPS; also known as the pentose phosphate pathway). Two human TXR isozyme genes have been cloned: a 54 Kda enzyme that is found predominantly in the cytoplasm (TXR-1) and a 56 Kda enzyme that contains a mitochondrial import sequence (TXR-2). Id. A third isoform of TXR, designated (TGR) is a TX and glutathione reductase localized mainly in the testis, has also been identified. See, e.g., Sun, Q. A., et al., Selenoprotein oxidoreductase with specificity for thioredoxin and glutathione systems. *Proc. Natl. Acad. Sci. USA* 98:3673-3678 (2001). Additionally, both mammalian cytosolic TX-1 and mitochondrial TX-2 have alternative splice variants. In humans, five different 5' cDNA variants have been reported. One of the splicing variants exhibits a 67 kDa protein with an N-terminal elongation instead of the common 55 kDa. The physiological functions of these TXR splice variants have yet to be elucidated. See, e.g., Sun, Q. A., et al., Heterogeneity within mammalian thioredoxin reductases: evidence for alternative exon splicing. *J. Biol. Chem.* 276: 3106-3114 (2001).

The TXR-1 isozyme has been the most extensively studied. TXR-1, as purified from tissues such as placenta, liver, or thymus, and expressed in recombinant form, possesses wide substrate specificity and generally high reactivity with electrophilic agents. The catalytic site of TXR-1 encompasses an easily accessible selenocysteine (Sec) residue situated within a C-terminal motif -Gly-Cys-Sec-Gly-COOH. See, e.g., Zhong, L., et al., Rat and calf thioredoxin reductase are homologous to glutathione reductase with a carboxyl-terminal elongation containing a conserved catalytically active penultimate selenocysteine residue. *J. Biol. Chem.* 273:8581-8591 (1998). Together with the neighboring cysteine, it forms a redox-active selenenylsulfide/selenolthiol motif that receives electrons from a redox-active -Cys-Val-Asn-Val-Gly-Cys- motif present in the N-terminal domain of the other subunit in the dimeric enzyme. See, e.g., Sandalova, T., et al., Three-dimensional structure of a mammalian thioredoxin reductase: implications for mechanism and evolution of a selenocysteine-dependent enzyme. *Proc. Natl. Acad. Sci. USA* 98:9533-9538 (2001). Substrates of the TXR-1 enzyme, that can be reduced by the selenolthiol motif, include: protein disulfides such as those in thioredoxin; NK-lysin; protein disulfide isomerase; calcium-binding proteins-1 and -2; and plasma glutathione peroxidase; as well as small molecules such as 5,5'-dithiobis(2-nitrobenzoate) (DTNB); alloxan; selenodiglutathione; methylseleninate; S-nitrosoglutathione; ebselen; dehydroascorbate; and alkyl hydroperoxides. See, e.g., Amk, E. S., et al., Preparation and assay of mammalian thioredoxin and thioredoxin reductase. *Method. Enzymol.* 300:226-239 (1999). Additionally, several quinone compounds can be reduced by the enzyme and one-electron reduced species of the quinones may furthermore derivatize the selenolthiol motif, thereby inhibiting the enzyme. The highly accessible selenenylsulfide/selenolthiol motif of the enzyme is extraordinarily reactive and can be rapidly derivatized by various electrophilic compounds.

Due to the many important functions of TXR, it is not surprising that its inhibition could be deleterious to cells due to an inhibition of the whole thioredoxin system. Moreover, in addition to a general inhibition of the thioredoxin system as a mechanism for cytotoxicity, it has also been shown that selenium-compromised forms of TXR may directly induce apoptosis in cells by a gain of function. See, e.g., Anestal, K., et al., Rapid induction of cell death by selenium-compromised thioredoxin reductase 1, but not by the fully active enzyme containing selenocysteine. *J. Biol. Chem.* 278:15966-15672 (2003). The signaling mechanisms of this apoptotic induction have not been presently elucidated. It is clear, however, that electrophilic compounds inhibiting TXR may have significant cellular toxicity as a result of these effects. From these findings it may surmised that TXR inhibition may be regarded as a potentially important mechanism by which several alkylating agents and various chemotherapeutic agents (e.g., the monohydrated complex of cisplatin, oxaliplatin, etc.) commonly utilized in anticancer treatment, may exert their cytotoxic effects.

Thioredoxin (TX)

Thioredoxins (TXs) are proteins that act as antioxidants by facilitating the reduction of other proteins by cysteine thiol-disulfide exchange. While glutaredoxins mostly reduce mixed disulfides containing glutathione, thioredoxins are involved in the maintenance of protein sulfhydryls in their reduced state via disulfide bond reduction. See, e.g., Print, W. A., et al., The role of the thioredoxin and glutaredoxin pathways in reducing protein disulfide bonds in the *Escherichia coli* cytoplasm. *J. Biol. Chem.* 272:15661-15667 (1996). Thiol-disulfide exchange is a chemical reaction in which a thiolate group (S) attacks a sulfur atom of a disulfide bond (—S—S—). The original disulfide bond is broken, and its other sulfur atom is released as a new thiolate, thus carrying away the negative charge. Meanwhile, a new disulfide bond forms between the attacking thiolate and the original sulfur atom. The transition state of the reaction is a linear arrangement of the three sulfur atoms, in which the charge of the attacking thiolate is shared equally. The protonated thiol form (—SH) is unreactive (i.e., thiols cannot attack disulfide bonds, only thiolates). In accord, thiol-disulfide exchange is inhibited at low pH (typically, <8) where the protonated thiol form is favored relative to the deprotonated thiolate form. The $pK_a$ of a typical thiol group is approximately 8.3, although this value can vary as a function of the environment. See, e.g., Gilbert, H. F., Molecular and cellular aspects of thiol-disulfide exchange. *Adv. Enzymol.* 63:69-172 (1990); Gilbert, H. F., Thiol/disulfide exchange equilibria and disulfide bond stability. *Meth. Enzymol.* 251:8-28 (1995).

Thiol-disulfide exchange is the principal reaction by which disulfide bonds are formed and rearranged within a protein. The rearrangement of disulfide bonds within a protein generally occurs via intra-protein thiol-disulfide exchange reactions; a thiolate group of a cysteine residue attacks one of the protein's own disulfide bonds. This process of disulfide rearrangement (known as disulfide shuffling) does not change the number of disulfide bonds within a protein, merely their location (i.e., which cysteines are actually bonded). Disulfide reshuffling is generally much faster than oxidation/reduction reactions, which actually change the total number of disulfide bonds within a protein. The oxidation and reduction of protein disulfide bonds in vitro also generally occurs via thiol-disulfide exchange reactions. Typically, the thiolate of a redox reagent such as glutathione or dithiothreitol (DTT) attacks the disulfide bond on a protein forming a mixed disulfide bond between the protein and the reagent. This mixed disulfide bond when attacked by another thiolate from the reagent, leaves the cysteine oxidized. In effect, the disulfide bond is transferred from the protein to the reagent in two steps, both thiol-disulfide exchange reactions.

Thioredoxin (TX) was originally described in 1964 as a hydrogen donor for ribonucleotide reductase which is an essential enzyme for DNA synthesis in *Escherichia coli*. Human thioredoxin was originally cloned as a cytokine-like factor named adult T cell leukemia (ATL)-derived factor (ADF), which was first defined as an IL-2 receptor α-chain (IL-2Ra, CD25)-inducing factor purified from the supernatant of human T cell leukemia virus type-1 (HTLV-1)-transformed T cell ATL2 cells. See, e.g., Yordi, J., et al., ADF, a growth-promoting factor derived from adult T cell leukemia and homologous to thioredoxin: possible involvement of dithiol-reduction in the IL-2 receptor induction. *EMBO J.* 8:757-764 (1989).

Proteins sharing the highly conserved -Cys-Xxx-Xxx-Cys- and possessing similar three-dimensional structure (i.e., the thioredoxin fold) are classified as belonging to the thioredoxin family. In the cytosol, members of the thioredoxin family include: the "classical cytosolic" thioredoxin 1 (TX-1) and glutaredoxin 1. In the mitochondria, family members include: mitochondrial-specific thyroxin 2 (TX-2) and glutaredoxin 2. Thioredoxin family members in the endoplasmic reticulum (ER) include: protein disulfide isomerase (PDI); calcium-binding protein 1 (CaBP1); ERp72; TX-related transmembrane protein (TMX); ERdj5; and similar proteins. Macrophage migration inhibitory factor (MIF) is a pro-inflammatory cytokine which was originally described as a soluble factor expressed by activated T cells in delayed-type hypersensitivity. See, e.g., Morand, E.

F., et al., MIF: a new cytokine link between rheumatoid arthritis and atherosclerosis. *Nat. Rev. Drug Discov.* 5:399-411 (2006). MIF also possesses a redox-active catalytic site and exhibits disulfide reductase activity. See, e.g., Kleeman, R., et al., Disulfide analysis reveals a role for macrophage migration inhibitory factor (MIF) as thiol-protein oxidoreductase. *J. Mol. Biol.* 280:85-102 (1998). MIF has pro-inflammatory functions, whereas thioredoxin 1 (TX-1) exhibits both anti-inflammatory and anti-apoptotic functions. TX-1 and MIF control their expression reciprocally, which may explain their opposite functions. However, TX-1 and MIF also share various similar characteristics. For example, both have a similar molecular weight of approximately 12 kDa and are secreted by a leaderless export pathway. They both share the same interacting protein such as Jun activation domain-binding protein 1 (JABI) in cells. Glycosylation inhibitory factor (GIF), which was originally reported as a suppressive factor for IgE response, is a posttranslationally-modified MIF with cysteinylation at $Cys^{60}$. The biological difference between MIF and GIF may be explained by redox-dependent modification, possibly involving TX-1. See, e.g., Nakamura, H., Thioredoxin and its related molecules: update 2005. *Antioxid. Redox Signal.* 7:823-828 (2005).

The mammalian thioredoxins (TXs) are a family of 10-12 Kda proteins that contain a highly conserved -Trp-Cys-Gly-Pro-Cys-Lys- catalytic site. See, e.g., Nishinaka, Y., et al., Redox control of cellular functions by thioredoxin: A new therapeutic direction in host defense. *Arch. Immunol. Ther. Exp.* 49:285-292 (2001). The active site sequences is conserved from *Escherichia coli* to humans. Thioredoxins in mammalian cells possess >90% homology and have approximately 27% overall homology to the *E. coli* protein.

As previously discussed, the thioredoxins act as oxidoreductases and undergo reversible oxidation/reduction of the two catalytic site cysteine (Cys) amino acid residues. The most prevalent thioredoxin, TX-1, is involved in a plethora of diverse biological activities. The reduced dithiol form of TX [TX-(SH)$_2$] reduces oxidized protein substrates that generally contain a disulfide group; whereas the oxidized disulfide form of TX [TX-(SS)] redox cycles back in an NADPH-dependent process mediated by thioredoxin reductase (TXR), a homodimer comprised of two identical subunits each having a molecular weight of approximately 55 kDa. The conversion of thioredoxin from the disulfide form (oxidized) to the dithiol form (reduced) is illustrated in the diagram, below:

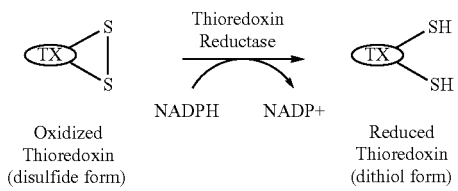

Oxidized Thioredoxin (disulfide form)    Reduced Thioredoxin (dithiol form)

Two principal forms of thioredoxin (TX) have been cloned. TX-1 is a 105-amino acid protein. In almost all (>99%) of the human form of TX-1, the first methionine (Met) residue is removed by an N-terminus excision process (see, e.g., Giglione, C., et al., Protein N-terminal methionine excision. *Cell. Mol. Life Sci.* 61:1455-1474 (2004), and therefore the mature protein is comprised of a total of 104 amino acid residues from the N-terminal valine (Val) residue. TX-1 is typically localized in the cytoplasm, but it has also been identified in the nucleus of normal endometrial stromal cells, tumor cells, and primary solid tumors. Various types of post-translational modification of TX-1 have been reported: (i) C-terminal truncated TX-1, comprised of 1-80 or 1-84 N-terminal amino acids, is secreted from cells and exhibits more cytokine-like functions than full-length TX-1; (ii) S-Nitrosylation at $Cys^{69}$ is important for anti-apoptotic effects; (iii) glutathionylation occurs at $Cys^{73}$, which is also the site responsible for the dimerization induced by oxidation; (iv) in addition to the original active site between $Cys^{32}$ $Cys^{35}$, another dithiol/disulfide exchange is observed between and $Cys^{62}$ and $Cys^{69}$, allowing intramolecular disulfide formation; and (v) $Cys^{35}$ and $Cys^{69}$ are reported to be the target for 15-deoxyprostaglandin-J$_2$. See, e.g., Nakamura, H., Thioredoxin and its related molecules: update 2005. *Antioxid. Redox Signal.* 7:823-828 (2005).

Reduced TX-1, but not its oxidized form or a Cys→Ser catalytic site mutant, has been shown to bind to various intracellular proteins and may regulate their biological activities. In addition to NK-κB and Ref-1, TX-1 binds to various isoforms of protein kinase C (PKC); p40 phagocyte oxidase; the nuclear glucocorticoid receptor; and lipocalin. TX-1 also binds to apoptosis signal-regulating kinase 1 (ASK 1) in the cytosol under normal physiological conditions. However, when TX-1 becomes oxidized under oxidative stress, ASK 1 is dissociated from TX-1 and TX-1 becomes a homodimer to transduce the apoptotic signal. ASK 1 is an activator of the JNK and p38 MAP kinase pathways, and is required for TNFα-mediated apoptosis. See, e.g., Saitoh, M., et al., Mammalian thioredoxin is a direct inhibitor of apoptosis signal-regulating kinase 1 (ask1). *EMBO J.* 17:2596-2606 (1998).

Another binding protein for TX-1 is thioredoxin-binding protein 2 (TBP-2) which is identical to Vitamin D$_3$ upregulating protein 1 (VDUP1). TBP-2/VDUP1 was originally reported as the product of a gene whose expression was upregulated in HL-60 cells stimulated with 1a, 25-dihydroxyvitamin D$_3$. The interaction of TBP-2/VDUP1 with TRX was observed both in vitro and in vivo. TBP-2/VDUP1 only binds to the reduced form of TRX and acts as an apparent negative regulator of TRX. See, e.g., Nishiyama, A., et al., Identification of thioredoxin-binding protein-2/Vitamin D(3) up-regulated protein 1 as a negative regulator of thioredoxin function and expression. *J. Biol. Chem.* 274:21645-21650 (1999). Although the mechanism is unknown, a reciprocal expression pattern of TRX and TBP-2 was often reported upon various types of stimulation. Several highly homologous genes of TBP-2/VDUP1 have been identified. A TBP-2 homologue, TBP-2-like inducible membrane protein (TLIMP) is a novel VD3 or peroxisome proliferator-activated receptor-γ (PPAR-γ) ligand-inducible membrane-associated protein and plays a regulatory role in cell proliferation and PPAR-γ activation. See, e.g., Oka, S., et al., Thioredoxin-binding protein 2-like inducible membrane protein is a novel Vitamin D$_3$ and peroxisome proliferator-activated receptor (PPAR) gamma ligand target protein that regulates PPAR gamma signaling. *Endocrinology* 147:733-743 (2006). Another TBP-2 homologous gene, DRH1, is reported to be down-regulated in hepatocellular carcinoma. See, e.g., Yamamoto, Y., et al., Cloning and characterization of a novel gene, DRH1, down-regulated in advanced human hepatocellular carcinoma. *Clin. Cancer Res.* 7:297-303 (2001). These results indicate that the familial members of TBP-2 may also play a role in cancer suppression.

TBP-2 also possesses a growth suppressive activity. Overexpression of TBP-2 was shown to resulted in growth suppression. TBP-2 expression is upregulated by Vitamin $D_3$ treatment and serum- or IL-2-deprivation, thus leading to growth arrest. TBP-2 is found predominantly in the nucleus. TBP-2 mRNA expression is down-regulated in several tumors (see, e.g., Butler, L. M., et al., The histone deacetylase inhibitor SAHA arrests cancer cell growth, up-regulates thioredoxin-binding protein-2 and down-regulates thioredoxin. *Proc. Natl. Acad. Sci. USA* 99:11700-11705 (2002)) and lymphoma (see, e.g., Tome, M. E., et al., A redox signature score identifies diffuse large B-cell lymphoma patients with poor prognosis. *Blood* 106:3594-3601 (2005)), suggesting a close association between the expression reduction and tumorigenesis. TBP-2 expression is also downregulated in melanoma metastasis. See, e.g., Goldberg, S. F., et al., Melanoma metastasis suppression by chromosome 6: evidence for a pathway regulated by CRSP3 and TXNIP. *Cancer Res.* 63:432-440 (2003).

Loss of TBP-2 seems to be an important step of human T cell leukemia virus 1 (HTLV-1) transformation. In an in vitro model, HTLV-1-infected T-cells required IL-2 to proliferate in the early phase of transformation, but subsequently lost cell cycle control in the late phase, as indicated by their continuous proliferative state in the absence of IL-2. The change of cell growth phenotype has been suggested to be one of the oncogenic transformation processes. See, e.g., Maeda, M., et al., Evidence for the interleukin-2 dependent expansion of leukemic cells in adult T cell leukemia. *Blood* 70:1407-1411 (1987). The expression of TBP-2 is lost in HTLV-1-positive IL-2-independent T cell lines (due to the DNA methylation and histone deacetylation); but is maintained in HTLV-I-positive IL-2-dependent T cell lines, as well as in HTLV-1-negative T cell lines. See, e.g., Ahsan, M. K., et al., Loss of interleukin-2-dependency in HTLV-1-infected T cells on gene silencing of thioredoxin-binding protein-2. *Oncogene* 25:2181-2191 (2005). Additionally, the murine knock-out HcB-19 strain, which has a spontaneous mutation in TBP-2/Txnip/VDUP1 gene, has been reported to have an increased incidence of hepatocellular carcinoma (HCC), showing that TBP-2/VDUP1 is a potential tumor suppressor gene candidate, in vivo. See, e.g., Sheth, S. S., et al., Thioredoxin-interacting protein deficiency disrupts the fasting-feeding metabolic transition. *J. Lipid Res.* 46:123-134 (2005). The same HcB-19 mice also exhibited decreased NK cells and reduced tumor rejection. TBP-2 was also found to interact with various cellular target such as JAB 1 and FAZF, and may be a component of a transcriptional repressor complex. See, e.g., Lee, K. N., et al., VDUP1 is required for the development of natural killer cells. *Immunity* 22:195-208 (2005). However, the precise mechanism of its molecular action remains to be elucidated.

TX-2 is a 166-amino acid protein that contains a 60-amino acid residue N-terminal translocation sequence that directs it to the mitochondria. See, e.g., Spyroung, M., et al., Cloning and expression of a novel mammalian thioredoxin. *J. Biol. Chem.* 272: 2936-2941 (1997). TX-2 is expressed uniquely in mitochondria, where it regulates the mitochondrial redox state and plays an important role in cell proliferation. TX-2-deficient cells fall into apoptosis via the mitochondria-mediated apoptosis signaling pathway. See, e.g., Noon, L., et al., The absence of mitochondrial thioredoxin-2 causes massive apoptosis and early embryonic lethality in homozygous mice. *Mol. Cell. Biol.* 23:916-922 (2003). TX-2 was found to form a complex with cytochrome c localized in the mitochondrial matrix, and the release of cytochrome c from the mitochondria was significantly enhanced when expression of TX-2 was inhibited. The overexpression of TX-2 produced resistance to oxidant-induced apoptosis in human osteosarcoma cells, indicating a critical role for the protein in protection against apoptosis in mitochondria. See, e.g., Chen, Y., et al., Overexpressed human mitochondrial thioredoxin confers resistance to oxidant-induced apoptosis in human osteosarcoma cells. *J. Biol. Chem.* 277:33242-33248 (2002).

As both TX-1 and TX-2 are known regulators of the manifestation of apoptosis under redox-sensitive caspases, their actions may be coordinated. However, the functions of TX-1 and TX-2 do not seem to be capable of compensating for each other completely, since TX-2 knockout mice were found be embryonically lethal. See, e.g., Noon, L., et al., The absence of mitochondrial thioredoxin-2 causes massive apoptosis and early embryonic lethality in homozygous mice. *Mol. Cell. Biol.* 23:916-922 (2003). Moreover, the different subcellular locations of both the thioredoxin reductase (TXR) and thioredoxin (TX) subtypes suggest that the cytoplasmic and mitochondrial systems may play different roles within cells. See, e.g., Powis, G. and Monofort, W. R. Properties and biological activities of thioredoxins. *Ann. Rev. Pharmacol. Toxicol.* 41:261-295 (2001).

IV. Biological Activities of the TRX/TX System

Physiological and Effects Modulated by Thioredoxin (TX) and Related Proteins

Mammalian cells contain a glutathione (GSH)/glutaredoxin system and a thioredoxin (TX)/thioredoxin reductase (TXR) system as the two major antioxidant systems. The intracellular concentration of GSH is approximately 1-10 milliMolar (mM) in mammalian cells, whereas the normal reported intracellular concentration of TX is approximately 0.1-2 µM. Accordingly, TX may initially appear as a minor component as an intracellular antioxidant. However, TX is a major enzyme supplying electrons to peroxiredoxins or methionine sulfoxide reductases, and acts as general protein disulfide reductase. TX knock-out mice are embryonic lethal (see, e.g., Matsui, M., et al., Early embryonic lethality caused by targeted disruption of the mouse thioredoxin gene. *Dev. Biol.* 178:179-185 (1996)), thus illustrating that the TX/TXR system is playing an essential survival role in mammalian cells. This importance may be explained by TX playing a crucial role in the interaction with specific target proteins including, but not limited to, the inhibition of apoptosis signal regulation kinase I (ASK1) activation (see, e.g., Saitoh, M., et al., Mammalian thioredoxin is a direct inhibitor of apoptosis signal-regulation kinase 1 (ASK1). *EMBO J.* 17:2596-2606 (1998)) and in the regulation of DNA binding activity of transcriptional factors such as AP-1, NF-κB and p53 for the transcriptional control of essential genes (see, e.g., Nakamura, H., et al., Redox regulation of cellular activation. *Ann. Rev. Immunol.* 15:351-369 (1997)). For example, during oxidative stress TX-1 translocates from the cytosol into the nucleus where it augments DNA-binding activity of these aforementioned transcriptional factors. Alternately, the role of TX in the defense against cellular oxidative stress or to supply the "building blocks" for DNA synthesis, via ribonucleotide reductase, is equally essential. TX-1 and the 14 Kda TX-like protein (TRP14) reactivates PTEN (a protein tyrosine phosphatase which reverses the action of phosphoinositide-3-kinase) by the reduction of the disulfide which is reversibly induced by hydrogen peroxide. See, e.g., Jeong, W., et al., Identification and characterization of TRP14, a thioredoxin-related protein of 14 Kda. *J. Biol. Chem.* 279:3142-3150 (2004). Exogenous TX-1 has been shown to be capable of entering cells and attenuate intracellular reactive oxygen species (ROS) generation and cellular apoptosis. See, e.g., Kondo, N., et al., Redox-sensing release of human thioredoxin from T lymphocytes with negative feedback loops. *J. Immunol.* 172:442-448 (2004). Additionally, HMG-CoA reductase inhibitors (commonly utilized for the prevention of atherosclerosis) have also been shown to augment S-Nitrosylation of TX-1 at $Cys^{69}$ and reduce oxidative stress. See, e.g., Haendeler, J., et al., Antioxidant effects of statins via S-nitrosylation and activation of thioredoxin in endothelial cells. *Circulation* 110:856-861 (2004).

The TX/TXR System as a Cofactor in DNA Synthesis

The TX/TXR-coupled system plays a critical role in the generation of deoxyribonucleotides which are needed in DNA synthesis and essential for cell proliferation. TX provides the electrons needed in the reduction of ribose by ribonucleotide reductase, an enzyme that catalyzes the conversion of nucleotide diphosphates into deoxyribonucleotides. Ribonucleotide reductase is necessary for DNA synthesis and cell proliferation. Diaziquone and doxorubicin have been shown to inhibit the TR/TXR system resulting in a concentration-dependent inhibition of cellular ribonucleotide reductase activity in human cancer cells. See, e.g., Mau, B., et al., Inhibition of cellular thioredoxin reductase by diaziquone and doxorubicin. *Biochem. Pharmacol.* 43:1621-1626 (1992). Similarly, the glutaredoxin/glutathione-coupled reaction also provides reducing equivalents for ribonucleotide reductase. For example, depletion of glutathione has been shown to inhibit DNA synthesis and induce apoptosis in a number of cancer cell lines. See, e.g., Dethlefsen, L. A., et al., Toxic effects of acute glutathione depletion by on murine mammary carcinoma cells. *Radiat. Res.* 114:215-224 (1988).

The Role of the TX/TXR System in Cellular Apoptosis

TX-1 was shown to prevent apoptosis (programmed cell death) when added to the culture medium of lymphoid cells or when its gene is transfected into these cells. Murine WEHI7.2 lymphoid cells underwent apoptosis when exposed to the glucocorticoid dexamethasone or the topoisomerase I inhibitor etoposide and, to a lesser extent, when exposed to the kinase inhibitor staurosporine or thapsigarin, an inhibitor of intracellular calcium uptake. See, e.g., Powis, G., et al., Thioredoxin control of cell growth and death and the effects of inhibitors. *Chem. Biol. Interact.* 111:23-34 (1998). TX levels in the cytoplasm and nucleus were increased following stable transfection of these cells with human TX-1, and as a result the transfected cells showed resistance to apoptosis when exposed to dexamethasone and the other cytotoxic agents. The pattern of apoptosis inhibition with TX-1 transfection was similar to that following transfection with the bcl-2 anti-apoptotic oncogene. In cooperation with redox factor-1, TX-1 induces p53-dependent p-21 transactivation leading to cell-cycle arrest and DNA repair. See, e.g., Ueda, S., et al., Redox control of cell death. *Antioxid. Redox Signal.* 4:405-414 (2002). In addition, TX-1 regulates the signaling for apoptosis by suppressing the activation of apoptosis signal-regulation kinase-1 (ASK-1). See, e.g., Nakamura, H., et al., Redox regulation of cellular activation. *Ann. Rev. Immunol.* 15:351-369 (1997).

The specific mechanism(s) by which TX-2 imparts resistance to chemotherapy apoptosis in cancer cells has not been fully elucidated. Based on the current studies, one may postulate, however, that it appears increases in cellular reductive power allows ongoing protective and/or reparative reduction of proteins, DNA, cell membranes or carbohydrates that have been damaged or would otherwise be damaged by oxidative chemical species, thus counteracting of the induced cellular apoptosis from the chemotherapy and/or radiation therapy. The analogous glutaredoxin/glutathione system may also prevent apoptosis. In either instance, there is a lack of apoptotic sensitivity to normal treatment interventions that appears to be mediated by the increased TX-2 and by glutaredoxin pathways. In the glutaredoxin mediated pathway, as an example, glutathione depletion with L-buthionine sulfoximine was shown to inhibit the growth of several breast and prostate cancer cell lines, and in rat R3230Ac mammary carcinoma cells, it markedly increased apoptosis. It is thought that mitochondrial swelling following depletion of glutathione may be the stimulus for apoptosis in these cells. See, e.g., Bigalow, J. E., et al., Glutathione depletion or radiation treatment alters respiration and induces apoptosis in R3230Ac mammary carcinoma. *Adv. Exp. Med. Biol.* 530:153-164 (2003). TX-2 has been shown to be a critical regulator of mitochondrial cytochrome c release and apoptosis. See, e.g., Tanaka, M., et al., Thioredoxin-2 (TX-2) is an essential gene in regulating mitochondrial-dependent apoptosis. *EMBO J.* 21:1695-1701 (2002).

The Role of TX in Stimulating Angiogenesis

Angiogenesis by cancer cells provides a growth and survival advantage that is localized to the primary as well as secondary (metastatic tumors). Malignant tumors are generally poorly vascular, however, with overexpression of angiogenesis factors, the tumor cells gain better nutrition and oxygenation, thereby promoting proliferation of cancer cells and growth of the tumor. Transfection of several different cell lines, including human breast cancer MCF-7, human colon cancer HT29, and murineWEHI7.2 lymphoma cells, with human TX-1 produced significant increases in secretion of vascular endothelial growth factor (VEGF). See, e.g., Welch, S. J., et al., The redox protein thioredoxin-1 increases hypoxia-inducible factor 1α protein expression: TXR-1 overexpression results in increased vascular endothelial growth factor production and enhanced tumor angiogenesis. *Cancer Res.* 62:5089-5095 (2003). VEGF secretion was increased by 41%-77% under normoxic (20% oxygen) conditions and by 46%-79% under hypoxic (1% oxygen) conditions. In contrast, transfection with a redox-inactive TX mutant (Cys→Ser) partially inhibited VEGF production. When TX-1-transfected WEHI7.2 cells were grown in SCID mice, VEGF levels were markedly increased and tumor angiogenesis (as measured by microvessel vascular density) was also increased by 2.5-fold, relative to wild-type WEHI7.2 tumors. Id. Accordingly, there is evidence that the thioredoxin system can increase VEGF levels in cancer cells.

Role of TX in Stimulating Cell Proliferation

Exposure to TX-1 was shown to stimulate the growth of lymphocytes, fibroblasts, and a variety of leukemic and solid tumor cell lines. See, e.g., Powis, G. and Monofort, W. R. Properties and biological activities of thioredoxins. *Ann. Rev. Pharmacol. Toxicol.* 41:261-295 (2001). In contrast, the previously discussed Cys→Ser redox mutant at 50-fold higher concentrations, did not stimulate cell growth. While the mechanisms for this proliferative effect are not fully elucidated, there is evidence that such TX-mediated increases in cell proliferation are multifactorial, and are related to both the increased production of various cytokines (e.g., IL-1, IL-2, and tumor necrosis factor α (TNFα)) and the potentiation of growth factor activity (e.g., basic fibroblast growth factor (bFGF)). Additionally, there is thought to also be increased DNA synthesis and transcription, as well.

The Antioxidant Effects of TX

Glutathione peroxidase and membrane peroxidases play a highly important role in protecting cells against the damaging effects of reactive oxygen species (ROS) including, but not limited to, oxygen radicals and peroxides. See, e.g., Bigalow, J. E., et al., The importance of peroxide and superoxide in the x-ray response. *Int. J. Radiat. Oncol. Biol. Phys.* 22:665-669 (1992). These enzymes utilize use thiol groups as an electron source for scavenging reactive oxygen species (ROS), and in the process, form homo- or heterodimers with other peroxidases through the formation of disulfide bonds with conserved cysteine residues. TX produces antioxidant effects primarily by serving as an electron donor for thioredoxin peroxidases. Accordingly, by the reduction of oxidized peroxidases, TX restores the enzyme to its monomeric form, which allows the enzyme to continue its oxyradical scavenging.

TX may also increase the expression of thioredoxin peroxidase. For example, in MCF-7 human breast cancer cells stably transfected with TX-1, mRNA for thioredoxin peroxidase was doubled relative to wild-type and empty-vector transformed cells, and Western blots showed increased protein levels as well. Moreover, TX-1 transfected murine WEH17.2 cells were more resistant to peroxide-induced apoptosis than wild-type and empty-vector transformed cells. However, TX-1 transfection did not protect the cells from apoptosis induced by dexamethasone or chemotherapeutic agents. See, e.g., Berggren, M. I., et al., Thioredoxin peroxidase-1 is increase in thioredoxin-1 transfected cells and results in enhanced protection against apoptosis caused by hydrogen peroxide, but not by other agents including dexamethasone, etoposide, and deoxorubin. *Arch. Biochem. Biophys.* 392:103-109 (2001).

The Role of TX in Stimulating Transcription Factor Activity

Thioredoxin (TX) increases the DNA-binding activity of a number of transcription factors (e.g., NF-κB, AP-1, and AP-2) and nuclear receptors (e.g., glucocorticoid and estrogen receptors). See, e.g., Nishinaka, Y., et al., Redox control of cellular functions by thioredoxin: A new therapeutic direction in host defense. *Arch. Immunol. Ther. Exp.* 49:285-292 (2001). By way of non-limiting example, with regard to NF-κB, TX reduces the Cys residue of the p50 subunit in the nucleus, thus allowing it to bind to DNA. See, e.g., Mau, B., et al., Inhibition of cellular thioredoxin reductase by diaziquone and doxorubicin. *Biochem. Pharmacol.* 43:1621-1626 (1992). In the cytoplasm, however, TX paradoxically interferes with NF-κB by blocking dissociation of the endogenous inhibitor IκB and interfering with signaling to IκB kinases. See, e.g., Hirota, K., et al., Distinct roles of thioredoxin in the cytoplasm and in the nucleus: A two-step mechanism of redox regulation of transcription factor nf-κB. *J. Biol. Chem.* 274:27891-27897 (1999). The effect of TX on some transcription factors is mediated via reduction of Ref-1, a 37 kDa protein that also possesses DNA-repair endonuclease activity. For example, TX reduces Ref-1, which in turn reduces cysteine residues within the fos and jun subunits of AP-1 to promote DNA binding. The redox activity of Ref-1 is found in its N-terminal domain, whereas its DNA repair activity is located among C-terminal sequences.

TX Binding to Cellular Proteins

Reduced TX-1, but not its oxidized form or a catalytic site Cys→Ser redox inactive mutant, binds to a variety of cellular proteins and may regulate their biological activities. See, e.g., Powis, G. and Monofort, W. R. Properties and biological activities of thioredoxins. *Ann. Rev. Pharmacol. Toxicol.* 41:261-295 (2001). In addition, to NK-κB and Ref-1, TX binds to: (i) apoptosis signal-regulating kinase 1 (ASK1), (ii) various isoforms of protein kinase C (PKC), (iii) p40 phagocyte oxidase, (iv) the nuclear glucocorticoid receptor, and (v) lipocalin. ASK1, for example, is an activator of the JNK and p38 MAP kinase pathways and is required for TFNα-mediated apoptosis. See, e.g., Ichijo, H., et al., Induction of apoptosis by ask1, a mammalian map kinase that activates jnk and p38 signaling pathways. *Science* 275:90-94 (1997). TX binds to a site at the N-terminal of ASK1, thus inhibiting the kinase activity and blocking ASK1-mediated apoptosis. See, e.g., Saitoh, M., et al., Mammalian thioredoxin is a direct inhibitor of apoptosis signal-regulation kinase 1 (ask1). *EMBO J.* 17:2596-2606 (1998). Under conditions of oxidative stress, however, reactive oxygen species are produced that oxidize the TX, thus promoting its dissociation from ASK1 and leading to the concomitant activation of ASK1.

TX/TXR Expression in Cancer

Various extracellular roles of thioredoxin (TX) have been examined in cancer. As previously described, TX was originally cloned as a cytokine-like factor named ADF. Independently, TX was also identified as an autocrine growth factor named 3B6-IL1 produced by Epstein-Barr virus-transformed B cells (see, e.g., Wakasugi, H., et al., Epstein-Barr virus-containing B-cell line produces an interleukin 1 that it uses as a growth factor. *Proc. Natl. Acad. Sci. USA* 84:804-808 (1987)) or as a B cell growth factor named MP6-BCGF produced by the T cell hybridoma MP6 (see, e.g., Rosen A, et al., A CD4+ T cell line-secreted factor, growth promoting for normal and leukemic B cells, identified as thioredoxin. *Int. Immunol.* 7:625-33 (1995)). Moreover, eosinophil cytotoxicity-enhancing factor (ECEF) was found as a truncated form of TX comprising which is the N-terminal 1-80 (or 1-84) residues of TX (Trx80) (see, e.g., Silberstein, D. S., et al., Human eosinophil cytotoxicity-enhancing factor. Eosinophil-stimulating and dithiol reductase activities of biosynthetic (recombinant) species with COOH-terminal deletions. *J. Biol. Chem.* 268:913-942 (1993)) and a component of "early pregnancy factor" which was an immunosuppressive factor in pregnant female serum was also identified as TX (see, e.g., Clarke, F. M., et al., Identification of molecules involved in the "early pregnancy factor" phenomenon. *J. Reprod. Fertil.* 93:525-539 (1991)). These historical reports, collectively, illustrate that TX has various important extracellular functions.

Thioredoxin (TX) expression is increased in a variety of human malignancies including, but not limited to, lung cancer, colorectal cancer, cervical cancer, hepatic cancer, pancreatic cancer, and adenocarcinoma. In addition, TX expression has also been associated with aggressive tumor growth. This increase in expression level is likely related to changes in TX protein structure and function. For example, in pancreatic ductal carcinoma tissue, TX levels were found to be elevated in 24 of 32 cases, as compared to normal pancreatic tissue. Glutaredoxin levels were increased in 29 of the cases. See, e.g., Nakamura, H., et al., Expression of thioredoxin and glutaredoxin, redox-regulating proteins, in pancreatic cancer. *Cancer Detect. Prev.* 24:53-60 (2000). Similarly, tissue samples of primary colorectal cancer or lymph node metastases had significantly higher TX-1 levels than normal colonic mucosa or colorectal adenomatous polyps. See, e.g., Raffel, J., et al., Increased expression of thioredoxin-1 in human colorectal cancer is associated with decreased patient survival. *J. Lab. Clin. Med.* 142:46-51 (2003).

In two recent studies, TX expression was associated with aggressive tumor growth and poorer prognosis. In a study of 102 primary non-small cell lung carcinomas, tumor cell TX expression was measured by immunohistochemistry of formalin-fixed, paraffin-embedded tissue specimens. See, e.g., Kakolyris, S., et al., Thioredoxin expression is associated with lymph node status and prognosis in early operable non-small cell lung cancer. *Clin. Cancer Res.* 7:3087-3091 (2001). The absence of TX expression was significantly associated with lymph node-negative status (P=0.004) and better outcomes (P<0.05) and was found to be independent of tumor stage, grade, or histology. The investigators also concluded that these results were consistent with the proposed role of TX as a growth promoter in some human cancers, and overexpression may be indicative of a more aggressive tumor phenotype (hence the association of TX overexpression with nodal positivity and poorer outcomes). In another study of 37 patients with colorectal cancer, TX-1 expression tended to increase with higher Dukes stage (P=0.077) and was significantly correlated with reduced survival (P=0.004). After adjusting for Dukes stage, TX-1 levels remained a significant prognostic factor associated with survival (P=0.012). See, e.g., Raffel, J., et al., Increased expression of thioredoxin-1 in human colorectal cancer is associated with decreased patient survival. *J. Lab. Clin. Med.* 142:46-51 (2003). It should be noted that GSH levels were not determined in either of the aforementioned studies.

The relationship between TXR activity and tumor growth is less clear. Tumor cells may not need to increase expression of the TXR enzyme, although its catalytic activity may be increased functionally. For example, human colorectal tumors were found to have 2-times higher TXR activity than normal colonic mucosa. See, e.g., Mustacich, D. and Powis, G., Thioredoxin reductase. *Biochem. J.* 346:1-8 (2000). TXR has also been reported to be elevated in human primary melanoma and to show a correlation with invasiveness. See, e.g., Schallreuter, K. U., et al., Thioredoxin reductase levels are elevated in human primary melanoma cells. *Int. J. Cancer* 48:15-19 (1991). Further evaluations relating TXR enzyme levels and catalytic activity with cancer stage and outcome are required needed to fully elucidate this relationship.

The Role of TX in Stimulating Hypoxia-Inducible Factor (HIF)

Cancer cells are able to adapt to the hypoxic conditions found in nearly all solid tumors. Hypoxia leads to activation of hypoxia-inducible factor 1 (HIF-I), which is a transcription factor involved in development of the cancer phenotype. Specifically, HIF binds to hypoxia response elements (HRE) and induces expression of a variety of genes that serve to promote: (i) angiogenesis (e.g., VEGF); (ii) metabolic adaptation (e.g., GLUT transporters, hexokinase, and other glycolytic enzymes); and (iii) cell proliferation and survival. HIF is comprised of two subunits—HIF-1α (that is induced by hypoxia) and HIF-1β (that is expressed constitutively). TX overexpression has been shown to significantly increase HIF-1α under both normoxic and hypoxic conditions, and this was associated with increased HRE activity demonstrated in a luciferase reporter assay as well as increased expression of HRE-regulated genes. HIF may provide tumor cells with a survival advantage under hypoxic conditions by inducing hexokinase and thus allowing glycolysis to serve as the predominant energy source. For example, surgical specimens from patients with metastatic liver cancer had fewer tumor blood vessels and higher hexokinase expression than specimens from hepatocellular carcinoma patients. Hexokinase expression was correlated with HIF-1 α expression in both populations, and they co-localized in tumor cells found near necrotic regions.

The TX/TXR System in Cancer Drug Resistance

As previously discussed, mammalian thioredoxin reductase (TXR) is involved in a number of important cellular processes including, but not limited to: cell proliferation, antioxidant defense, and redox signaling. Together with glutathione reductase (GR), it is also the main enzyme providing reducing equivalents to many cellular processes. GR and TXR are flavoproteins of the same enzyme family, but only the latter is a selenoprotein. With the catalytic site containing selenocysteine, TXR may catalyze reduction of a wide range of substrates, but it can also be easily targeted by electrophilic compounds due to the extraordinarily high reactivity of the selenocysteine moiety. In a recent studies, the inhibition of TXR and GR by anti-cancer alkylating agents and platinum-containing compounds was compared to the inhibition of GR. See, e.g., Wang, X., et al., Thioredoxin reductase inactivation as a pivotal mechanism of ifosfamide in cancer therapy. *Eur. J. Pharmacol.* 579:66-75 (2008); Wang, X., et al., Cyclophosphamide as a potent inhibitor of tumor thioredoxin reductase in vivo. *Toxicol. Appl. Pharmacol.* 218:88-95 (2007); Witte, A-B., et al., Inhibition of thioredoxin reductase but not of glutathione reductase by the major classes of alkylating and platinum-containing anticancer compounds. *Free Rad. Biol. Med.* 39:696-703 (2005). These studies found that: (i) the nitrosourea, carmustine, can inhibit both GR and TXR; (ii) the nitrogen mustards (cyclophosphamide, chlorambucil, and melphalan) and the alkyl sulfonate (busulfan) irreversibly inhibited TXR in a concentration- and time-dependent manner, but not GR; (iii) the oxazaphosphorine, ifosfamide, inhibited TXR; (iv) the anthracyclines (daunorubicin and doxorubicin) were not inhibitors of TXR; (v) cisplatin, its monohydrated complex, oxaliplatin, and transplatin irreversibly inhibited TXR, but not GR; and (vi) carboplatin could not inhibit either TXR or GR. Other studies have shown that the irreversible inhibition of TXR by quinones, nitrosoureas, and 13-cis-retinoic acid is markedly similar to the inhibition of TXR by cisplatin, oxaliplatin, and transplatin. See, e.g., Arnér, E. S. J., et al., Analysis of the inhibition of mammalian thioredoxin, thioredoxin reductase, and glutaredoxin by cis-diamminedichloroplatinum (II) and its major metabolite, the glutathione-platinum complex. *Free Rad. Biol. Med.* 31:1170-1178 (2001).

Studies have also shown that the highly accessible selenenylsulfide/selenolthiol motif of the TXR enzyme can be rapidly derivatized by a number of electrophilic compounds. See, e.g., Beeker, K, et al., Thioredoxin reductase as a pathophysiological factor and drug target. *Eur. J. Biochem.* 262:6118-6125 (2000). These compounds include, but are not limited to: (i) cisplatin and its glutathione adduct (see, e.g., Amér, E. S. J., et al., Analysis of the inhibition of mammalian thioredoxin, thioredoxin reductase; glutaredoxin by cis-diamminedichlamplatinum (II) and its major metabolite, the glutathioneplatinum complex. *Free Rad. Biol. Med.* 31:1170-1178 (2001)); (ii) dinitrohalobenzenes (see, e.g., Nordberg, J., et al., Mammalian thioredoxin reductase is irreversibly inhibited by dinitrohalobenzenes by alkylation of both the redox active selenocysteine and its neighboring cysteine residue. *J. Biol. Chem.* 273:10835-10842 (1998)); (iii) gold compounds (see, e.g., Gromer, S., et al., Human placenta thioredoxin reductase: Isolation of the selenoenzyme, steady state kinetics, inhibition by therapeutic gold compounds. *J. Biol. Chem.* 273:20096-20101 (1998)); (iv) organochalogenides (see, e.g., Engman, L., et al., Water-soluble organatellurium compounds inhibit thioredoxin reductase and the growth of human cancer cells. *Anticancer Drug. Des.* 15:323-330 (2000)); (v) different naphthazarin derivatives (see, e.g., Dessolin, I., et al., Bromination studies of the 2,3-dimethylnaphthazarin core allowing easy access to naphthazarin derivatives. *J. Org.*

*Chem.* 66:5616-5619 (2001)); (vi) certain nitrosoureas (see, e.g., Sehallreuter, K. U., et al., The mechanism of action of the nitrosourea anti-tumor drugs and thioredoxin reductase, glutathione reductase and ribonucleotide reductase. *Biochim. Biophys. Acta* 1054:14-20 (1990)); and (vii) general thiol or selenol alkylating agents such as C-vinylpyridine, iodoacetamide or iodoacetic acid (see, e.g., Nordberg, J., et al., Mammalian thioredoxin reductase is irreversibly inhibited by dinitrohalobenzenes by alkylation of both the redox active selenocysteine and its neighboring cysteine residue. *J. Biol. Chem.* 273:10835-10842 (1998)).

Similarly, several lines of evidence suggest that thioredoxin (TX) may also be necessary, but is not sufficient in toto, for conferring resistance to many chemotherapeutic drugs. This evidence includes, but is not limited to: (i) the resistance of adult T-cell leukemia cell lines to doxorubicin and ovarian cancer cell lines to cisplatin has been associated with increased intracellular TX-1 levels; (ii) hepatocellular carcinoma cells with increased TX-1 levels were less sensitive cisplatin (but not less sensitive to doxorubicin or mitomycin C); (iii) TX-1 mRNA and protein levels were increased by 4- to 6-fold in bladder and prostate cancer cells made resistant to cisplatin, but lowering TX-1 levels with an antisense plasmid restored sensitivity to cisplatin and increased sensitivity to several other cytotoxic drugs; (iv) TX-1 levels were elevated in cisplatin-resistant gastric and colon cancer cells; and (v) stable transfection of fibrosarcoma cells with TX-1 resulted in increased cisplatin resistance. See, e.g., Biaglow, J. E. and Miller, R. A., The thioredoxin reductase/thioredoxin system. *Cancer Biol. Ther.* 4:6-13 (2005).

Glutathione may also play a role in anti-cancer drug resistance. Glutathione-S-transferases catalyze the conjugation of glutathione to many electrophilic compounds, and can be upregulated by a variety of cancer drugs. Glutathione-S-transferases possess selenium-independent peroxidase activity. Mµ also has glutaredoxin activity. Some agents are substrates for glutathione-S-transferase and are directly inactivated by glutathione conjugation, thus leading to resistance. Examples of enzyme substrates include melphalan, carmustine (BCNU), and nitrogen mustard. In a panel of cancer cell lines, glutathione-S-transferase expression was correlated inversely with sensitivity to alkylating agents. Other drugs that upregulate glutathione-S-transferase may become resistant, because the enzyme also inhibits the MAP kinase pathway. These agents require a functional MAP kinase, specifically JNK and p38 activity, to induce an apoptotic response. See, e.g., Townsend, D. M. and Tew, K. D., The role of glutathione-S-transferase in anti-cancer drug resistance. *Oncogene* 22:7369-7375 (2003).

Targeting TX/TXR-Coupled Reactions

The biological activities of TX/TRX and their apparent relevance to aggressive tumor growth suggest that this system may be an attractive target for cancer therapy. Either individual enzymes or substrates can be altered. In cells that do not contain glutaredoxin, depletion of hexose monophosphate shunt (HMPS)-generated NADPH or, alternately, direct interaction with TX or TRX may prove to be viable approaches to blocking HMPS/TX/TRX-coupled reactions. In cells where glutaredoxin is present, its reducing activity also may need to be targeted through depletion of glutathione.

Thioredoxin in Plasma or Serum as an Oxidative Metabolism Biological Marker

Thioredoxin 1 (TX) is released by cells in response to changes in oxidative metabolism. See, e.g., Kondo N, et al., Redox-sensing release of human thioredoxin from T lymphocytes with negative feedback loops. *J. Immunol.* 172: 442-448 (2004). Plasma or serum levels of TX are measurable by a sensitive sandwich enzyme-linked immunosorbent assay (ELISA). Serum plasma levels of TX are good markers for changes in oxidative metabolism in a variety of disorders. See, e.g., Burke-Gaffney, A., et al., Thioredoxin: friend or foe in human diseases? *Trends Pharmacol. Sci.* 26:398-404 (2004). For example, plasma levels of TRX are elevated in patients with acquired immunodeficiency syndrome (AIDS) and negatively correlated with the intracellular levels of GSH, suggesting that the HIV-infected individuals with AIDS. See, e.g., Nakamura, H., e t al., Elevation of plasma thioredoxin levels in HIV-infected individuals. *Int. Immunol.* 8:603-611 (1996). In patients with type C chronic hepatitis, serum levels of TRX and ferritin are good markers for the efficacy of interferon therapy. See, e.g., Sumida, Y., et al., Serum thioredoxin levels as an indicator of oxidative stress in patients with hepatitis C virus infection. *J. Hepatol.* 33:616-622 (2001). In the case of cancer, serum levels of TRX are elevated in patients with hepatocellular carcinoma (see, e.g., Miyazaki, K., et al., Elevated serum levels of serum thioredoxin in patients with hepatocellular carcinoma. *Biotherapy* 11:277-288 (1998)) and pancreatic cancer (see, e.g., Nakmura, H., et al., Expression of thioredoxin and glutaredoxin, redox-regulating proteins, in pancreatic cancer. *Cancer Detect. Prev.* 24:53-40 (2000)). The serum levels of TX decrease after the removal of the main tumor, suggesting that cancer tissues are the main source of the elevated TX in serum. See, e.g., Miyazaki, K., et al., Elevated serum levels of serum thioredoxin in patients with hepatocellular carcinoma. *Biotherapy* 11:277-288 (1998).

The Use of TX Therapy in Cancer Patients

Since TX shows anti-inflammatory effect in circulation, the clinical application of TX therapy is now planned, especially because TX has been shown to block neutrophil infiltration into the inflammatory site. For example, the administration of recombinant human TX (rhTX) inhibits bleomycin or inflammatory cytokine-induced interstitial pneumonia. See, e.g., Hoshino, T., et al., Redox-active protein thioredoxin prevents proinflammatory cytokine- or bleomycin-induced lung injury. *Am. J. Respir. Crit. Care Med.* 168:1075-1083 (2003). Therefore, acute respiratory distress syndrome (ARDS)/acute lung injury (ALI) is one disorder which is a good target for TX therapy. ARDS/ALI is caused by various etiologies including anti-cancer agents such as gefitinib, a molecular-targeted agent that inhibits epidermal growth factor receptor (EGFR) tyrosine kinase. The safety of TX therapy in cancer patients in currently being examined. Although the intracellular expression of TX in cancer tissues is associated with, e.g., resistance to anti-cancer agents (see, e.g., Yokomizo, A., et al., Cellular levels of thioredoxin associated with drug sensitivity to cisplatin, mitomycin C, deoxrubicin, and etoposide. *Cancer Res.* 55:4293-4296 (1995); Sasada, T., et al., Redox control and resistance to cis-diamminedichloroplatinum (II) (CDDP); protective effect of human thioredoxin against CDDP-induced cytotoxicity. *J. Clin. Investig.* 97:2268-2276 (1996)), there is no evidence showing that exogenously administered rhTRX promotes the growth of cancer. For example, there is no promoting effect of administered rhTRX on the growth of the tumor planted in nude mice. In addition, administered rhTRX has no inhibitory effect on the anti-cancer agent to suppress the tumor growth in nude mice. It may be explained by that the cellular uptake of exogenous TRX is quite limited and administered TRX in plasma immediately becomes the oxidized form which has no tumor growth stimulatory activity as previously mentioned.

Thioredoxin 1 (TX) expression is enhanced in cancer tissues and now inhibitors for TX and/or thioredoxin reductase (TXR) are studied as new anti-cancer agents. See, e.g., Powis, G., Properties and biological activities of thioredoxin. *Annu. Rev. Phamacol. Toxicol.* 41:261-295 (2001). From this aspect, TX gene therapy may be dangerous in cancer-bearing patients. In contrast, the administration of rhTX may be safe and applicable even in cancer-bearing patients to attenuate the inflammatory disorders associated with the leukocyte infiltration.

It should also be noted that, the Japan Phase III non-small cell lung carcinoma (NSCLC) Clinical Trial and the United States (U.S.) Phase II NSCLC Clinical Trial, that are discussed and described in the present invention represent controlled clinical evidence of a survival increase caused a thioredoxin and/or glutaredoxin inactivating or modulating medicament (that act pharmacologically in the manner of the oxidative metabolism-affecting Formula (I) compounds of the present invention). These two aforementioned clinical trials will be fully discussed in a later section. However, it is observed from the data from both of these controlled clinical trials that there is a marked increase in patient survival, especially in the non-small cell lung carcinoma, adenocarcinoma sub-type patients receiving a Formula (I) compound of the present invention. For example, there was an increase in median survival time of approximately 138 days (i.e., 4.5 months) and approximately 198 days (i.e., 6.5 months) for adenocarcinoma patients in the Tavocept arm of the Japan Phase III NSCLC Clinical Trial and the U.S. Phase II NSCLC Clinical Trial, respectively.

Various representative Formula (I) compounds of the present invention have been synthesized and purified. Additionally, disodium 2,2'-dithio-bis ethane sulfonate (also referred to in the literature as Tavocept™, dimesna, and BNP7787), a Formula (I) compound of the present invention, has been introduced into Phase I, Phase II, and Phase III clinical testing in patients, as well as in non-clinical testing, by the Assignee, BioNumerik Pharmaceuticals, Inc., with guidance provided by the Applicant of the instant invention. In addition, this compound has been utilized in a multicenter, randomized, Phase II clinical trial involving patients with advanced Stage IIIB/IV non-small cell lung carcinoma (NSCLC), including adenocarcinoma (the U.S. Phase II NSCLC Clinical Trial). Data from the aforementioned recent Phase II and Phase III clinical trials utilizing disodium 2,2'-dithio-bis ethane sulfonate (Tavocept™) with chemotherapeutic agent(s) have demonstrated the ability of disodium 2,2'-dithio-bis ethane sulfonate to markedly increase the survival time of individuals with non-small cell lung carcinoma (NSCLC), including the adenocarcinoma sub-type. In brief, experimental evidence supports the finding that disodium 2,2'-dithio-bis ethane sulfonate functions to increase patient survival time by increasing oxidative metabolism within tumor cells in a selective manner.

The Applicant of the present invention has previously disclosed the use of disodium 2,2'-dithio-bis ethane sulfonate and other dithioethers to: (i) mitigate nephrotoxicity (see, e.g., U.S. Pat. Nos. 5,789,000; 5,866,169; 5,866,615; 5,866,617; and 5,902,610) and (ii) mitigate neurotoxicity (see, e.g., Published U.S. Patent Application No. 2003/0133994); all of which are incorporated herein by reference in their entirety. However, as previously stated, the novel approach of the present invention involve compositions, methods, and kits which cause an increase in survival time of cancer patients, wherein the cancer either: (i) overexpresses thioredoxin and/or glutaredoxin and/or (ii) exhibits evidence of thioredoxin- or glutaredoxin-mediated resistance to one or more chemotherapeutic agents.

The present invention discloses and claims: (i) compositions which cause an increase in the time of survival in patients with cancer; wherein the cancer either overexpresses thioredoxin or glutaredoxin or exhibits or possesses thioredoxin- or glutaredoxin-mediated resistance to one or more chemotherapeutic drugs; (ii) methods of treatment which cause an increase in time of survival in patients with cancer; wherein the cancer either overexpresses thioredoxin or glutaredoxin and/or exhibits or possesses thioredoxin- or glutaredoxin-mediated resistance to one or more chemotherapeutic drugs; (iii) kits for the administration of these compositions to treat patients with cancer; (iv) methods for quantitatively ascertaining the level of expression of thioredoxin or glutaredoxin in patients with cancer; (v) methods of using the level and pattern of expression of thioredoxin or glutaredoxin in the cancer in the initial diagnosis, planning of subsequent treatment methodologies, and/or ascertaining the potential treatment responsiveness of the specific cancer of the patients with cancer; (vi) kits for quantitatively ascertaining the level of expression of thioredoxin or glutaredoxin in the cancer of patients with cancer; (vii) methods of treatment which cause an increase in time of survival in patients with cancer; wherein the cancer either overexpresses thioredoxin or glutaredoxin and/or exhibits or possesses thioredoxin- or glutaredoxin-mediated resistance to one or more chemotherapeutic drugs and the treatment comprises the administration of the chemotherapeutic agents that are sensitive to thioredoxin and/or glutaredoxin overexpression, either of which result in tumor mediated drug resistance and enhanced angiogenesis; and (viii) methods for optimizing the schedule, dose, and combination of chemotherapy regimens in patients by ascertaining, in-advance and throughout the treatment course, the thioredoxin levels, glutaredoxin levels and metabolic state in a sample from the patient with cancer.

In one embodiment of the present invention, a composition for increasing survival time in a patient with cancer is disclosed, wherein the cells comprising the cancer which are isolated from the patient with cancer either: (i) overexpress thioredoxin or glutaredoxin and/or (ii) exhibit evidence of thioredoxin-mediated or glutaredoxin-mediated resistance to the chemotherapeutic agent or agents used to treat said patient with cancer; is administered in a medically-sufficient dose to the patient with cancer, either prior to, concomitantly with, or subsequent to the administration of a chemotherapeutic agent or agents whose cytotoxic or cytostatic activity is adversely effected by either: (i) the overexpression of thioredoxin or glutaredoxin and/or (ii) the thioredoxin-mediated or glutaredoxin-mediated treatment resistance.

It should be noted that the exhibition of thioredoxin-mediated or glutaredoxin-mediated treatment resistance is defined as "evidence of" due to the fact that it is neither expected, nor possible to prove with 100% certainty that the cancer cells exhibit thioredoxin-mediated or glutaredoxin-mediated treatment resistance, prior to the treatment of the patient. By way of non-limiting example, the current use of, e.g., florescence in situ hybridization (FISH) or immunohistochemistry (IHC) to guide treatment decisions for HER2/neu-based therapy are predicated upon the probability of the overexpression/increased concentrations of HER2/neu being correlated with the probability of a therapeutic response. Such expectation of a therapeutic response is not 100% certain, and is related to many factors, not the least of which is the diagnostic accuracy of the test utilized which, in turn, is also limited by the sampling of the tumor and various other factors (e.g., laboratory methodology/technique, reagent quality, and the like).

HER2/neu (also known as ErbB-2) is a protein which is associated with a higher level of "aggressiveness" in breast cancers. HER2/neu is a member of the ErbB protein family, more commonly known as the epidermal growth factor receptor family (EGFR). It is a cell membrane surface-bound receptor tyrosine kinase and is normally involved in the signal transduction pathways leading to cell growth and differentiation. The HER2 gene is a proto-oncogene located at the long arm of human chromosome 17(17q11.2-q12). See, e.g., Olayioye, M. A., et al., Update on HER-2 as a target for cancer therapy: intracellular signaling pathways of ErbB2/HER-2 and family members. *Breast Cancer Res.* 3:385-389 (2001). HER2/neu plays an important role in the pathogenesis of breast cancer and serves as a target of treatment. Approximately 15-20 percent of breast cancers have an amplification of the HER2/neu gene or overexpression of its protein product. Overexpression of HER2/neu in breast cancer is associated with increased disease recurrence and worse prognosis. Overexpression of HER2/neu has also been shown to occur in other cancer, e.g., ovarian and stomach cancers. Clinically, HER2/neu is important as the target of the monoclonal antibody trastuzumab (Herceptin). Because of its prognostic role as well as its ability to predict response to trastuzumab, breast tumors are routinely checked for overexpression of HER2/neu. Trastuzumab is only effective in breast cancer where the HER2/neu receptor is overexpressed. One of the mechanisms of how traztuzumab works after it binds to HER2 is by increasing p27, a protein that halts cell proliferation. See, e.g., Le, X. F., et al., HER2-targeting antibodies modulate the cyclin-dependent kinase inhibitor p27Kip1 via multiple signaling pathways. *Cell Cycle* 4: 87-95 (2005). HER2 gene overexpression can be suppressed by the amplification of other genes and the use of the drug Herceptin.

In another embodiment, the cancer of origin for treatment with the present invention is selected from the group consisting of any cancer which either: (i) overexpresses thioredoxin or glutaredoxin and/or (ii) exhibits evidence of thioredoxin-mediated or glutaredoxin-mediated resistance to the chemotherapeutic agent or agents being used to treat said patient with cancer.

In another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In one embodiment of the present invention, a composition for increasing survival time in a patient with non-small cell lung carcinoma is disclosed, wherein the non-small cell lung carcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with non-small cell lung carcinoma; is administered in a medically-sufficient dose to the patient with non-small cell lung carcinoma, either prior to, concomitantly with, or subsequent to the administration of a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance.

In another embodiment of the present invention, a composition for increasing survival time in a patient with adenocarcinoma is disclosed, wherein the adenocarcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with adenocarcinoma; is administered in a medically-sufficient dose to the patient with adenocarcinoma, either prior to, concomitantly with, or subsequent to the administration of a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance.

In another embodiment, the composition is a Formula (I) compound having the structural formula:

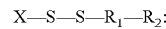

wherein;
$R_1$ is a lower alkylene, wherein $R_1$ is optionally substituted by a member of the group consisting of: lower alkyl, aryl, hydroxy, alkoxy, aryloxy, mercapto, alkylthio or arylthio, for a corresponding hydrogen atom, or

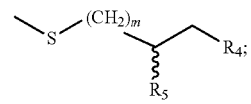

$R_2$ and $R_4$ is sulfonate or phosphonate;
$R_5$ is hydrogen, hydroxy, or sulfhydryl;
m is 0, 1, 2, 3, 4, 5, or 6; and
X is a sulfur-containing amino acid or a peptide consisting of from 2-10 amino acids;
or wherein X is a member of the group consisting of: lower thioalkyl (lower mercapto alkyl), lower alkylsulfonate, lower alkylphosphonate, lower alkenylsulfonate, lower alkyl, lower alkenyl, lower alkynyl, aryl, alkoxy, aryloxy, mercapto, alkylthio or hydroxy for a corresponding hydrogen atom; and
pharmaceutically-acceptable salts, prodrugs, analogs, conjugates, hydrates, solvates, polymorphs, stereoisomers (including diastereoisomers and enantiomers) and tautomers thereof.

In one embodiment of the present invention, the composition is a pharmaceutically-acceptable disodium salt of a Formula (I) compound. In various other embodiments, the composition of the present invention is/are a pharmaceutically-acceptable salt(s) of a Formula (I) compound which include, for example: (i) a monosodium salt; (ii) a sodium potassium salt; (iii) a dipotassium salt; (iv) a calcium salt; (v) a magnesium salt; (vi) a manganese salt; (vii) a monopotassium salt; and (viii) an ammonium salt. It should be noted that mono- and di-potassium salts of 2,2'-dithio-bis-ethane sulfonate and/or an analog thereof are administered to a subject if the total dose of potassium administered at any given point in time is not greater than 100 Meq. and the subject is not hyperkalemic and does not have a condition that would predispose the subject to hyperkalemia (e.g., renal failure).

In another embodiment of the present invention, the composition is disodium 2,2'-dithio-bis-ethane sulfonate (also known in the literature as Tavocept™, BNP7787, and dimesna).

In yet another embodiment, the composition is 2-mercapto-ethane sulfonate or 2-mercapto-ethane sulfonate conjugated as a disulfide with a substituent group selected from the group consisting of:

-Cys, -Homocysteine, -Cys-Gly, -Cys-Glu, -Homocysteine, -Homocysteine-Gly, -Homocysteine-Glu, -Cys-Glu,

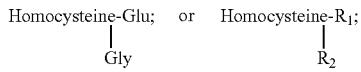

wherein $R_1$ and $R_2$ are any L- or D-amino acids.

In another embodiment, the chemotherapy agent or agents administered are selected from the group consisting of fluropyrimidines; pyrimidine nucleosides; purine nucleosides; anti-folates, platinum agents; anthracyclines/anthracenediones; epipodophyllotoxins; camptothecins; hormones; hormonal complexes; antihormonals; enzymes, proteins, peptides and polyclonal and/or monoclonal antibodies; vinca alkaloids; taxanes; epothilones; antimicrotubule agents; alkylating agents; antimetabolites; topoisomerase inhibitors; aziridine-containing compounds; antivirals; and various other cytotoxic and cytostatic agents.

In one embodiment of the present invention, the chemotherapy agent or agents are selected from the group consisting of: cisplatin, carboplatin, oxaliplatin, satraplatin, picoplatin, tetraplatin, platinum-DACH, and analogs and derivatives thereof.

In another embodiment, the chemotherapy agent or agents are selected from the group consisting of: docetaxel, paclitaxel, polyglutamylated forms of paclitaxel, liposomal paclitaxel, and analogs and derivatives thereof.

In yet another embodiment of the present invention, the chemotherapy agents are docetaxel and cisplatin.

The present invention additionally involves the use of the methods and the administration of the compositions described herein to a subject, optionally with or within a device, wherein the administration takes place as medically indicated in the subject prior to, concurrently or simultaneously, or following the administration of any chemotherapeutic agent or pharmaceutically active compound(s) by any route, dose, concentration, osmolarity, duration or schedule. Some of such routes, doses, concentrations, osmolarities, durations or schedules have been disclosed in U.S. patent application Ser. No. 11/638,193, entitled "CHEMOPROTECTIVE METHODS AND COMPOSITIONS", filed Dec. 13, 2006, the disclosure of which is hereby incorporated by reference in its entirety. Embodiments of the present invention also include controlled or other doses, dosage forms, formulations, compositions and/or devices containing one or more chemotherapeutic agents and a Formula (I) compound of the present invention, which include 2,2'-dithio-bis-ethane sulfonate, a pharmaceutically-acceptable salt, an analog thereof; mesna, a mesna heteroconjugate; and the various other Formula (I) compounds, including doses and dosage forms for: (i) oral (e.g., tablet, suspension, solution, gelatin capsule (hard or soft), sublingual, dissolvable tablet, troche, and the like); (ii) injection (e.g., subcutaneous administration, intradermal administration, subdermal administration, intramuscular administration, depot administration, intravenous administration, intra-arterial administration, and the like); (iii) intra-cavitary (e.g., into the intrapleural, intraperitoneal, intravesicular, and/or intrathecal spaces); (iv) per rectum (e.g., suppository, retention enema); and (v) topical administration routes.

Various chemotherapeutic agents may be used in conjunction with, or as a part of, the compositions, methods, and kits described and claimed herein. Chemotherapeutic agents may include, for example, a fluropyrimidine; a pyrimidine nucleoside; a purine nucleoside; an antifolate, a platinum analog; an anthracycline/anthracenedione; an epipodophyllotoxin; a camptothecin; a hormone; a hormonal analog; an antihormonal; an enzyme, protein, peptide, or polyclonal or monoclonal antibody; a vinca alkaloid; a taxane; an epothilone; an antimicrotubule agent; an alkylating agent; an antimetabolite; a topoisomerase inhibitor; an aziridine-containing compound; an antiviral; or another cytotoxic and/or cytostatic agent.

More specifically, fluropyrimidines include, for example, 5-fluorouracil (5-FU), S-1, capecitabine, ftorafur, 5'deoxyflurouridine, UFT, eniluracil, and the like. Pyrimidine nucleosides include, for example, cytarabine, deoxycytidine, 5-azacytosine, gemcitabine, 5-azadeoxycytidine, and the like. Purine nucleosides include, for example, fludarabine, 6-mercaptopurine, thioguanine, allopurinol, cladribine, and 2-chloro adenosine. Antifolates include, for example, methotrexate (MTX), pemetrexed (Alimta®), trimetrexate, aminopterin, methylene-10-deazaaminopterin (MDAM), and the like. Platinum analogs include those in which the platinum moiety can have a valence of II or IV and specifically include, for example, cisplatin, carboplatin, oxaliplatin, satraplatin, picoplatin, tetraplatin, platinum-DACH, and analogs thereof. Taxane medicaments include, for example, docetaxel or paclitaxel (including the commercially-available paclitaxel derivatives Taxol® and Abraxane®), polyglutamylated forms of paclitaxel (e.g., Xyotax®), liposomal paclitaxel (e.g., Tocosol®), and analogs and derivatives thereof. Anthracyclines/anthracenediones include, for example, doxorubicin, daunorubicin, epirubicin, and idarubicin. Epipodophyllotoxin derivatives include, for example, etoposide, etoposide phosphate and teniposide. Camptothecins include, for example, irinotecan, topotecan, 9-aminocamptothecin, 10, 11-methylenedioxycamptothecin, karenitecin, 9-nitrocamptothecin, and TAS 103. Hormones and hormonal analogs may include, for example, (i) estrogens and estrogen analogs, including anastrazole, diethylstilbesterol, estradiol, premarin, raloxifene; progesterone, progesterone analogs and progestins, including progesterone, norethynodrel, esthisterone, dimesthisterone, megestrol acetate, medroxyprogesterone acetate, hydroxyprogesterone caproate, and norethisterone; (ii) androgens, including fluoxymesterone, methyltestosterone and testosterone; and (iii) adrenocorticosteroids, including dexamthasone, prednisone, cortisol, solumedrol, and the like. Antihormones include, for example, (i) antiestrogens, including: tamoxifen, fulvestrant, toremifene; aminoglutethimide, testolactone, droloxifene, and anastrozole; (ii) antiandrogens, including: bicalutamide, flutamide, nilutamide, and goserelin; (iii) antitestosterones, including: flutamide, leuprolide, and triptorelin; and (iv) adrenal steroid inhibitors including: aminoglutethimide and mitotane; and anti-leuteinizing hormones, including goserelin. Enzymes, proteins, peptides, polyclonal and/or monoclonal antibodies, may include, for example, asparaginase, cetuximab, erlotinib, bevacizumab, rituximab, gefitinib, trastuzumab, interleukins, interferons, leuprolide, pegasparaginase, and the like. Vinca Alkaloids include, for example, vincristine, vinblastine, vinorelbine, vindesine, and the like. Alkylating agents may include, for example, dacarbazine; procarbazine; temozolamide; thiotepa, nitrogen mustards (e.g., mechlorethamine, chlorambucil, L-phenylalanine mustard, melphalan, and the like); oxazaphosphorines (e.g., ifosphamide, cyclophosphamide, mefosphamide, perfosfamide, trophosphamide and the like); alkyl sulfonates (e.g., busulfan); and nitrosoureas (e.g., carmustine, lomustine, semustine, and the like). Epothilones include, for example, epothilones A-E. Antimetabolites include, for example, tomudex and methotrexate, trimetrexate, aminopterin, pemetrexid, MDAM, 6-mercaptopurine, and 6-thioguanine Topoisomerase inhibitors include, for example, irinotecan, topotecan, karenitecin, amsacrine, etoposide, etoposide phosphate, teniposide, and doxorubicin, daunorubicin, and other analogs. Antiviral agents include, for example, acyclovir, valacyclovir, ganciclovir, amantadine, rimantadine, lamivudine, and zidovudine. Monoclonal antibody agents include, for example, bevacizumab, trastuzumab, rituximab, and the like, as well as growth inhibitors such as erlotinib, and the like. In general, cytostatic agents are mechanism-based agents that slow the progression of neoplastic disease.

Chemotherapeutic agents may be prepared and administered to subjects using methods known within the art. For example, paclitaxel may be prepared using methods described in U.S. Pat. Nos. 5,641,803, 6,506,405, and 6,753,006 and is administered as known in the art (see, e.g., U.S. Pat. Nos. 5,641,803, 6,506,405, and 6,753,006). Paclitaxel may be prepared for administration in a dose in the range of approximately 50 mg/m$^2$ and approximately 275 mg/m$^2$. Preferred doses include approximately 80 mg/m$^2$, approximately 135 mg/m$^2$ and approximately 175 mg/m$^2$.

Docetaxel may be prepared using methods described in U.S. Pat. No. 4,814,470 and is administered as known in the art (see, e.g., U.S. Pat. Nos. 4,814,470, 5,438,072, 5,698,582, and 5,714,512). Docetaxel may be prepared for administration in a dose in the range of approximately 30 mg/m$^2$ to approximately 100 mg/m$^2$. Preferred doses include approximately 55 mg/m$^2$, approximately 60 mg/m$^2$, approximately 75 mg/m$^2$, and approximately 100 mg/m$^2$.

Cisplatin may be prepared using methods described in U.S. Pat. Nos. 4,302,446, 4,322,391, 4,310,515, and 4,915,956 and is administered as known in the art (see, e.g., U.S. Pat. Nos. 4,177,263, 4,310,515, 4,451,447). Cisplatin may be prepared for administration in a dose in the range of approximately 30 mg/m$^2$ to approximately 120 mg/m$^2$ in a single dose or 15 mg/m$^2$ to approximately 20 mg/m$^2$ daily for five days. Preferred doses include approximately 50 mg/m$^2$, approximately 75 mg/m$^2$ and approximately 100 mg/m$^2$.

Carboplatin may be prepared using methods described in U.S. Pat. No. 4,657,927 and is administered as known in the art (see, e.g., U.S. Pat. No. 4,657,927). Carboplatin may be prepared for administration in a dose in the range of approximately 20 mg/kg to approximately 200 mg/kg. Preferred doses include approximately 300 mg/m$^2$ and approximately 360 mg/m$^2$. Other dosing may be calculated using a formula according to the manufacturer's instructions.

Oxaliplatin may be prepared using methods described in U.S. Pat. Nos. 5,290,961, 5,420,319, 5,338,874 and is administered as known in the art (see, e.g., U.S. Pat. No. 5,716,988). Oxaliplatin may be prepared for administration in a dose in the range of approximately 50 mg/m$^2$ to approximately 200 mg/m$^2$. Preferred doses include approximately 85 mg/m$^2$ and approximately 130 mg/m$^2$.

In one embodiment of the present invention, a method of increasing survival time in a patient with cancer is disclosed, wherein the cancer, either: (i) overexpresses thioredoxin or glutaredoxin and/or (ii) exhibits evidence of thioredoxin-mediated or glutaredoxin-mediated resistance to the chemotherapeutic agent or agents used to treat said patient with non-small cell lung carcinoma; wherein said method comprises the administration of a medically-sufficient dose of a Formula (I) compound to said patient with cancer either prior to, concomitantly with, or subsequent to the administration of a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance.

In another embodiment, the cancer of origin for treatment with the present invention is selected from the group consisting of any cancer which either: (i) overexpresses thioredoxin or glutaredoxin and/or (ii) exhibits evidence of thioredoxin-mediated or glutaredoxin-mediated resistance to the chemotherapeutic agent or agents being used to treat said patient with cancer.

In another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In another embodiment of the present invention, a method of increasing survival time in a patient with non-small cell lung carcinoma is disclosed, wherein the non-small lung carcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with non-small cell lung carcinoma; wherein said method comprises the administration of a medically-sufficient dose of a Formula (I) compound to said patient with non-small cell lung carcinoma either prior to, concomitantly with, or subsequent to the administration of a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance.

In yet another embodiment of the present invention, a method of increasing survival time in a patient with adenocarcinoma is disclosed, wherein the adenocarcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with adenocarcinoma; wherein said method comprises the administration of a medically-sufficient dose of a Formula (I) compound to said patient with adenocarcinoma either prior to, concomitantly with, or subsequent to the administration of a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance.

In one embodiment, the Formula (I) compound has the structural formula:

wherein;

$R_1$ is a lower alkylene, wherein $R_1$ is optionally substituted by a member of the group consisting of: lower alkyl, aryl, hydroxy, alkoxy, aryloxy, mercapto, alkylthio or arylthio, for a corresponding hydrogen atom, or

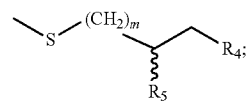

$R_2$ and $R_4$ is sulfonate or phosphonate;

$R_5$ is hydrogen, hydroxy, or sulfhydryl;

m is 0, 1, 2, 3, 4, 5, or 6; and

X is a sulfur-containing amino acid or a peptide consisting of from 2-10 amino acids;

or wherein X is a member of the group consisting of: lower thioalkyl (lower mercapto alkyl), lower alkylsulfonate, lower alkylphosphonate, lower alkenylsulfonate, lower alkyl, lower alkenyl, lower alkynyl, aryl, alkoxy, aryloxy, mercapto, alkylthio or hydroxy for a corresponding hydrogen atom; and pharmaceutically-acceptable salts, prodrugs, analogs, conjugates, hydrates, solvates, polymorphs, stereoisomers (including diastereoisomers and enantiomers) and tautomers thereof.

In one embodiment of the present invention, the composition is a pharmaceutically-acceptable disodium salt of a Formula (I) compound. In various other embodiments, the composition of the present invention is/are a pharmaceutically-acceptable salt(s) of a Formula (I) compound which include, for example: (i) a monosodium salt; (ii) a sodium potassium salt; (iii) a dipotassium salt; (iv) a calcium salt; (v) a magnesium salt; (vi) a manganese salt; (vii) a monopotassium salt; and (viii) an ammonium salt. It should be noted that mono- and di-potassium salts of 2,2'-dithio-bis-ethane sulfonate and/or an analog thereof are administered to a subject if the total dose of potassium administered at any given point in time is not greater than 100 Meq. and the subject is not hyperkalemic and does not have a condition that would predispose the subject to hyperkalemia (e.g., renal failure).

In another embodiment of the present invention, the composition is disodium 2,2'-dithio-bis-ethane sulfonate (also known in the literature as Tavocept™, BNP7787, and dimesna).

In yet another embodiment, the composition is 2-mercapto-ethane sulfonate or 2-mercapto-ethane sulfonate conjugated as a disulfide with a substituent group selected from the group consisting of:

-Cys, -Homocysteine, -Cys-Gly, -Cys-Glu, -Homocysteine, -Homocysteine-Gly, -Homocysteine-Glu, -Cys-Glu,

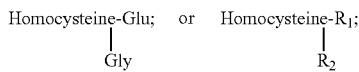

wherein $R_1$ and $R_2$ are any L- or D-amino acids.

In another embodiment, the chemotherapy agent or agents administered are selected from the group consisting of fluropyrimidines; pyrimidine nucleosides; purine nucleosides; anti-folates, platinum agents; anthracyclines/anthracenediones; epipodophyllotoxins; camptothecins; hormones; hormonal complexes; antihormonals; enzymes, proteins, peptides and polyclonal and/or monoclonal antibodies; vinca alkaloids; taxanes; epothilones; antimicrotubule agents; alkylating agents; antimetabolites; topoisomerase inhibitors; aziridine-containing compounds; antivirals; and various other cytotoxic and cytostatic agents.

In one embodiment of the present invention, the chemotherapy agent or agents are selected from the group consisting of: cisplatin, carboplatin, oxaliplatin, satraplatin, picoplatin, tetraplatin, platinum-DACH, and analogs and derivatives thereof.

In another embodiment, the chemotherapy agent or agents are selected from the group consisting of: docetaxel, paclitaxel, polyglutamylated forms of paclitaxel, liposomal paclitaxel, and analogs and derivatives thereof.

In yet another embodiment of the present invention, the chemotherapy agents are docetaxel and cisplatin.

In one embodiment of the present invention, a kit comprising a Formula (I) compound for administration, and instructions for administering said Formula (I) compound to a patient with cancer in an amount sufficient to cause an increase in the survival time of said patient with cancer who is receiving a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance, is disclosed.

In another embodiment, the cancer of origin for treatment with the present invention is selected from the group consisting of any cancer which either: (i) overexpresses thioredoxin or glutaredoxin and/or (ii) exhibits evidence of thioredoxin-mediated or glutaredoxin-mediated resistance to the chemotherapeutic agent or agents being used to treat said patient with cancer.

In another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In still another embodiment, the Formula (I) compound has the structural formula:

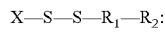

wherein;

$R_1$ is a lower alkylene, wherein $R_1$ is optionally substituted by a member of the group consisting of: lower alkyl, aryl, hydroxy, alkoxy, aryloxy, mercapto, alkylthio or arylthio, for a corresponding hydrogen atom, or

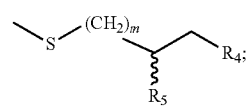

$R_2$ and $R_4$ is sulfonate or phosphonate;

$R_5$ is hydrogen, hydroxy, or sulfhydryl;

m is 0, 1, 2, 3, 4, 5, or 6; and

X is a sulfur-containing amino acid or a peptide consisting of from 2-10 amino acids;

or wherein X is a member of the group consisting of: lower thioalkyl (lower mercapto alkyl), lower alkylsulfonate, lower alkylphosphonate, lower alkenylsulfonate, lower alkyl, lower alkenyl, lower alkynyl, aryl, alkoxy, aryloxy, mercapto, alkylthio or hydroxy for a corresponding hydrogen atom; and pharmaceutically-acceptable salts, prodrugs, analogs, conjugates, hydrates, solvates, polymorphs, stereoisomers (including diastereoisomers and enantiomers) and tautomers thereof.

In one embodiment of the present invention, the Formula (I) compound is selected from the group consisting of: a disodium salt, a monosodium salt, a sodium potassium salt, a dipotassium salt, a monopotassium salt, a calcium salt, a magnesium salt, an ammonium salt, or a manganese salt.

In another embodiment, the Formula (I) compound is a disodium salt.

In yet another embodiment, the Formula (I) compound is disodium 2,2'-dithio-bis-ethane sulfonate.

In yet another embodiment, the composition is 2-mercapto-ethane sulfonate or 2-mercapto-ethane sulfonate conjugated as a disulfide with a substituent group selected from the group consisting of:
-Cys, -Homocysteine, -Cys-Gly, -Cys-Glu, -Homocysteine, -Homocysteine-Gly, -Homocysteine-Glu, -Cys-Glu,

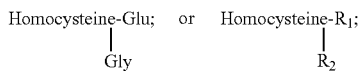

wherein $R_1$ and $R_2$ are any L- or D-amino acids.

In one embodiment, the chemotherapy agent or agents are selected from the group consisting of: fluropyrimidines; pyrimidine nucleosides; purine nucleosides; anti-folates, platinum agents; anthracyclines/anthracenediones; epipodophyllotoxins; camptothecins; hormones; hormonal complexes; antihormonals; enzymes, proteins, peptides and polyclonal and/or monoclonal antibodies; vinca alkaloids; taxanes; epothilones; antimicrotubule agents; alkylating agents; antimetabolites; topoisomerase inhibitors; aziridine-containing compounds; antivirals; and various other cytotoxic and cytostatic agents.

In another embodiment, the chemotherapy agent or agents are selected from the group consisting of: cisplatin, carboplatin, oxaliplatin, satraplatin, picoplatin, tetraplatin, platinum-DACH, and analogs and derivatives thereof.

In still another embodiment of the present invention, the chemotherapy agent or agents are selected from the group consisting of: docetaxel, paclitaxel, polyglutamylated forms of paclitaxel, liposomal paclitaxel, and analogs and derivatives thereof.

In one embodiment, the chemotherapy agents are docetaxel and cisplatin.

In another embodiment of the present invention, a kit comprising a Formula (I) compound for administration, and instructions for administering said Formula (I) compound to a patient with non-small cell lung carcinoma in an amount sufficient to cause an increase in the survival time of said patient who is receiving a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance, is disclosed.

In yet another embodiment, a kit comprising a Formula (I) compound for administration, and instructions for administering said Formula (I) compound to a patient with adenocarcinoma in an amount sufficient to cause an increase in the survival time of said patient who is receiving a chemotherapeutic agent or agents whose cytotoxic or cytostatic activity is adversely affected by either: (i) the overexpression of thioredoxin or glutaredoxin and/or (ii) the thioredoxin-mediated or glutaredoxin-mediated treatment resistance, is disclosed.

In one embodiment, the Formula (I) compound has the structural formula:

X—S—S—$R_1$—$R_2$:

wherein;

$R_1$ is a lower alkylene, wherein $R_1$ is optionally substituted by a member of the group consisting of: lower alkyl, aryl, hydroxy, alkoxy, aryloxy, mercapto, alkylthio or arylthio, for a corresponding hydrogen atom, or

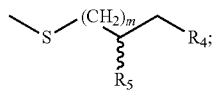

$R_2$ and $R_4$ is sulfonate or phosphonate;
$R_5$ is hydrogen, hydroxy, or sulfhydryl;
m is 0, 1, 2, 3, 4, 5, or 6; and
X is a sulfur-containing amino acid or a peptide consisting of from 2-10 amino acids;
or wherein X is a member of the group consisting of: lower thioalkyl (lower mercapto alkyl), lower alkylsulfonate, lower alkylphosphonate, lower alkenylsulfonate, lower alkyl, lower alkenyl, lower alkynyl, aryl, alkoxy, aryloxy, mercapto, alkylthio or hydroxy for a corresponding hydrogen atom; and pharmaceutically-acceptable salts, prodrugs, analogs, conjugates, hydrates, solvates, polymorphs, stereoisomers (including diastereoisomers and enantiomers) and tautomers thereof.

In one embodiment of the present invention, the composition is a pharmaceutically-acceptable disodium salt of a Formula (I) compound. In various other embodiments, the composition of the present invention is/are a pharmaceutically-acceptable salt(s) of a Formula (I) compound which include, for example: (i) a monosodium salt; (ii) a sodium potassium salt; (iii) a dipotassium salt; (iv) a calcium salt; (v) a magnesium salt; (vi) a manganese salt; (vii) a monopotassium salt; and (viii) an ammonium salt. It should be noted that mono- and di-potassium salts of 2,2'-dithio-bis-ethane sulfonate and/or an analog thereof are administered to a subject if the total dose of potassium administered at any given point in time is not greater than 100 Meq. and the subject is not hyperkalemic and does not have a condition that would predispose the subject to hyperkalemia (e.g., renal failure).

In another embodiment of the present invention, the composition is disodium 2,2'-dithio-bis-ethane sulfonate (also known in the literature as Tavocept™, BNP7787, and dimesna).

In yet another embodiment, the composition is 2-mercapto-ethane sulfonate or 2-mercapto-ethane sulfonate conjugated as a disulfide with a substituent group selected from the group consisting of:
-Cys, -Homocysteine, -Cys-Gly, -Cys-Glu, -Homocysteine, -Homocysteine-Gly, -Homocysteine-Glu, -Cys-Glu,

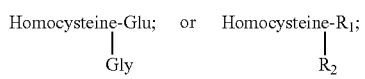

wherein $R_1$ and $R_2$ are any L- or D-amino acids.

In another embodiment, the chemotherapy agent or agents administered are selected from the group consisting of fluropyrimidines; pyrimidine nucleosides; purine nucleosides; anti-folates, platinum agents; anthracyclines/anthracenediones; epipodophyllotoxins; camptothecins; hormones; hormonal complexes; antihormonals; enzymes, proteins, peptides and polyclonal and/or monoclonal antibodies; vinca alkaloids; taxanes; epothilones; antimicrotubule agents; alkylating agents; antimetabolites; topoisomerase inhibitors; aziridine-containing compounds; antivirals; and various other cytotoxic and cytostatic agents.

In one embodiment of the present invention, the chemotherapy agent or agents are selected from the group consisting of: cisplatin, carboplatin, oxaliplatin, satraplatin, picoplatin, tetraplatin, platinum-DACH, and analogs and derivatives thereof.

In another embodiment, the chemotherapy agent or agents are selected from the group consisting of: docetaxel, paclitaxel, polyglutamylated forms of paclitaxel, liposomal paclitaxel, and analogs and derivatives thereof.

In yet another embodiment of the present invention, the chemotherapy agents are docetaxel and cisplatin.

In one embodiment of the present invention, a method for quantitatively ascertaining the level of thioredoxin or glutaredoxin DNA, mRNA, or protein in cells which have been isolated from a patient who is suspected of having cancer or has already been diagnosed with cancer is disclosed; wherein the method used to identify levels of thioredoxin or glutaredoxin is selected from the group consisting of: fluorescence in situ hybridization (FISH), nucleic acid microarray analysis, immunohistochemistry (IHC), and radioimmunoassay (RIA).

In another embodiment, the method is used in the initial diagnosis, the planning of subsequent treatment methodologies, and/or determining the potential aggressiveness of cancer growth in a patient suffering from a type of cancer in which the cells comprising the cancer either: (i) overexpress thioredoxin or glutaredoxin and/or (ii) exhibit evidence of thioredoxin-mediated or glutaredoxin-mediated treatment resistance to the chemotherapeutic agents or agents already being administered to the patient with cancer.

In another embodiment, the cancer of origin for treatment with the present invention is selected from the group consisting of any cancer which either: (i) overexpresses thioredoxin or glutaredoxin and/or (ii) exhibits evidence of thioredoxin-mediated or glutaredoxin-mediated resistance to the chemotherapeutic agent or agents being used to treat said patient with cancer.

In still another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In another embodiment of the present invention, a method for increasing survival time in a patient with cancer is disclosed, wherein said cancer, either: (i) overexpresses thioredoxin or glutaredoxin and/or (ii) exhibits evidence of thioredoxin-mediated or glutaredoxin-mediated resistance to the chemotherapeutic agent or agents used to treat said patient with cancer; wherein said method comprises the administration of a medically-sufficient dose of a Formula (I) compound to said patient with cancer either prior to, concomitantly with, or subsequent to the administration of the chemotherapeutic agents cisplatin and docetaxel; wherein the cytotoxic or cytostatic activity of the chemotherapeutic agents is adversely affected by either: (i) the overexpression of thioredoxin or glutaredoxin and/or (ii) the thioredoxin-mediated or glutaredoxin-mediated treatment resistance.

In another embodiment, the cancer of origin for treatment with the present invention is selected from the group consisting of any cancer which either: (i) overexpresses thioredoxin or glutaredoxin and/or (ii) exhibits evidence of thioredoxin-mediated or glutaredoxin-mediated resistance to the chemotherapeutic agent or agents being used to treat said patient with cancer.

In another embodiment, the cancer of origin for treatment with the present invention is selected from the group consisting of: lung cancer, colorectal cancer, gastric cancer, esophageal cancer, ovarian cancer, cancer of the biliary tract, gallbladder cancer, cervical cancer, breast cancer, endometrial cancer, vaginal cancer, prostate cancer, uterine cancer, hepatic cancer, pancreatic cancer, and adenocarcinoma.

In one embodiment of the present invention, a method for increasing survival time in a cancer patient with non-small cell lung carcinoma is disclosed, wherein the non-small cell lung carcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with non-small cell lung carcinoma; wherein said method comprises the administration of a medically-sufficient dose of a Formula (I) compound to said patient with non-small cell lung carcinoma either prior to, concomitantly with, or subsequent to the administration of the chemotherapeutic agents cisplatin and docetaxel; wherein the cytotoxic or cytostatic activity of said chemotherapeutic agents is adversely affected by either: (i) the overexpression of thioredoxin or glutaredoxin and/or (ii) the thioredoxin-mediated or glutaredoxin-mediated treatment resistance.

In another embodiment, a method for increasing survival time in a cancer patient with adenocarcinoma is disclosed, wherein the adenocarcinoma, either: (i) overexpresses thioredoxin or glutaredoxin and/or (ii) exhibits evidence of thioredoxin-mediated or glutaredoxin-mediated resistance to the chemotherapeutic agent or agents used to treat said patient with adenocarcinoma; wherein said method comprises the administration of a medically-sufficient dose of a Formula (I) compound to said patient with adenocarcinoma either prior to, concomitantly with, or subsequent to the administration of the chemotherapeutic agents cisplatin and docetaxel; wherein the cytotoxic or cytostatic activity of said chemotherapeutic agents is adversely affected by either: (i) the overexpression of thioredoxin or glutaredoxin and/or (ii) the thioredoxin-mediated or glutaredoxin-mediated treatment resistance.

In yet another embodiment, the method is comprised of: (i) the administration of docetaxel at a dose of 75 mg/m$^2$ which is given intravenously over a period of approximately 1 hour; (ii) the administration of docetaxel in step (i) is immediately followed by the administration of disodium 2,2'-dithio-bis-ethane sulfonate (Tavocept™) at a dose of approximately 40 grams which is given intravenously over a period of approximately 30 minutes; and (iii) the administration of disodium 2,2'-dithio-bis-ethane sulfonate (Tavocept™) in step (ii) is immediately followed by the administration of cisplatin at a dose of 75 mg/m$^2$ which is given intravenously over a period of approximately 1 hour with concomitant sufficient intravenous hydration; wherein steps (i)-(iii) constitute a single chemotherapy cycle which can be repeated every two weeks, for up to a total of six cycles.

In another embodiment, a kit comprising a Formula (I) compound for administration, and instructions for administering said Formula (I) compound to a patient with any medical condition or disease wherein there is overexpression of thioredoxin or glutaredoxin is disclosed, wherein said kit comprises the administration of a medically-sufficient dose of a Formula (I) compound overexpression, and wherein the overexpression of thioredoxin or glutaredoxin causes deleterious physiological effects in said patient.

Furthermore, in brief, the present invention discloses and claims: (i) compositions, methods, and kits which lead to an increase in patient survival time in cancer patients receiving chemotherapy; (ii) compositions and methods which cause cytotoxic or apoptotic potentiation of the anti-cancer activity of chemotherapeutic agents; (iii) compositions and methods for maintaining or stimulating hematological function in patients in need thereof, including those patients suffering from cancer; (iv) compositions and methods for maintaining or stimulating erythropoietin function or synthesis in patients in need thereof, including those patients suffering from cancer; (v) compositions and methods for mitigating or preventing anemia in patients in need thereof, including those patients suffering from cancer; (vi) compositions and methods for maintaining or stimulating pluripotent, multipotent, and unipotent normal stem cell function or synthesis in patients in need thereof, including those patients suffering from cancer; (vii) compositions and methods which promote the arrest or retardation of tumor progression in those cancer patients receiving chemotherapy; (viii) compositions and methods for increasing patient survival and/or delaying tumor progression while maintaining or improving the quality of life in a cancer patient receiving chemotherapy; (ix) novel methods of the administration of taxane and/or platinum medicaments and a Formula (I) compound of the present invention to a cancer patient; and (x) kits to achieve one or more of the aforementioned physiological effects in a patient in need thereof, including those patients suffering from cancer.

In one embodiment, a patient suffering from lung cancer treated with taxane and/or platinum medicaments is given a medically sufficient dosage of a Formula (I) compound so as to increase patient survival time in said patient suffering from lung cancer.

In another embodiment, the lung cancer is non-small cell lung carcinoma.

In another embodiment, the increase in patient survival time in said patient suffering from lung cancer and treated with a Formula (I) compound is expected to be at least 30 days longer than the expected survival time if said patient was not treated with a Formula (I) compound.

In yet another embodiment, a patient suffering from lung cancer was treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, a patient suffering from lung cancer was treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, a patient suffering from adenocarcinoma treated with taxane and/or platinum medicaments is given a medically sufficient dosage of a Formula (I) compound so as to increase patient survival time in said patient suffering from adenocarcinoma.

In another embodiment, the increase in patient survival time in said patient suffering from adenocarcinoma and treated with a Formula (I) compound is expected to be at least 30 days longer than the expected survival time if said patient was not treated with a Formula (I) compound.

In yet another embodiment, a patient suffering from adenocarcinoma is treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, a patient suffering from adenocarcinoma is treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, a patient suffering from lung cancer treated with taxane and platinum medicaments is given a medically sufficient dosage of a Formula (I) compound so as to potentiate the chemotherapeutic effect in said patient suffering from lung cancer.

In another embodiment, the lung cancer is non-small cell lung carcinoma.

In yet another embodiment, the chemotherapeutic effect is potentiated in a patient suffering from lung cancer treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, the chemotherapeutic effect is potentiated in a patient suffering from lung cancer treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, the chemotherapeutic effect is potentiated in a patient suffering from adenocarcinoma who is treated with taxane and platinum medicaments and is also given a medically sufficient dosage of a Formula (I) compound so as to increase patient survival time in said patient suffering from adenocarcinoma.

In yet another embodiment, the chemotherapeutic effect is potentiated in a patient suffering from adenocarcinoma treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, the chemotherapeutic effect is potentiated in a patient suffering from adenocarcinoma treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, hematological function is maintained or stimulated in a patient in need thereof, by providing to said patient a composition comprised of a Formula (I) compound in a medically sufficient dosage.

In one embodiment, a patient suffering from lung cancer treated with taxane and/or platinum medicaments is given a medically sufficient dosage of a Formula (I) compound so as to maintain or stimulate hematological function in said patient suffering from lung cancer.

In another embodiment, the lung cancer is non-small cell lung carcinoma.

In yet another embodiment, the hematological function is maintained or stimulated in a patient suffering from lung cancer treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, the hematological function is maintained or stimulated in a patient suffering from lung cancer treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, the hematological function is maintained or stimulated in a patient suffering from adenocarcinoma who is treated with taxane and/or platinum medicaments and is also given a medically sufficient dosage of a Formula (I) compound so as to maintain or stimulate hematological function in said patient suffering from adenocarcinoma.

In yet another embodiment, the hematological function is maintained or stimulated in a patient suffering from adenocarcinoma treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, the hematological function is maintained or stimulated in a patient suffering from adenocarcinoma treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, erythropoietin function or synthesis or homeostatic function of erythropoiesis is maintained or stimulated in a patient in need thereof, by providing to said patient a composition comprised of a Formula (I) compound in a medically sufficient dosage.

In one embodiment, a patient suffering from lung cancer treated with taxane and/or platinum medicaments is given a medically sufficient dosage of a Formula (I) compound so as to maintain or stimulate erythropoietin function or synthesis or homeostatic function of erythropoiesis in said patient suffering from lung cancer.

In another embodiment, the lung cancer is non-small cell lung carcinoma.

In yet another embodiment, the erythropoietin function or synthesis or homeostatic function of erythropoiesis is maintained or stimulated in a patient suffering from lung cancer treated with paclitaxel, a Formula (I) compound, and cisplatin once every 2-4 weeks, wherein the dose of paclitaxel ranged from approximately 160 mg/m$^2$ to approximately 190 mg/m$^2$, the dose of a Formula (I) compound ranged from approximately 14 g/m$^2$ to approximately 22 g/m$^2$, and the dose of cisplatin ranged from approximately 60 mg/m$^2$ to approximately 100 mg/m$^2$, wherein said administration of paclitaxel, a Formula (I) compound, and cisplatin once every 2-4 weeks was repeated at least once.

In still another embodiment, the erythropoietin function or synthesis or homeostatic function of erythropoiesis is maintained or stimulated in a patient suffering from lung cancer treated with paclitaxel, a Formula (I) compound, and cisplatin once every 3 weeks, wherein the dose of paclitaxel was approximately 175 mg/m$^2$, the dose of a Formula (I) compound was approximately 18.4 g/m$^2$, and the dose of cisplatin ranged from approximately 75 mg/m$^2$ to approximately 85 mg/m$^2$, wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, the erythropoietin function or synthesis or homeostatic function of erythropoiesis is maintained or stimulated in a patient suffering from adenocarcinoma who is treated with taxane and/or platinum medicaments and is also given a medically sufficient dosage of a Formula (I) compound so as to maintain or stimulate erythropoietin function or synthesis or homeostatic function of erythropoiesis in said patient suffering from adenocarcinoma.

In yet another embodiment, the erythropoietin function or synthesis or homeostatic function of erythropoiesis is maintained or stimulated in a patient suffering from adenocarcinoma treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, the erythropoietin function or synthesis or homeostatic function of erythropoiesis is maintained or stimulated in a patient suffering from adenocarcinoma treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, anemia is mitigated or prevented in a patient in need thereof, by providing to said patient a composition comprised of a Formula (I) compound in a medically sufficient dosage.

In one embodiment, a patient suffering from lung cancer treated with taxane and/or platinum medicaments is given a medically sufficient dosage of a Formula (I) compound so as to mitigate or prevent chemotherapy-induced anemia in said patient suffering from lung cancer.

In another embodiment, the lung cancer is non-small cell lung carcinoma.

In yet another embodiment, chemotherapy-induced anemia is mitigated or prevented in a patient suffering from lung cancer treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, chemotherapy-induced anemia is mitigated or prevented in a patient suffering from lung cancer treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, chemotherapy-induced anemia is mitigated or prevented in a patient suffering from adenocarcinoma who is treated with taxane and/or platinum medicaments and is also given a medically sufficient dosage of a Formula (I) compound so as to mitigate or prevent chemotherapy-induced anemia.

In yet another embodiment, chemotherapy-induced anemia is mitigated or prevented in a patient suffering from adenocarcinoma treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, chemotherapy-induced anemia is mitigated or prevented in a patient suffering from adenocarcinoma treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In one embodiment, pluripotent, multipotent, and unipotent normal stem cell function or synthesis is maintained or stimulated in a patient in need thereof, by providing to said patient a composition comprised of a Formula (I) compound in a medically sufficient dosage.

In one embodiment, a patient suffering from lung cancer treated with taxane and/or platinum medicaments is given a medically sufficient dosage of a Formula (I) compound so as to maintain or stimulate pluripotent, multipotent, and unipotent normal stem cell function or synthesis in said patient suffering from lung cancer.

In another embodiment, the lung cancer is non-small cell lung carcinoma.

In yet another embodiment, pluripotent, multipotent, and unipotent normal stem cell function or synthesis is maintained or stimulated in a patient suffering from lung cancer treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, pluripotent, multipotent, and unipotent normal stem cell function or synthesis is maintained or stimulated in a patient suffering from lung cancer treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from lung cancer were male or female and smokers or non-smokers.

In one embodiment, pluripotent, multipotent, and unipotent normal stem cell function or synthesis is maintained or stimulated in a patient suffering from adenocarcinoma who is treated with taxane and/or platinum medicaments and is also given a medically sufficient dosage of a Formula (I) compound so as to maintain or stimulate pluripotent, multipotent, and unipotent normal stem cell function or synthesis in said patient suffering from adenocarcinoma.

In yet another embodiment, pluripotent, multipotent, and unipotent normal stem cell function or synthesis is maintained or stimulated in a patient suffering from adenocarcinoma treated with paclitaxel, a Formula (I) compound, and cisplatin once every 2-4 weeks, wherein the dose of paclitaxel ranged from approximately 160 mg/m² to approximately 190 mg/m², the dose of a Formula (I) compound ranged from approximately 14 g/m² to approximately 22 g/m², and the dose of cisplatin ranged from approximately 60 mg/m² to approximately 100 mg/m², wherein said administration of paclitaxel, a Formula (I) compound, and cisplatin once every 2-4 weeks was repeated at least once.

In still another embodiment, pluripotent, multipotent, and unipotent normal stem cell function or synthesis is maintained or stimulated in a patient suffering from adenocarcinoma treated with paclitaxel, a Formula (I) compound, and cisplatin once every 3 weeks, wherein the dose of paclitaxel was approximately 175 mg/m², the dose of a Formula (I) compound was approximately 18.4 g/m², and the dose of cisplatin ranged from approximately 75 mg/m² to approximately 85 mg/m², wherein said administration of paclitaxel, a Formula (I) compound, and cisplatin once every 3 weeks was repeated for 6 cycles.

In another embodiment, the patients suffering from adenocarcinoma were male or female and smokers or non-smokers.

In another embodiment, the Formula (I) compounds increase patient survival and/or delay tumor progression while maintaining or improving the quality of life of said patients diagnosed with lung cancer who are being treated with the taxane and/or platinum medicaments of the present invention.

In another embodiment, the lung cancer is non-small cell lung carcinoma.

In another embodiment, the Formula (I) compounds increase patient survival and/or delay tumor progression while maintaining or improving the quality of life of said patients diagnosed with adenocarcinoma who are being treated with the taxane and/or platinum medicaments of the present invention.

In another embodiment, the patients suffering from adenocarcinoma were male or female and smokers or non-smokers.

In another embodiment, the platinum medicaments of the present invention include cisplatin, oxaliplatin, carboplatin, satraplatin, and derivatives and analogs thereof.

In another embodiment, the taxane medicament is selected from the group consisting of docetaxel, paclitaxel, paclitaxel derivatives, polyglutamylated forms of paclitaxel, liposomal paclitaxel, and derivatives and analogs thereof.

In still another embodiment, the compositions of Formula (I) include 2,2'-dithio-bis-ethane sulfonate, a pharmaceutically-acceptable salt thereof, and/or an analog thereof, as well as prodrugs, analogs, conjugates, hydrates, solvates and polymorphs, as well as stereoisomers (including diastereoisomers and enantiomers) and tautomers of such compounds.

In still another embodiment, the dose rate of the taxane and platinum medicaments ranged from approximately 10-20 mg/m²/day and the dose rate of a Formula (I) compound ranged from approximately 4.1-41.0 g/m² per day; the concentration of the taxane and platinum medicaments and/or Formula (I) compounds is at least 0.01 mg/mL; the infusion time of the taxane and platinum medicaments and/or Formula (I) compounds is from approximately 5 minutes to approximately 24 hours, and can be repeated as needed and tolerated in a given patient; the schedule of administration of the taxane and platinum medicaments and/or Formula (I) compounds is every 2-8 weeks.

In another embodiment, a kit comprising a Formula (I) compound for administration to a patient, and instructions for administering said Formula (I) compound in an amount sufficient to cause one or more of the physiological effects selected from the group consisting of: increasing patient survival time of said cancer patient receiving taxane and platinum medicaments; causing a cytotoxic or apoptotic potentiation of the chemotherapeutic effects of said taxane and platinum medicaments; maintaining or stimulating hematological function in said patient, including said patient with cancer receiving chemotherapy; maintaining or stimulating erythropoietin function or synthesis in said patient, including said patient with cancer receiving chemotherapy; mitigating or preventing anemia in said patient, including said patient with cancer receiving chemotherapy; maintaining or stimulating pluripotent, multipotent, and unipotent normal stem cell function or synthesis in said patient, including said patient with cancer receiving chemotherapy; promoting the arrest or retardation of tumor progression in said cancer patient receiving taxane and/or platinum medicaments; and/or increasing patient survival and/or delaying tumor progression while maintaining or improving the quality of life in said cancer patient receiving taxane and platinum medicaments.

In another embodiment, the cancer patient has lung cancer.

In yet another embodiment, the lung cancer is non-small cell lung cancer.

In still another embodiment, the cancer patient has an adenocarcinoma.

In one embodiment, the kit further contains instructions for administering a taxane medicament and a platinum medicament selected from the group consisting of cisplatin, oxaliplatin, carboplatin, satraplatin, and derivatives and analogs thereof.

In another embodiment, the kit further contains instructions for administering a platinum medicament and a taxane medicament selected from the group consisting of docetaxel, paclitaxel, polyglutamylated forms of paclitaxel, liposomal paclitaxel, and derivatives and analogs thereof.

In yet another embodiment, the platinum and taxane medicaments are cisplatin and paclitaxel.

Chemotherapeutic agents may be prepared and administered to subjects using methods known within the art. For example, paclitaxel may be prepared using methods described in U.S. Pat. Nos. 5,641,803, 6,506,405, and 6,753,006 and is administered as known in the art (see, e.g., U.S. Pat. Nos. 5,641,803, 6,506,405, and 6,753,006). Paclitaxel may be prepared for administration in a dose in the range of about 50 mg/m² to about 275 mg/m². Preferred doses include about 160 mg/m² to about 190 mg/m². The most preferred dose is about 175 mg/m².

Docetaxel may be prepared using methods described in U.S. Pat. No. 4,814,470 and is administered as known in the art (see, e.g., U.S. Pat. Nos. 4,814,470, 5,438,072, 5,698,582, and 5,714,512). Docetaxel may be prepared for administration in a dose in the range of about 30 mg/m² to about 100 mg/m². Preferred doses include about 55 mg/m², about 60 mg/m², about 75 mg/m², and about 100 mg/m².

Cisplatin may be prepared using methods described in U.S. Pat. Nos. 4,302,446, 4,322,391, 4,310,515, and 4,915,956 and is administered as known in the art (see, e.g., U.S. Pat. Nos. 4,177,263, 4,310,515, 4,451,447). Cisplatin may be prepared for administration in a dose in the range of about 30 mg/m² to about 120 mg/m² in a single dose. Preferred doses range from about 60 mg/m² to about 100 mg/m². The most preferred doses range from about 75 mg/m² to about 85 mg/m².

Carboplatin may be prepared using methods described in U.S. Pat. No. 4,657,927 and is administered as known in the art (see, e.g., U.S. Pat. No. 4,657,927). Carboplatin may be prepared for administration in a dose in the range of about 20 mg/kg and about 200 mg/kg. Preferred doses include about 300 mg/m$^2$ and about 360 mg/m$^2$. Other dosing may be calculated using a formula according to the manufacturer's instructions.

Oxaliplatin may be prepared using methods described in U.S. Pat. Nos. 5,290,961, 5,420,319, 5,338,874 and is administered as known in the art (see, e.g., U.S. Pat. No. 5,716,988). Oxaliplatin may be prepared for administration in a dose in the range of about 50 mg/m$^2$ and about 200 mg/m$^2$. Preferred doses include about 85 mg/m$^2$ and about 130 mg/m$^2$.

The compositions of Formula (I) include 2,2'-dithio-bis-ethane sulfonate, a pharmaceutically-acceptable salt thereof, and/or an analog thereof, as well as prodrugs, analogs, conjugates, hydrates, solvates and polymorphs, as well as stereoisomers (including diastereoisomers and enantiomers) and tautomers of such compounds. Pharmaceutically-acceptable salts of the present invention include, but are not limited to: (i) a monosodium salt; (ii) a sodium potassium salt; (iii) a dipotassium salt; (iv) a calcium salt; (v) a magnesium salt; (vi) a manganese salt; (vii) an ammonium salt; (viii) a monopotassium salt; and (ix) most preferably, disodium. It should be noted that mono- and di-potassium salts are only administered to a subject if the total dose of potassium administered at any given point in time is not greater than 100 Meq., the subject is not hyperkalemic, and/or the subject does not have a condition that would predispose the subject to hyperkalemia (e.g., renal failure).

By way of non-limiting example, disodium 2,2'-dithio-bis-ethane sulfonate (also referred to in the literature as dimesna, Tavocept™, and BNP7787) is a known compound and can be manufactured by methods known in the art. See, e.g., *J. Org. Chem.* 26:1330-1331 (1961); *J. Org. Chem.* 59:8239 (1994). In addition, various salts of 2,2'-dithio-bis-ethane sulfonate, as well as other dithioethers may also be synthesized as outlined in U.S. Pat. Nos. 5,808,160, 6,160,167 and 6,504,049. Compounds of Formula (I) may be manufactured as described in Published U.S. Patent Application 2005/0256055. The disclosures of these patents, patent applications, and published patent applications are incorporated herein by reference, in their entirety.

Preferred doses of the Formula (I) compounds of the present invention range from about 14 g/m$^2$ to about 22 g/m$^2$, with a most preferred dose of 18.4 g/m$^2$.

In certain of the methods of the invention, as well as in the uses of the compositions and formulations of the invention, the Formula (I) compound may be administered in conjunction with one or more chemotherapeutic agent, wherein each course being of a specified period dependent upon the specific chemotherapeutic agent or agents utilized. In conjunction with the inventions described and claimed herein, the treatment regimens may be comprised, for example, of two or more treatment courses, of five or more treatment courses, of six or more treatment courses, of seven or more treatment courses, of eight or more treatment courses, or of nine or more treatment courses. The treatment courses may also be continuous in nature.

The compositions and formulations of the present invention, alone or in combination with one or more chemotherapeutic agents, and instructions for their use, may be included in a form of packs or kits. Thus, the invention also includes kits comprising the compositions, formulations, and/or devices described herein with instructions for use. For example, a kit may comprise a Formula (I) compound of the present invention and instructions for administration. Kits may additionally comprise one or more chemotherapeutic agents with instructions for their use. Kits may also additionally comprise one or more pre-treatments as described herein and instructions for their use.

Aspects of the present invention also include controlled delivery or other doses, dosage forms, formulations, compositions and/or devices containing a Formula (I) compound of the present invention, which include, e.g., 2,2'-dithio-bis-ethane sulfonate, a pharmaceutically-acceptable salt or an analog thereof; or a mesna heteroconjugate; as well as one or more chemotherapeutic agents. These compositions are comprised of, for example, various doses and dosage forms for: (i) oral (e.g., tablet, suspension, solution, gelatin capsule (hard or soft), sublingual, dissolvable tablet, troche, and the like), or with sublingual administration which avoids first-pass metabolism through the liver (i.e., the cytochrome $P_{450}$ oxidase system); (ii) injection (e.g., subcutaneous administration, intradermal administration, subdermal administration, intramuscular administration, depot administration, intravenous administration, intra-arterial administration, and the like), wherein the administration may occur by, e.g., injection delivery, delivery via parenteral bolus, slow intravenous injection, and intravenous drip, and infusion devices (e.g., implantable infusion devices, both active and passive); (iii) intra-cavitary (e.g., into the intrapleural, intraperitoneal, intravesicular, and/or intrathecal spaces); (iv) per rectum (e.g., suppository, retention enema); and (v) topical administration routes to subjects as treatment for various cancers.

Examples of dosage forms suitable for injection of the compounds and formulations of the present invention include delivery via bolus such as single or multiple or continuous or constant administrations by intravenous injection, subcutaneous, subdermal, and intramuscular administration. These forms may be injected using syringes, pens, jet injectors, and internal or external pumps, with vascular or peritoneal access, for example. Syringes come in a variety sizes including 0.3, 0.5, 1, 2, 5, 10, 25 and 50 mL capacity. Needleless jet injectors are also known in the art and use a pressurized air to inject a fine spray of solution into the skin. Pumps are also known in the art. The pumps are connected by flexible tubing to a catheter, which is inserted into the tissue just below the skin. The catheter is left in place for several days at a time. The pump is programmed to dispense the necessary amount of solution at the proper times.

Examples of infusion devices for compounds and formulations of the present invention include infusion pumps containing a Formula (I) compound of the present invention to be administered at a desired rate and amount for a desired number of doses or steady state administration, and include implantable drug pumps.

Examples of implantable infusion devices for compounds and formulations of the invention include any solid form or liquid form in which the active agent is a solution, suspension or encapsulated within or dispersed throughout a biodegradable polymer or synthetic polymer, for example, silicone, polypropylene, silicone rubber, silastic or similar polymer.

Examples of controlled release drug formulations useful for delivery of the compounds and formulations of the invention are found in, for example, Sweetman, S. C. (Ed.)., *The Complete Drug Reference*, 33rd Edition, Pharmaceutical Press, Chicago, 2483 pp. (2002); Aulton, M. E. (Ed.), *Pharmaceutics: The Science of Dosage Form Design*. Churchill Livingstone, Edinburgh, 734 pp. (2000); and, Ansel, H. C., Allen, L. V. and Popovich, N. G., *Pharmaceutical*

*Dosage Forms and Drug Delivery Systems,* 7*th Ed.*, Lippincott, 676 pp. (1999). Excipients employed in the manufacture of drug delivery systems are described in various publications known to those skilled in the art including, for example, Kibbe, E. H., *Handbook of Pharmaceutical Excipients,* 3*rd Ed.*, American Pharmaceutical Association, Washington, 665 pp. (2000).

Further examples of dosage forms of the present invention primarily utilized with oral administration, include but are not limited to, modified-release (MR) dosage forms including delayed-release (DR) forms; prolonged-action (PA) forms; controlled-release (CR) forms; extended-release (ER) forms; timed-release (TR) forms; and long-acting (LA) forms. As previously stated, these formulations are often used with orally administered dosage forms, however these terms may be applicable to any of the dosage forms, formulations, compositions and/or devices described herein. These formulations delay and control total drug release for some time after drug administration, and/or drug release in small aliquots intermittently after administration, and/or drug release slowly at a controlled rate governed by the delivery system, and/or drug release at a constant rate that does not vary, and/or drug release for a significantly longer period than usual formulations.

Modified-release dosage forms of the present invention include dosage forms having drug release features based on time, course, and/or location which are designed to accomplish therapeutic or convenience objectives not offered by conventional or immediate-release forms. See, e.g., Bogner, R. H., Bioavailability and bioequivalence of extended-release oral dosage forms. *U.S. Pharmacist* 22:3-12 (1997). Extended-release dosage forms of the invention include, for example, as defined by the FDA, a dosage form that allows a reduction in dosing frequency to that represented by a conventional dosage form, e.g., a solution or an immediate-release dosage form.

For example, one embodiment provides extended-release formulations containing a Formula (I) compound of the present invention for parenteral administration. Extended rates of activity of a Formula (I) compound of the present invention following injection may be achieved in a number of ways, including the following: crystal or amorphous Formula (I) compound forms having prolonged dissolution characteristics; slowly dissolving chemical complexes of Formula (I) compound formulations; solutions or suspensions of a Formula (I) compound of the present invention in slowly absorbed carriers or vehicles (e.g., oleaginous); increased particle size of a Formula (I) compound of the present invention, in suspension; or, by injection of slowly eroding microspheres of said Formula (I) compounds (see, e.g., Friess, W., et al., Insoluble collagen matrices for prolonged delivery of proteins. *Pharmaceut. Dev. Technol.* 1:185-193 (1996)). For example, the duration of action of the various forms of insulin is based in part on its physical form (i.e., amorphous or crystalline), complex formation with added agents, and its dosage form (i.e., solution or suspension).

An acetate, phosphate, citrate, bicarbonate, glutamine or glutamate buffer may be added to modify pH of the final composition. Optionally a carbohydrate or polyhydric alcohol tonicifier and, a preservative selected from the group consisting of m-cresol, benzyl alcohol, methyl, ethyl, propyl and butyl parabens and phenol may also be added. Water for injection, tonicifying agents such as sodium chloride, as well as other excipients, may also be present, if desired. For parenteral administration, formulations may be isotonic or substantially isotonic to avoid irritation and pain at the site of administration. Alternatively, formulations for parenteral administration may also be hyperosmotic relative to normal mammalian plasma, as described herein.

The terms buffer, buffer solution and buffered solution, when used with reference to hydrogen-ion concentration or pH, refer to the ability of a solute/solvent system, particularly an aqueous solution, to resist a change in pH with the addition of acid or alkali, or upon dilution with a solvent, or both. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydroxyl ion added does not exceed the capacity of the buffer system to neutralize it. The buffer used in the practice of the present invention is selected from any of the following, for example, an acetate, phosphate, citrate, bicarbonate, glutamine, or glutamate buffer, with the most preferred buffer being a phosphate buffer.

Carriers or excipients can also be used to facilitate administration of the compositions and formulations of the invention. Examples of carriers and excipients include calcium carbonate, calcium phosphate, various sugars such as lactose, glucose, or sucrose, or types of starch, cellulose derivatives, gelatin, polyethylene glycols, and physiologically compatible solvents.

A stabilizer may be included in the formulations of the invention, but will generally not be needed. If included, however, a stabilizer useful in the practice of the invention is a carbohydrate or a polyhydric alcohol. The polyhydric alcohols include such compounds as sorbitol, mannitol, glycerol, xylitol, and polypropylene/ethylene glycol copolymer, as well as various polyethylene glycols (PEG) of molecular weight 200, 400, 1450, 3350, 4000, 6000, and 8000). The carbohydrates include, for example, mannose, ribose, trehalose, maltose, inositol, lactose, galactose, arabinose, or lactose.

The *United States Pharmacopeia* (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formulation, and their activity should be evaluated in the total formulation to ensure that a particular agent that is effective in one formulation is not ineffective in another. It is not uncommon to find that a particular agent will be effective in one formulation but not effective in another formulation.

A preservative is, in the common pharmaceutical sense, a substance that prevents or inhibits microbial growth and may be added to a pharmaceutical formulation for this purpose to avoid consequent spoilage of the formulation by microorganisms. While the amount of the preservative is not great, it may nevertheless affect the overall stability of the Formula (I) compound of the present invention. Preservatives include, for example, benzyl alcohol and ethyl alcohol. While the preservative for use in the practice of the invention can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%)

and ethyl or propyl or butyl (0.005%-0.03%) parabens. The parabens are lower alkyl esters of para-hydroxybenzoic acid. A detailed description of each preservative is set forth in "*Remington's Pharmaceutical Sciences*" as well as *Pharmaceutical Dosage Forms: Parenteral Medications, Vol. 1*, Avis, et al. (1992). For these purposes, the 2,2'-dithio-bis-ethane sulfonate, a pharmaceutically-acceptable salt thereof, an analog thereof, and/or a compound of Formula (I), may be administered parenterally (including subcutaneous injections, intravenous, intramuscular, intradermal injection or infusion techniques) in dosage unit formulations containing conventional non-toxic pharmaceutically acceptable carriers, adjuvants, and vehicles. In addition, formulations of the present invention designed for parenteral administration must be stable, sterile, pyrogen-free, and possess particulate levels and size within accepted levels.

If desired, the parenteral formulation may be thickened with a thickening agent such as a methylcellulose. The formulation may be prepared in an emulsified form, either water in oil or oil in water. Any of a wide variety of pharmaceutically-acceptable emulsifying agents may be employed including, for example, acacia powder, a non-ionic surfactant, or an ionic surfactant.

It may also be desirable to add suitable dispersing or suspending agents to the pharmaceutical formulation. These may include, for example, aqueous suspensions such as synthetic and natural gums, e.g., tragacanth, acacia, alginate, dextran, sodium carboxymethylcellulose, methylcellulose, polyvinyl-pyrrolidone, or gelatin.

It is possible that other ingredients may be present in the parenteral pharmaceutical formulation of the invention. Such additional ingredients may include wetting agents, oils (e.g., a vegetable oil such as sesame, peanut, or olive), analgesic agents, emulsifiers, antioxidants, bulking agents, tonicity modifiers, metal ions, oleaginous vehicles, proteins (e.g., human serum albumin, gelatin, or proteins) and a zwitterion (e.g., an amino acid such as betaine, taurine, arginine, glycine, lysine, or histidine). Such additional ingredients, of course, should not adversely affect the overall stability of the pharmaceutical formulation of the present invention.

Containers and kits are also a part of a composition and may be considered a component. Therefore, the selection of a container is based on a consideration of the composition of the container, as well as of the ingredients, and the treatment to which it will be subjected.

Suitable routes of parenteral administration include intramuscular, intravenous, subcutaneous, intraperitoneal, subdermal, intradermal, intraarticular, intrathecal, and the like. Mucosal delivery is also permissible. The dose and dosage regimen will depend upon the weight, health, disease type, and degree of disease severity within the subject. Regarding pharmaceutical formulations, see, *Pharmaceutical Dosage Forms: Parenteral Medications, Vol. 1, 2nd ed.*, Avis et al., Eds., Marcel Dekker, New York, N.Y. (1992).

In addition to the above means of achieving extended drug action, the rate and duration of delivery of a Formula (I) compound of the present invention, as well as one or more chemotherapeutic agents may be controlled by, e.g., using mechanically controlled drug infusion pumps.

The present invention, in part, provides infusion dose delivery formulations and devices, including but not limited to, implantable infusion devices for delivery of compositions and formulations of the invention. Implantable infusion devices may employ inert material such as the biodegradable polymers described above or synthetic silicones, for example, cylastic, silicone rubber or other commercially-available polymers manufactured and approved for such uses. The polymer may be loaded with a Formula (I) compound of the present invention and any excipients. Implantable infusion devices may also comprise the coating of, or a portion of, a medical device wherein the coating comprises the polymer loaded with a Formula (I) compound of the present invention, one or more chemotherapeutic agents, and any excipient. Such an implantable infusion device may be prepared as disclosed in U.S. Pat. No. 6,309,380 by coating the device with an in vivo biocompatible and biodegradable or bioabsorbable or bioerodable liquid or gel solution containing a polymer with the solution comprising a desired dosage amount of a Formula (I) compound of the present invention, one or more chemotherapeutic agents, and any excipients. The solution is converted to a film adhering to the medical device thereby forming the implantable Formula (I) compound-deliverable medical device.

An implantable infusion device may also be prepared by the in situ formation of a Formula (I) compound of the present invention, containing a solid matrix (as disclosed in U.S. Pat. No. 6,120,789, the disclosure of which is hereby incorporated by reference, in its entirety) and one or more chemotherapeutic agents. Implantable infusion devices may be passive or active. An active implantable infusion device may comprise a Formula (I) compound reservoir, a means of allowing the Formula (I) compound to exit the reservoir, for example a permeable membrane, and a driving force to propel the Formula (I) compound from the reservoir. The reservoir of the aforementioned active implantable infusion device may also contain one or more chemotherapeutic agents. Such an active implantable infusion device may additionally be activated by an extrinsic signal, such as that disclosed in WO 02/45779, wherein the implantable infusion device comprises a system configured to deliver a Formula (I) compound of the present invention and one or more chemotherapeutic agents, comprising an external activation unit operable by a user to request activation of the implantable infusion device, including a controller to reject such a request prior to the expiration of a lockout interval. Examples of an active implantable infusion device include implantable drug pumps. Implantable drug pumps include, for example, miniature, computerized, programmable, refillable drug delivery systems with an attached catheter that inserts into a target organ system, usually the spinal cord or a vessel. See, Medtronic Inc. Publications: UC9603124EN NP-2687, 1997; UC199503941b EN NP-2347 182577-101, 2000; UC199801017a EN NP3273a 182600-101, 2000; UC200002512 EN NP4050, 2000; UC199900546bEN NP-3678EN, 2000. Medtronic, Inc., Minneapolis, Minn. (1997-2000). Many pumps have 2 ports: one into which drugs can be injected and the other that is connected directly to the catheter for bolus administration or analysis of fluid from the catheter. Implantable drug infusion pumps (e.g., SynchroMed EL and SynchroMed programmable pumps; Medtronic) are indicated for long-term intrathecal infusion of morphine sulfate for the treatment of chronic intractable pain; intravascular infusion of floxuridine for treatment of primary or metastatic cancer; intrathecal injection (baclofen injection) for severe spasticity; long-term epidural infusion of morphine sulfate for treatment of chronic intractable pain; long-term intravascular infusion of doxorubicin, cisplatin, or methotrexate for the treatment or metastatic cancer; and long-term intravenous infusion of clindamycin for the treatment of osteomyelitis. Such pumps may also be used for the long-term infusion of one or more compounds simultaneously, including, a Formula (I) compound of the present invention, in combination with one or more chemotherapeutic agents of choice, at a desired amount for a desired number of doses or steady state administration. One form of a typical implantable drug infusion pump (e.g., SynchroMed EL programmable pump; Medtronic) is titanium covered and roughly disk shaped, measures 85.2 mm in diameter and 22.86 mm in thickness, weighs 185 g, has a drug reservoir of 10 mL, and runs on a lithium thionyl-chloride battery with a 6- to 7-year life, depending on use. The downloadable memory contains programmed drug delivery parameters and calculated amount of drug remaining, which can be compared with actual amount of drug remaining to access accuracy of pump function, but actual pump function over time is not recorded. The pump is usually implanted in the right or left abdominal wall. Other pumps useful in the present invention include, for example, Portable Disposable Infuser Pumps (PDIPs). Additionally, implantable infusion devices may employ liposome delivery systems, such as a small unilamellar vesicles, large unilamellar vesicles, and multilamellar vesicles that can be formed from a variety of phospholipids, such as cholesterol, stearyl amine, or phosphatidylcholines.

The present invention also provides in part dose delivery formulations and devices formulated to enhance bioavailability of a Formula (I) compound of the present invention. This may be in addition to, or in combination with, one or more chemotherapeutic agents, or any of the formulations and/or devices described above.

For example, an increase in bioavailability of a Formula (I) compound of the present invention, may be achieved by complexation of a Formula (I) compound with one or more bioavailability or absorption enhancing agents or formulations, including bile acids such as taurocholic acid.

The present invention also provides for the formulation of an oxidative metabolism-affecting Formula (I) compound of the present invention, as well as one or more chemotherapeutic agents, in a microemulsion to enhance bioavailability. A microemulsion is a fluid and stable homogeneous solution composed of four major constituents, respectively, a hydrophilic phase, a lipophilic phase, at least one surfactant (SA) and at least one cosurfactant (CoSA). A surfactant is a chemical compound possessing two groups, the first polar or ionic, which has a great affinity for water, the second which contains a longer or shorter aliphatic chain and is hydrophobic. These chemical compounds having marked hydrophilic character are intended to cause the formation of micelles in aqueous or oily solution. Examples of suitable surfactants include mono-, di- and triglycerides and polyethylene glycol (PEG) mono- and diesters. A cosurfactant, also sometimes known as "co-surface-active agent", is a chemical compound having hydrophobic character, intended to cause the mutual solubilization of the aqueous and oily phases in a microemulsion. Examples of suitable co-surfactants include ethyl diglycol, lauric esters of propylene glycol, oleic esters of polyglycerol, and related compounds.

Any such dose may be administered by any of the routes or in any of the forms herein described. For example, a dose or doses could be given parenterally using a dosage form suitable for parenteral administration which may incorporate features or compositions described in respect of dosage forms delivered in a modified release, extended release, delayed release, slow release or repeat action oral dosage form.

The present invention also provides for the formulation of an oxidative metabolism-affecting Formula (I) compound of the present invention, for rectal delivery and absorption via the utilization of rectal suppositories or retention enemas. Generally, suppositories are utilized for delivery of drugs to the rectum and sigmoid colon. The ideal suppository base for the delivery of the formulations of the present invention should meet the following specifications: (i) a base which is non-toxic and non-irritating to the anal mucous membranes; (ii) a base which is compatible with a variety of drugs; (iii) a base which melts or dissolves in rectal fluids; and (iv) a base which is stable in storage and does not bind or otherwise interfere with the release and/or absorption of the pharmaceutical formulations contained therein. Typical suppository bases include: cocoa butter, glycerinated gelatine, hydrogenated vegetable oils, mixtures of polyethylene glycols of various molecular weights and fatty acid esters of polyethylene glycol. The rectal Epithelium is lipoidal in character. The lower, middle, and upper hemorrhoidal veins surrounds the rectum. Only the upper vein conveys blood into the portal system, thus drugs absorbed into the lower and middle hemorrhoidal veins will bypass the liver and the cytochrome $P_{450}$ oxidase system. Absorption and distribution of a drug is therefore modified by its position within the rectum, in that at least a portion of the drug absorbed from the rectum may pass directly into the inferior vena cava, bypassing the liver. The present invention also provides for the formulation of a Formula (I) compound of the present invention, as well as one or more chemotherapeutic agents, administered by suppository.

Various representative Formula (I) compounds of the present invention have been synthesized and purified. Additionally, disodium 2,2'-dithio-bis ethane sulfonate (also referred to in the literature as Tavocept™, dimesna, and BNP7787), has been introduced into Phase I, Phase II, and Phase III clinical testing in patients, as well as in nonclinical testing, by the Assignee, BioNumerik Pharmaceuticals, Inc., with guidance provided by the Applicant of the instant invention and in a U.S. Phase II NSCLC Clinical Trial, whose resulting data was further analyzed by the Assignee, BioNumerik Pharmaceuticals, Inc., again with guidance provided by the Applicant of the instant invention. For example, the data from the Japan Phase III Clinical Trial and the U.S. Phase II Clinical Trial utilizing disodium 2,2'-dithio-bis ethane sulfonate (Tavocept™) with one or more chemotherapeutic agents have demonstrated the ability of disodium 2,2'-dithio-bis ethane sulfonate to markedly increase the survival time of individuals with non-small cell lung carcinoma (NSCLC), including adenocarcinoma. In brief, experimental evidence supports the finding that disodium 2,2'-dithio-bis ethane sulfonate functions to increase patient survival time by increasing oxidative metabolism within tumor cells in a selective manner. Moreover, these clinical results have also demonstrated the ability of disodium 2,2'-dithio-bis ethane sulfonate to reduce both the frequency and severity of deleterious chemotherapeutic agent-induced physiological side effects and pharmacological effects on normal (i.e., non-cancerous) cells and tissues, while concomitantly avoiding any diminution of the cytotoxic effect of the chemotherapeutic agent in cancer cells.

V. Pharmacology of Taxanes

Taxanes are semi-synthetically derived analogues of naturally occurring compounds derived from plants. In particular, taxanes are derived from the needles and twigs of the European yew (*Taxus baccata*), or the bark of the Pacific yew (*Taxus brevifolia*). The most widely known taxanes at this time are paclitaxel (Taxol®) and docetaxel (Taxotere®), which are widely distributed as antineoplastic agents.

Paclitaxel was discovered in the late 1970s, and was found to be an effective antineoplastic agent with a mechanism of action different from then-existing chemotherapeutic agents. Taxanes are recognized as effective agents in the treatment of many solid tumors which are refractory to other antineoplastic agents.

Paclitaxel has the molecular structure shown below as Formula (A):

Formula (A)

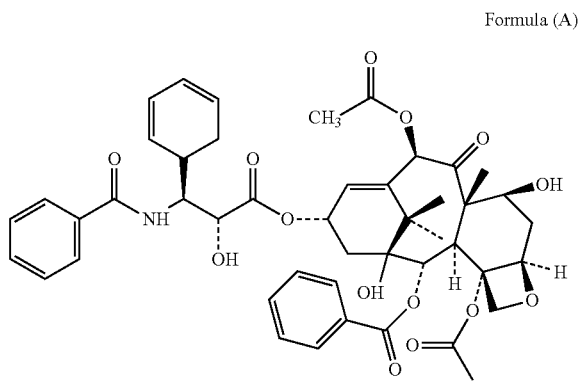

Docetaxel is an analog of Paclitaxel, and has the molecular structure shown below as Formula (B):

Formula (B)

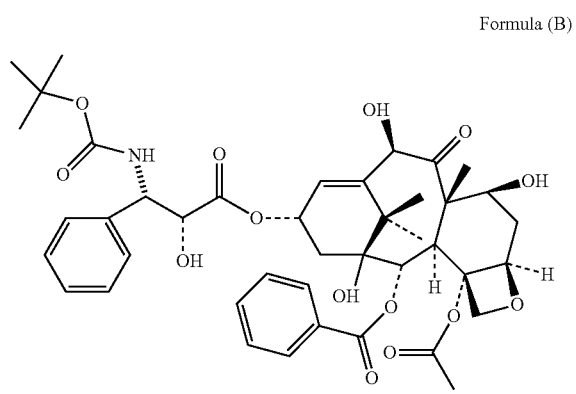

Taxanes exert their biological effects on the cell microtubules and act to promote the polymerization of tubulin, a protein subunit of spindle microtubules. The end result is the inhibition of depolymerization of the microtubules, which causes the formation of stable and nonfunctional microtubules. This disrupts the dynamic equilibrium within the microtubule system, and arrests the cell cycle in the late $G_2$ and M phases, which inhibits cell replication.

Taxanes interfere with the normal function of microtubule growth and arrests the function of microtubules by hyperstabilizes their structure. This destroys the cell's ability to use its cytoskeleton in a flexible manner.

Taxanes function as an anti-neoplastic agent by binding to the N-terminal 31 amino acid residues of the β-tubulin subunit in tubulin oligomers or polymers, rather than tubulin dimers. Unlike other anti-microtubule agents (e.g., vinca alkaloids) which prevent microtubule assembly, submicromolar concentrations of taxanes function to decrease the lag-time and shift the dynamic equilibrium between tubulin dimers and microtubules (i.e., the hyperpolymerization of tubulin oligomers) toward microtubules assembly and stabilize the newly formed microtubules against depolymerization. The microtubules which are formed are highly stable, thereby inhibiting the dynamic reorganization of the microtubule network. See, e.g., Rowinsky, E. K., et al., Taxol: The prototypic taxane, an important new class of antitumor agents. *Semin. Oncol.* 19:646 (1992). Tubulin is the "building block" of microtubules, the resulting microtubule/taxane complex does not have the ability to disassemble. Thus, the binding of taxanes inhibit the dynamic reorganization of the microtubule network. This adversely affects cell function because the shortening and lengthening of microtubules (i.e., dynamic instability) is necessary for their function as a mechanism to transport other cellular components. For example, during mitosis, microtubules position the chromosomes during their replication and subsequent separation into the two daughter-cell nuclei.

In addition, even at submicromolar concentrations, the taxanes also induce microtubule bundling in cells, as well as the formation of numerous abnormal mitotic asters (which unlike mitotic asters formed under normal physiological conditions, do not require centrioles for enucleation. Thus, the taxanes function to inhibit the proliferation of cells by inducing a sustained mitotic "block" at the metaphase-anaphase boundary at a much lower concentration than that required to increase microtubule polymer mass and microtubule bundle formation. See, e.g., Rao, S., et al., Direct photoaffinity labeling of tubulin with taxol. *J. Natl. Cancer Inst.* 84:785 (1992). It should be noted that many of the deleterious physiological side-effects caused by the taxanes are caused by the sustained mitotic "block" at the metaphase-anaphase boundary in normal (i.e., non-neoplastic cells).

In addition to stabilizing microtubules, the taxane, paclitaxel, may act as a "molecular sponge" by sequestering free tubulin, thus effectively depleting the cells supply of tubulin monomers and/or dimers. This activity may trigger the aforementioned apoptosis. One common characteristic of most cancer cells is their rapid rate of cell division. In order to accommodate this, the cytoskeleton of the cancer cell undergoes extensive restructuring. Paclitaxel is an effective treatment for aggressive cancers because it adversely affects the process of cell division by preventing this restructuring. Although non-cancerous cells are also adversely affected, the rapid division rate of cancer cells make them far more susceptible to paclitaxel treatment.

Further research has also indicated that paclitaxel, induces programmed cell death (apoptosis) in cancer cells by binding to an apoptosis stopping protein called B-cell leukemia 2 (Bcl-2), thus arresting its function.

The molecular structure of the taxanes are complex alkaloid esters consisting of a taxane system linked to a four-member oxetan ring at positions C-4 and C-5. The taxane rings of both paclitaxel and docetaxel, but not 10-deacetyl-baccatin III, are linked to an ester at the C-13 position. Experimental and clinical studies have demonstrated that analogs lacking the aforementioned linkage have very little activity against mammalian tubulin. Moreover, the moieties at C-2' and C-3' are critical with respect to its full biological activity, specifically, for the anti-microtubule hyperpolymerization effect of taxane. The C-2' —OH is of paramount importance for the activity of taxol and the Formula (I) compounds of the present invention, and while the C-2' —OH of taxol can be "substituted" by a sufficiently strong nucleophile (see, PCT/US98/21814; page 62, line 8-27) the biological activity would be greatly diminished. See, e.g., Lataste, H., et al., Relationship between the structures of Taxol and baccatine III derivatives and their in vitro action of the disassembly of mammalian brain. *Proc. Natl. Acad. Sci.* 81:4090 (1984). For example, it has been demonstrated that the substitution of an acetyl group at the C-2' position markedly reduces taxane activity. See, e.g., Gueritte-Voegelein, F., et al., Relationships between the structures of taxol analogues and their antimitotic activity. *J. Med. Chem.* 34:992 (1991).

Taxanes are toxic compounds having a low therapeutic index which have been shown to cause a number of different toxic effects in patients. The most well-known and severe adverse effects of taxanes are neurotoxicity and hematologic toxicity, particularly anemia and severe neutropenia/thrombocytopenia. Additionally, taxanes also cause hypersensitivity reactions in a large percentage of patients; gastrointestinal effects (e.g., nausea, diarrhea and vomiting); alopecia; anemia; and various other deleterious physiological effects, even at the recommended dosages. The Taxane medicaments disclosed in the present invention include, in a non-limiting manner, docetaxel or paclitaxel (including the commercially-available paclitaxel derivatives Taxol® and Abraxane®), polyglutamylated forms of paclitaxel (e.g., Xyotax®), liposomal paclitaxel (e.g., Tocosol®), and analogs and derivatives thereof.

VI. Pharmacology of Platinum Compounds

The anti-neoplastic drug cisplatin (cis-diamminedichloroplatinum or "CDDP"), and related platinum based drugs including carboplatin and oxaliplatin, are widely used in the treatment of a variety of malignancies including, but not limited to, cancers of the ovary, lung, colon, bladder, germ cell tumors and head and neck. Platinum agents are reported to act, in part, by aquation (i.e., to form reactive aqua species), some of which may predominate intracellularly, and subsequently form DNA intra-strand coordination chelation cross-links with purine bases, thereby cross-linking DNA. The currently accepted paradigm with respect to cisplatin's mechanism of action is that the drug induces its cytotoxic properties by forming a reactive monoaquo species that reacts with the $N^7$ nitrogen contained within the imidazole components of guanine and adenosine found in nuclear DNA to form intrastrand platinum-DNA adducts. However, the exact mechanism of action of cisplatin is not completely understood and remains a subject of research interest within the scientific community. Thus, this mechanism is believed to work predominantly through intra-strand cross-links, and less commonly, through inter-strand cross-links, thereby disrupting the DNA structure and function, which is cytotoxic to cancer cells. Platinum-resistant cancer cells are resilient to the cytotoxic actions of these agents. Certain cancers exhibit intrinsic de novo natural resistance to the killing effects of platinum agents and undergo no apoptosis, necrosis or regression following initial platinum compound treatment. In contrast, other types of cancers exhibit cytotoxic sensitivity to platinum drugs, as evidenced by tumor regression following initial treatment, but subsequently develop an increasing level of platinum resistance, which is manifested as a reduced responsiveness and/or tumor growth following treatment with the platinum drug (i.e., "acquired resistance"). Accordingly, new platinum agents are continually being sought which will effectively kill tumor cells, but that are also insensitive or less susceptible to tumor-mediated drug resistance mechanisms that are observed with other platinum agents.

The reaction for cisplatin hydrolysis is illustrated below in Scheme I:

Scheme I

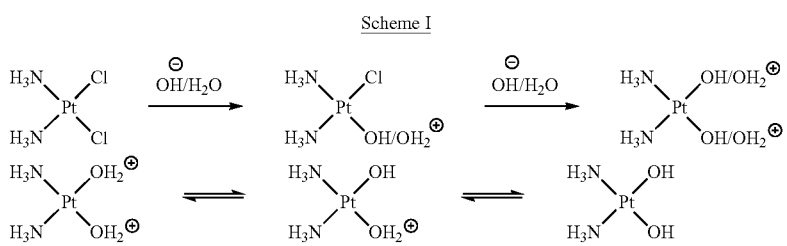

In neutral pH (i.e., pH 7), deionized water, cisplatin hydrolyze to monoaqua/monohydroxy platinum complexes, which is less likely to further hydrolyze to diaqua complexes. However, cisplatin can readily form monoaqua and diaqua complexes by precipitation of chloro ligand with inorganic salts (e.g., silver nitrate, and the like). Also, the chloro ligands can be replaced by existing nucleophile (e.g., nitrogen and sulfur electron donors, etc.) without undergoing aquation intermediates.

Cisplatin is relatively stable in human plasma, where a high concentration of chloride prevents aquation of cisplatin. However, once cisplatin enters a tumor cell, where a much lower concentration of chloride exists, one or both of the chloro ligands of cisplatin is displaced by water to form an aqua-active intermediate form (as shown above), which in turn can react rapidly with DNA purines (i.e., Adenine and Guanine) to form stable platinum-purine-DNA adducts.

Cisplatin enters the cell through both passive diffusion and active transport. The pharmacological behavior of cisplatin is in part determined by hydrolysis reactions that occur once cisplatin is inside the cell where the chloride concentration is essentially zero. In this intracellular milieu, one chlorine ligand is replaced by a water molecule to yield an aquated version of cisplatin. The aquated platinum can then react with a variety of intracellular nucleophiles. Cisplatin binds to RNA more extensively than to DNA and to DNA more extensively than to protein; however, all of these reactions are thought to occur intracellularly. Thus, upon administration, a chloride ligand undergoes slow displacement with water (an aqua ligand) molecules, in a process termed aquation. The aqua ligand in the resulting $[PtCl(H_2O)(NH_3)_2]^+$ is easily displaced, allowing cisplatin to coordinate a basic site in DNA. Subsequently, the platinum cross-links two bases via displacement of the other chloride ligand. Cisplatin crosslinks DNA in several different ways, interfering with cell division by mitosis. The damaged DNA elicits various DNA repair mechanisms, which in turn activate apoptosis when repair proves impossible. Most notable among the DNA changes are the 1,2-intrastrand cross-links with purine bases. These include 1,2-intrastrand d(GpG)

adducts which form nearly 90% of the adducts and the less common 1,2-intrastrand d(ApG) adducts. 1,3-intrastrand d(GpXpG) adducts may also occur, but are readily excised by the nucleotide excision repair (NER) mechanism. Other adducts include inter-strand crosslinks and nonfunctional adducts that have been postulated to contribute to cisplatin's activity. In some cases, replicative bypass of the platinum 1, 2-d(GpG) crosslink can occur allowing the cell to faithfully replicate its DNA in the presence of the platinum cross link, but often if this 1,2-intrastrand d(GpG) crosslink is not repaired, it interferes with DNA replication ultimately resulting in apoptosis.

The formation of cisplatin-DNA adducts that interfere with DNA replication is illustrated in Scheme II:

Scheme II

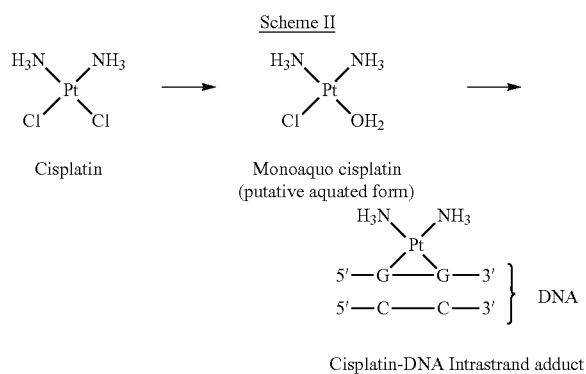

Cisplatin-DNA Intrastrand adduct

Interaction with cellular proteins, particularly High Mobility Group (HMG) chromosomal domain proteins (which are involved with transcription, replication, recombination, and DNA repair), has also been advanced as a mechanism of interfering with mitosis, although this is probably not its primary method of action. It should also be noted that although cisplatin is frequently designated as an alkylating agent, it has no alkyl group and cannot carry out alkylating reactions. Accordingly, it is more accurately classified as an alkylating-like agent.

Bu way of non-limiting example, the platinum compounds of the present invention include all compounds, compositions, and formulations which containing a platinum ligand in the structure of the molecule. The valence of the platinum ligand contained therein may be platinum II or platinum IV. The platinum medicaments of the present invention include, in a non-limiting manner, cisplatin, oxaliplatin, carboplatin, satraplatin, and analogs and derivatives thereof.

VII. Pharmacology of Formula (I) Compounds

The Formula (I) compounds, most notably for purposes of the present invention, dimesna (disodium-2,2'-dithiobis ethane sulfonate; BNP7787; Tavocept™) and the metabolite of dimesna, sodium-2-mercaptoethane sulfonate (mesna), act to selectively reduce the toxicity of certain antineoplastic agents in vivo. Mesna is utilized to reduce the acrolein related uroepithelial cell toxicity of ifosfamide and cyclophosphamide, and is currently approved for such usage in the United States and abroad.

Dimesna is the physiological auto-oxidation dimer of mesna. Mesna (I) and dimesna (II) have the following molecular structures:

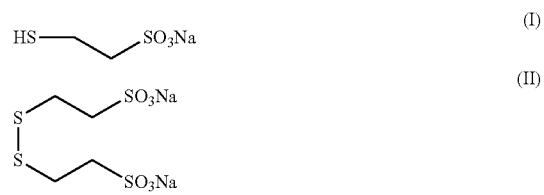

The pharmaceutical chemistry of the compounds indicates that the terminal sulfhydryl group of mesna (and to a lesser extent the disulfide linkage in dimesna) acts as a substitution group for the terminal hydroxy- or aquo-moiety in the active metabolites of platinum complexes. Dimesna, unlike mesna, requires a metabolic activation, such as by glutathione reductase, to exert its biologically efficacious results. Dimesna also exhibits significantly lower toxicity than mesna.

The conversion from the hydroxy- or aquo-moiety to a thioether is favored, particularly under acidic conditions, and results in the formation of a hydrophilic compound of much lower toxicity, one which is rapidly eliminated from the body.

Since blood plasma is slightly alkaline (pH~7.3), the more stable disulfide form is the favored species, and does not readily react with the nucleophilic terminal chlorine in cisplatin or the cyclobutane dicarboxylato moiety of carboplatin. This allows the drug to perform its intended cytotoxic action on the targeted cancer cells. Postulated and hypothetical mechanisms of action for the platinum complexes are discussed throughout the recent literature.

The compositions of the present invention comprise a therapeutically effective amount of a Formula (I) compound. As previously defined, the compounds of Formula (I) include pharmaceutically-acceptable salts of such compounds, as well as prodrugs, analogs, conjugates, hydrates, solvates and polymorphs, stereoisomers (including diastereoisomers and enantiomers) and tautomers of such compounds. Compounds of Formula (I), and their synthesis are described in, e.g., U.S. Pat. Nos. 5,808,160, 5,922,902, 6,160,167, and 6,504,049, the disclosures of which are hereby incorporated by reference in their entirety. In addition, Formula (I) compounds also include the metabolite of disodium 2,2'-dithio-bis-ethane sulfonate, known as 2-mercapto ethane sulfonate sodium (mesna) or 2-mercaptoethane sulfonate as a disulfide form which is conjugated with a variety of substituent groups, as described in Published U.S. Patent Application 2005/0256055, the disclosure of which is incorporated herein, by reference, in its entirety.

The putative mechanisms of the Formula (I) compositions of the present invention which function in the potentiation of the anti-cancer activity of chemotherapeutic agents may involve one or more of several novel pharmacological and physiological factors, including but not limited to, a prevention, compromise, and/or reduction in the normal increase, responsiveness, or in the concentration and/or tumor protective metabolism of glutathione/cysteine and other physiological cellular thiols; these antioxidants and enzymes are increased in concentration and/or activity, respectively, in response to the induction of intracellular oxidative metabolism which may be caused by exposure to cytotoxic chemotherapeutic agents in tumor cells. Additional information regarding certain mechanisms which may be involved in Formula (I) compounds is disclosed in U.S. patent application Ser. No. 11/724,933, filed Mar. 16, 2007, the disclosure of which is hereby incorporated by reference in its entirety.

Additionally, disclosure is provided herein which provides evidence that Formula (I) compounds of the present invention also play a role in: (i) increasing patient survival time in cancer patients receiving chemotherapy; (ii) maintaining or stimulating hematological function in patients in need thereof, including those patients suffering from cancer; (iii) maintaining or stimulating erythropoietin function or synthesis in patients in need thereof, including those patients suffering from cancer; (iv) mitigating or preventing anemia in patients in need thereof, including those patients suffering from cancer; (v) maintaining or stimulating pluripotent, multipotent, and unipotent normal stem cell function or synthesis in patients in need thereof, including those patients suffering from cancer; (vi) promoting the arrest or retardation of tumor progression in those cancer patients receiving chemotherapy; and (vii) increasing patient survival and/or delaying tumor progression while maintaining or improving the quality of life in a cancer patient receiving chemotherapy.

Preferred doses of the Formula (I) compounds of the present invention range from about 1 g/m$^2$ to about 50 g/m$^2$, preferably about 5 g/m$^2$ to about 40 g/m$^2$ (for example, about 10 g/m$^2$ to about 30 g/m$^2$), more preferably about 14 g/m$^2$ to about 22 g/m$^2$, with a most preferred dose of 18.4 g/m$^2$.

VIII. Pharmacology of Erythropoietin and the Process of Erythropoiesis

Erythropoiesis is the process by which red blood cells (erythrocytes) are produced. In the early fetus, erythropoiesis takes place in the mesodermal cells of the yolk sac. By the third or fourth month of fetal development, erythropoiesis moves to the spleen and liver. In human adults, erythropoiesis generally occurs within the bone marrow. The long bones of the arm (tibia) and leg (femur) cease to be important sites of hematopoiesis by approximately age 25; with the vertebrae, sternum, pelvis, and cranial bones continuing to produce red blood cells throughout life. However, it should be noted that in humans with certain diseases and in some animals, erythropoiesis also occurs outside the bone marrow, within the spleen or liver. This is termed extramedullary erythropoiesis.

In the process of red blood cell maturation, a cell undergoes a series of differentiations. The following stages of development all occur within the bone marrow: (i) pluripotent hematopoietic stem cell; (ii) multipotent stem cell; (iii) unipotent stem cell; (iv) pronormoblast; (v) basophilic normoblast/early normoblast; (vi) polychrmatophilic normoblast/intermediate normoblast; (vii) orthochromic normoblast/late normoblast; and (viii) reticulocyte. Following these stages, the cell is released from the bone marrow, and ultimately becomes an "erythrocyte" or mature red blood cell circulating in the peripheral blood. These stages correspond to specific histological appearances of the cell when stained with Wright's stain and examined via light microscopy, but they also correspond to numerous other intrinsic biochemical and physiological changes. For example, in the process of maturation, a basophilic pronormoblast is converted from a cell with a large nucleus and a volume of 900 μm$^3$ to an enucleated disc with a volume of 95 μm$^3$. By the reticulocyte stage, the cell has extruded its nucleus, but is still capable of producing hemoglobin.

A feedback loop involving the cytokine glycoprotein hormone erythropoietin (discussed below) helps regulate the process of erythropoiesis so that, in non-disease states, the production of red blood cells is equal to the destruction of red blood cells and the red blood cell number is sufficient to sustain adequate tissue oxygen levels but not so high as to cause blood thickening or "sludging", thrombosis, and/or stroke. Erythropoietin is produced in the kidney and liver in response to low oxygen levels. In addition, erythropoietin is bound by circulating red blood cells; low circulating numbers lead to a relatively high level of unbound erythropoietin, which stimulates production in the bone marrow.

Recent studies have also shown that the peptide hormone hepcidin may also play a role in the regulation of hemoglobin production, and thus effect erythropoiesis. Hepcidin, produced by the liver, controls iron absorption in the gastrointestinal tract and iron release from reticuloendothelial tissue. Iron must be released from macrophages in the bone marrow to be incorporated into the heme group of hemoglobin in erythrocytes.

There are colony forming units (e.g., including the granulocyte monocyte colony forming units) that cells follow during their formation. These cells are referred to as the committed cells. For example, the loss of function of the erythropoietin receptor or JAK2 in mice cells causes failure in erythropoiesis, so production of red blood cells in embryos and growth is disrupted. Similarly, the lack of feedback inhibition, such as SOCS (Suppressors of Cytokine Signaling) proteins in the system, have been shown to cause gigantism in mice.

Erythropoietin (EPO) is a cytokine glycoprotein hormone that is a cytokine for erythrocyte (red blood cell) precursors in the bone marrow which regulates the process of red blood cell production (erythropoiesis). Cytokines are a group of proteins and peptides that function as signaling compounds produced by cells to communicate with one another. They act via cell-surface cytokine receptors. The cytokine family consists mainly of smaller water-soluble proteins and glycoproteins (i.e., proteins with an added sugar chain(s)) with a mass of between 8 and 30 kDa. They act like hormones and neurotransmitters but whereas hormones are released from specific organs into the blood and neurotransmitters are produced by neurons, cytokines are released by many types of cells. Due to their central role in the immune system, cytokines are involved in a variety of immunological, inflammatory, and infectious diseases. When the immune system is fighting pathogens, cytokines signal immune cells such as T-cells and macrophages to travel to the site of infection. In addition, cytokines activate those cells, stimulating them to produce more cytokines. However, not all their functions are limited to the immune system, as they are also involved in several developmental processes during embryogenesis. Cytokines are produced by a wide variety of cell types (both hemopoietic and non-hemopoietic), and can have effects on both nearby cells or throughout the organism. Sometimes these effects are strongly dependent on the presence of other chemicals and cytokines Cytokines may be synthesized and administered exogenously. However, such molecules can, at a latter stage be detected, since they differ slightly from the endogenous ones in, e.g., features of post-translational modification.

EPO is produced mainly by peritubular fibroblasts of the renal cortex. Regulation is believed to rely on a feed-back mechanism measuring blood oxygenation. Constitutively synthesized transcription factors for EPO, known as hypoxia inducible factors (HIFs), are hydroxylized and proteosomally-digested in the presence of oxygen. See, e.g., Jelkmann, W. Erythropoietin after a century of research: younger than ever. *Eur. J. Haematol.* 78 (3):183-205 (2007). Hypoxia-inducible factors (HIFs) are transcription factors that respond to changes in available oxygen in the cellular environment, in specific, to decreases in oxygen, or hypoxia.

Most, if not all, oxygen-breathing species express the highly-conserved transcriptional complex HIF-1, which is a heterodimer composed of an α- and a β-subunit, the latter being a constitutively-expressed aryl hydrocarbon receptor nuclear translocator (ARNT).

HIF-1 belongs to the PER-ARNT-SIM (PAS) subfamily of the basic helix-loop-helix (bHLH) family of transcription factors. The α-subunit of HIF-1 is a target for propyl hydroxylation by HIF prolyl-hydroxylase, which makes HIF-1α a target for degradation by the E3 ubiquitin ligase complex, leading to quick degradation by the proteosome. This occurs only in normoxic conditions. In hypoxic conditions, HIF prolyl-hydroxylase is inhibited, since it utilizes oxygen as a co-substrate.

Hypoxia also results in a buildup of succinate, due to inhibition of the electron transport chain in the mitochondria. The buildup of succinate further inhibits HIF prolyl-hydroxylase action, since it is an end-product of HIF hydoxylation. In a similar manner, inhibition of electron transfer in the succinate dehydrogenase complex due to mutations in the SDHB or SDHD genes can cause a build-up of succinate that inhibits HIF prolyl-hydroxylase, stabilizing HIF-1 α. This is termed pseudohypoxia.

HIF-1, when stabilized by hypoxic conditions, upregulates several genes to promote survival in low-oxygen conditions. These include glycolysis enzymes, which allow ATP synthesis in an oxygen-independent manner, and vascular endothelial growth factor (VEGF), which promotes angiogenesis. HIF-1 acts by binding to HIF-responsive elements (HREs) in promoters that contain the sequence NCGTG. In general, HIFs are vital to development. In mammals, deletion of the HIF-1 genes results in perinatal death. HIF-1 has been shown to be vital to chondrocyte survival, allowing the cells to adapt to low-oxygen conditions within the growth plates of bones.

Erythropoietin is available as a therapeutic agent produced by recombinant DNA technology in mammalian cell culture. It is used in treating anemia resulting from chronic kidney disease, from the treatment of cancer (e.g., from chemotherapy and radiation) and from other critical illnesses (e.g., heart failure).

In should be noted that there have been a number of recent warnings released by both pharmaceutical manufacturers and the United States Food and Drug Administration (FDA) concerning the safety of EPO use in anemic cancer patients. Initially, a manufacturer of erythropoiesis-stimulating agents (ESAs), disseminated a "Dear Doctor" letter in 2007, that highlighted results from a recent clinical trial which examined cancer-associated anemia, and warned doctors to consider use in that off-label indication with caution. An ESA manufacturer also advised the FDA regarding the results of three (3) clinical trials: the DAHANCA 10; PREPARE, and GOG-191 clinical trials. For example, DAHANCA refers to a series of studies, entitled "Danish Head and Neck Cancer Studies" the most recent of which is "DAHANCA 10". See. e.g., Eriksen, J. and Overgaard, J., Lack of prognostic and predictive value of CA IX in radiotherapy of squamous cell carcinoma of the head and neck with known modifiable hypoxia: An evaluation of the DAHANCA 5 study. *Radiotherap. Oncol.* 83(3):383-388 (2007). In this study, the DAHANCA 10 data monitoring committee found that three year loco-regional control of various types of head and neck cancers in subjects treated with an ESA was significantly worse than for those not receiving an ESA (p=0.01). In response to these advisories, the FDA subsequently released a Public Health Advisory and a clinical alert for physicians, regarding the use of ESAs. The advisory recommended caution in using these agents in cancer patients receiving chemotherapy or off chemotherapy, and indicated a lack of clinical evidence to support improvements in quality of life or transfusion requirements in these settings. In addition, ESA manufacturers have agreed to new Black Box Warnings about the safety of these drugs. It should be noted that, additional information regarding various ESAs may be obtained from the Food and Drug Administration (FDA) or the specific ESA manufacturers themselves.

A related cytokine, colony-stimulating factors (CSF), are secreted glycoproteins which bind to receptor proteins on the surfaces of hematopoietic stem cells and thereby activate intracellular signaling pathways which can cause the cells to proliferate and differentiate into a specific kind of blood cell (typically white blood cells). Hematopoietic stem cells (HSC) are stem cells (i.e., cells retain the ability to renew themselves through mitotic cell division and can differentiate into a diverse range of specialized cell types) that give rise to all the blood cell types including myeloid (e.g., monocytes, macrophages, neutrophils, basophils, eosinophils, erythrocytes, megakaryocytes/platelets, dendritic cells, and the like) and lymphoid lineages (e.g., T-cells, B-cells, NK-cells, and the like). The definition of hematopoietic stem cells has undergone considerable revision in the last two decades. The hematopoietic tissue contains cells with long-term and short-term regeneration capacities and committed multipotent, oligopotent, and unipotent progenitors. Recently, long-term transplantation experiments point toward a clonal diversity model of hematopoietic stem cells. Here, the HSC compartment consists of a fixed number of different types of HSC, each with epigenetically-preprogrammed behavior. This contradicts older models of HSC behavior, which postulated a single type of HSC that can be continuously molded into different subtypes of HSCs. For example, HSCs constitute 1:10.000 of cells in myeloid tissue.

Colony-stimulating factors may be synthesized and administered exogenously. However, such molecules can at a latter stage be detected, since they differ slightly from endogenous ones in e.g., post-translational modification. The name "colony-stimulating factors" comes from the method by which they were discovered. Hemopoietic stem cells were cultured on a so-called semi solid matrix which prevents cells from moving around, so that if a single cell starts proliferating, all of the cells derived from it will remain clustered around the spot in the matrix where the first cell was originally located, and these are referred to as "colonies." It was therefore possible to add various substances to cultures of hemopoietic stem cells and then examine which kinds of colonies (if any) were "stimulated" by them. The substance which was found to stimulate formation of colonies of macrophages, for instance, was called macrophage colony-stimulating factor, and so on. The colony-stimulating factors are soluble, in contrast to other, membrane-bound substances of the hematopoietic microenvironment. This is sometimes used as the definition of CSF. They transduce by paracrine, endocrine, or autocrine signaling.

Colony-stimulating factors include: macrophage colony-stimulating factor; granulocyte-macrophage colony-stimulating factor; and granulocyte colony-stimulating factor. Macrophage colony-stimulating factor (M-CSF or CSF-1), is a secreted cytokine which influences hematopoietic stem cells to differentiate into macrophages or other related cell types. M-CSF binds to the macrophage colony-stimulating factor receptor. It may also be involved in development of the placenta.

Granulocyte-macrophage colony-stimulating factor (GM-CSF or CSF-2), is a protein secreted by macrophages, T-cells, mast cells, endothelial cells, and fibroblasts. GM-CSF is a cytokine that functions as a white blood cell growth factor. GM-CSF stimulates stem cells to produce granulocytes (e.g., neutrophils, eosinophils, and basophils) and monocytes. Monocytes exit the circulation and migrate into tissue, whereupon they mature into macrophages. It is thus part of the immune/inflammatory cascade, by which activation of a small number of macrophages can rapidly lead to an increase in their numbers, a process crucial for fighting infection. The active form of the protein is found extracellularly as a homodimer.

Granulocyte Colony-Stimulating Factor (G-CSF or CSF-3), is a colony-stimulating factor hormone. It is a glycoprotein, growth factor, or cytokine produced by a number of different tissues to stimulate the bone marrow to produce granulocytes and stem cells. G-CSF then stimulates the bone marrow to pulse them out of the marrow into the blood. It also stimulates the survival, proliferation, differentiation, and function of neutrophil precursors and mature neutrophils. G-CSF is produced by endothelium, macrophages, and a number of other immune cells. The natural human glycoprotein exists in two forms, a 174- and 180-amino acids-long protein of molecular weight 19,600 grams per mole. The more-abundant and more-active 174-amino acid form has been used in the development of pharmaceutical products by recombinant DNA (rDNA) technology. The G-CSF receptor is present on precursor cells in the bone marrow, and, in response to stimulation by G-CSF, initiates proliferation and differentiation into mature granulocytes. Promegapoietin is a recombinant drug which is given during chemotherapy to increase blood cell regeneration. It is a colony-stimulating factor that stimulates megakaryocyte production. It functions by stimulating ligands for interleukin-3 and c-Mpl.

IX. Mechanisms of Action of Tavocept™

An important element of Tavocept's™ effectiveness as a compound in the treatment of cancer is its selectivity for normal cells versus cancer cells and its inability to interfere with the anti-cancer activity of chemotherapeutic agents. In vitro studies demonstrated that Tavocept™ does not interfere with paclitaxel induced apoptosis, as assessed by PARP cleavage, Bcl-2 phosphorylation, and DNA laddering in human breast, ovarian and lymphoma cancer cell lines. Additionally, Tavocept™ did not interfere with paclitaxel and platinum induced cytotoxicity in human cancer cell lines and did not interfere with paclitaxel and platinum regimens in the animals models discussed herein.

The potential mechanisms underlying the absence of interference with anti-cancer activity by Tavocept™ are multifactorial and, as previously discussed, may involve its selectivity for normal cells versus cancer cells, inherent chemical properties that have minimal impact in normal cells on critical plasma and cellular thiol-disulfide balances, and its interactions with cellular oxidoreductases, which are key in the cellular oxidative/reduction (redox) maintenance systems.

In addition to the absence of interference with anti-cancer activity, results from in vivo studies have shown that Tavocept™ may elicit the restoration of apoptotic sensitivity in tumor cells through thioredoxin- and glutaredoxin-mediated mechanisms and this may be an important element of its effectiveness as a chemotherapeutic agent. It has been determined that Tavocept™ is a substrate for thioredoxin and exhibits substrate-like activity with glutaredoxin in the presence of reduced glutathione and glutathione reductase, and this substrate-like activity may be due to non-enzymatic formation of glutathione-containing disulfide heteroconjugates during the assay reaction; these glutathione disulfide heteroconjugates may, in turn, act as substrates for glutaredoxin. Thus, Tavocept™ could potentially shift the intracellular balance of oxidized (inactive) and reduced (active) thioredoxin or glutaredoxin, subsequently modulating their cellular activity.

Similarly, increased concentrations of Tavocept™ cause a marked increase in the percent of inhibition of GST catalysis in the conjugation of reduced glutathione to 1-chloro-2, 4-dinitrobenzene (CDNB) (this data will be presented, infra). One function of GST and related species (GSTs) is to protect mammalian cells against the neoplastic effects of electrophilic metabolites of carcinogens and reactive oxygen species by, e.g., catalyzing the conjugation of glutathione to a variety of electrophilic compounds. Moreover, GSTs are highly expressed in tumor tissue relative to normal tissue, are found in high levels in the plasma of cancer patients, and increased expression of GSTs has been linked to the development of cellular resistance to alkylating cytostatic drugs.

Tavocept™ restoration of the apoptotic sensitivity of tumor cells via thioredoxin, glutaredoxin or related cellular redox systems, would have a net anti-proliferative activity on tumor cells. Thioredoxin and GST are key players both in apoptotic pathways in cells and in the intracellular redox environment and any molecule that inhibits or serves as substrate for these proteins could offset changes in the intracellular redox environments that are due to high/elevated/aberrant levels of thioredoxin and/or GST. The effect of Tavocept™ on thioredoxin and/or GST could also potentially normalize redox sensitive signaling pathways that are involved in apoptosis. Thus, the net results would be an increased sensitivity of tumor cells to chemotherapeutic agents and/or restoration of a more normal intracellular redox environment A substantial increase in the inactive forms of these oxidoreductases could result in significant changes in redox homeostasis, cell proliferation, and gene transcription through reductive control over various transcription factors. Specifically, the involvement of the thioredoxin system in tumor progression, its influence on p53-mediated gene transcription, and its demonstrated roles in neuroprotection against chemical toxins would indicate that interaction of this system with Tavocept™ could have a variety of positive clinical sequelae including: (i) inhibition of tumor growth in the presence of oxidative stressors; (ii) protection of normal cells during chemically-induced hyperoxidation and hyperthermia of cancer cells; and/or (iii) amelioration of chemically-induced neurotoxicity.

X. Activity of Tavocept™ on Physiological Cellular Thiols and Non-Protein Sulfhydryls (NPSH)

As the number of agents and treatments for cancer, as well as the number of subjects receiving one or more of these chemotherapeutic agents concomitantly, has increased, clinicians and researchers are seeking to fully elucidate the biological, chemical pharmacological, and cellular mechanisms which are responsible for the pathogenesis and pathophysiology of the various adverse disease manifestations, as well as how these chemotherapeutic drugs exert their anti-cancer and cytotoxic or cytostatic activity on a biochemical and pharmacological basis. As described herein, with the exception of the novel conception and practice of the present invention, there is no pharmaceutical composition(s) presently available which is: (i) is capable of affecting the intracellular concentration of thioredoxin and glutaredoxin and/or mitigating or preventing thioredoxin- or glutaredoxin-mediated resistance to chemotherapeutic agents results in an increase in cancer patient survival time, in comparison to those cancer patients who did not receive the pharmaceutical composition; and (ii) preventing or delaying the initial onset of, attenuating the overall severity of, and/or expediting the resolution of the acute or chronic deleterious chemotherapeutic agent-induced effects.

The mechanisms by which the Formula (I) compounds of the present invention (which include 2,2'-dithio-bis-ethane sulfonate and pharmaceutically-acceptable salts and analogs thereof) function involves several novel pharmacological and physiological factors, including but not limited to:

(i) a prevention, compromise and/or reduction in the normal increase, responsiveness, or in the concentration and metabolism of physiological cellular thiols; these antioxidants and enzymes are increased in concentration and/or activity, respectively, in response to the induction of changes in intracellular oxidative metabolism which may be caused by exposure to chemotherapeutic agents in tumor cells. The Formula (I) compounds of the present invention exert an oxidative activity by the intrinsic composition of the molecule itself (i.e., an oxidized disulfide), as well as by oxidizing free thiols to form oxidized disulfides (i.e., by non-enzymatic SN2-mediated reactions, wherein attack of a thiol/thiolate upon a disulfide leads to the departure of the more acidic thiol group. As the thiolate group is far more nucleophilic than the corresponding thiol, the attack is believed to be via the thiolate), and by the pharmacological depletion and metabolism of reductive physiological free thiols (e.g., glutathione, cysteine, and homocysteine). These pharmacological activities will thus have an additive effect on cytotoxic chemotherapy administration to patients with cancer, and additional anti-cancer activity will result from the administration of an oxidative metabolism-affecting Formula (I) compound of the present invention, increasing drug efficacy, and reducing the tumor-mediated resistance of the various co-administered chemotherapeutic agents, e.g., platinum, taxane, and alkylating agent-based drug efficacy and tumor-mediated drug resistance;

(ii) thioredoxin inactivation by an oxidative metabolism-affecting Formula (I) compound of the present invention, thereby increasing apoptotic sensitivity and decreasing mitogenic/cellular replication signaling in cancer cells;

(iii) a key metabolite of the Formula (I) compound, Tavocept™ (disodium 2,2'-dithio-bis-ethane sulfonate), which is known as 2-mercapto ethane sulfonate sodium (also known in the literature as mesna) possesses intrinsic cytotoxic or cytostatic activity (i.e., causes apoptosis) in some tumors which can kill cancer cells directly; and (iv) it is believed that the Formula (I) compounds of the present invention may act by causing changes in intracellular oxidative metabolism of cancer tumor cells, and may enhance their oxidative biological and physiological state and thereby increase the amount of oxidative damage (e.g., mediated by ROS, RNS or other mechanisms) in tumor cells exposed to chemotherapy, thereby enhancing cytotoxicity/apoptosis of chemotherapy agents. Thus, by altering intracellular oxidative metabolism by enhancing levels of physiologically-deleterious oxidative compounds and/or reducing or compromising the total anti-oxidative capacity or responsiveness of cancer tumor cells, a marked increase in anti-cancer activity can be achieved. It is believed by the Applicant of the present invention that this is a key mechanism of action (that may act in concert with various other mechanisms of anti-cancer augmentation) of the Formula (I) compounds of the present invention, with very important implications for treatment.

Compositions and formulations comprising the Formula (I) compounds of the present invention may be given using any combination of the following three general treatment methods: (i) in a direct inhibitory or inactivating manner (i.e., direct chemical interactions that inactivate thioredoxin and/or glutaredoxin) and/or depletive manner (i.e., decreasing thioredoxin and/or glutaredoxin concentrations or production rates), thereby increasing the susceptibility of the cancer cells to any subsequent administration of any chemotherapeutic agent or agents that may act directly or indirectly through the thioredoxin- and/or glutaredoxin-mediated pathways in order to sensitize the patient's cancer and thus increase the survival of the patient; and/or (ii) in a synergistic manner, where the anti-thioredoxin and/or glutaredoxin therapy is concurrently administered with chemotherapy administration when a cancer patient begins any chemotherapy cycle, in order to increase and optimize the pharmacological activity directed against thioredoxin- and/or glutaredoxin-mediated mechanisms present while chemotherapy is being concurrently administered; and/or (iii) in a post-treatment manner (i.e., after the completion of chemotherapy dose administration or a chemotherapy cycle) in order to maintain the presence of a pharmacologically-induced depletion, inactivation, or modulation of thioredoxin and/or glutaredoxin in the patient's cancer cells for as long as optimally required. Additionally, the aforementioned compositions and formulations may be given in an identical manner to increase patient survival time in a patient receiving treatment with a cytotoxic or cytostatic anti-cancer agent by any additionally clinically-beneficial mechanism(s).

XI. Summary of Tavocept™-Related Studies Focusing on Potential Effects on the Thioredoxin and Glutaredoxin Systems (i) Various Formula (I) compounds, including Tavocept™ (BNP7787, dimesna) and Tavocept™-derived mesna disulfide heteroconjugates function as alternative substrate inhibitors of the thioredoxin and/or glutaredoxin systems (see, Tables 3 and 4; infra).

(ii) Various Formula (I) compounds, including Tavocept™ and Tavocept™-derived mesna disulfide heteroconjugates have been shown to promote formation of oxidized thioredoxin or oxidized glutaredoxin, and since anti-apoptotic and cell growth signals usually require reduced thioredoxin and reduced glutaredoxin, this Tavocept™-mediated shift towards oxidized thioredoxin and/or glutaredoxin may result in increased apoptotic sensitivity and inhibition of cell growth pathways.

(iii) Tavocept™ is a substrate ($K_m$=72 µM) for the coupled thioredoxin/thioredoxin reductase system (but not thioredoxin reductase alone).

(iv) Tavocept™ inhibits ($K_m$=3.6 mM) thioredoxin/thioredoxin reductase catalyzed reduction of the insulin A-B chain disulfide.

(v) Tavocept™ may depleted intracellular glutathione resulting in formation of a Tavocept™-derived mesna disulfide heteroconjugates (e.g., BNP7772). Tavocept™ is believed to interfere with glutathione-mediated reduction of oxidized glutaredoxin by serving as an alternative substrate inhibitor of reduced glutaredoxin and/or by depleting intracellular glutathione available to reduce oxidized glutaredoxin to the active reduced form.

A better understanding of the present invention will be gained by reference to the following section disclosing Specific Examples and Experimental/Clinical Results. The following examples are illustrative and are not intended to limit the invention or the claims in any manner.

Specific Examples and Experimental/Clinical Results

I. Effects of Tavocept™ on Glutathione-S-Transferase (GST)

One potential hypothesis set forth to explain the ability of Tavocept™ (disodium 2,2'-dithio-bis-ethane sulfonate; BNP7787) to augment the anti-cancer activity of chemotherapeutic agents states that Tavocept™ may act as a glutathione surrogate or modulator in the reactions of glutathione-S-transferase (GST). Glutathione and its related enzymes play a major role in the detoxification of toxic chemicals including cytotoxic chemotherapeutics. Glutathione-S-transferases (GSTs) constitute a family of phase II detoxifying isozymes that catalyze the conjugation of glutathione to a variety of electrophilic compounds, often the first step in the formation of mercapturic acid derivatives such as N-acetylcysteine. Reaction Scheme I, below, illustrates Glutathione S-transferase catalyzing the transfer of glutathione to an electrophilic species RX (wherein, R is S, N or C).

Reaction Scheme I

The resulting glutathione conjugates are either excreted from the cell or they undergo further enzymatic processing by γ-glutamyl transpeptidase and cysteine-S-conjugate-β-lyase. See, e.g., Hausheer, F. H., et al., Modulation of platinum-induced toxicities and therapeutic index: mechanistic insights and first- and second-generation protecting agents. *Semin. Oncol.* 25:584-599 (1998). Glutathione-S-transferases (GSTs) are highly expressed in tumor tissue relative to normal tissues and are also found in high levels in the plasma of cancer patients; thereby making these enzymes useful as potential cancer markers. There are multiple cytosolic- and membrane-bound GST isozymes that differ in their tissue-specific expression and distribution. GSTs protect mammalian cells against the toxic and neoplastic effects of electrophilic metabolites of carcinogens and reactive oxygen species. For example, increased expression of GSTs has been linked to the development of cellular resistance to alkylating cytostatic drugs. A deficiency of GST isozymes may increase the predisposition to various forms of cancer. Therefore, GST status may be a useful diagnostic factor in determining the clinical outcome of chemotherapy.

The following experiments were designed to determine if Tavocept™ has an inhibitory or stimulatory effect on GST. Specifically, these studies address whether Tavocept™ can act as a substrate for GST or if either of these compounds inhibit GST. An in vitro assay for GST has been developed and reported. See, Meyer, D. J. and Ketterer, B., Purification of soluble human glutathione S-transferases. *Methods Enzymol.* 252:53-65 (1995). This assay monitors the conjugation of reduced glutathione to 1-chloro-2, 4-dinitrobenzene (CDNB), as illustrated in Reaction Scheme II, below.

Reaction Scheme II

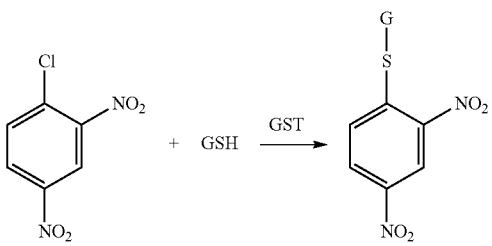

Reduced thiol forms a conjugate with CDNB (extinction coefficient=9600 $M^{-1}$ $cm^{-1}$), which is detected at 340 nm. Stock solutions of GSH, CDNB, Tavocept™ were prepared by dissolving the reagent in sterile water at the concentrations listed below prior to use. A typical 1 mL assay was set up by mixing 500 μL $NaHPO_4$ buffer (200 mM, pH 6.5), 20 μL GSH (50 mM), 20 μL CDNB (50 mM), and 458 μL sterile water. Reactions were incubated at 20° C. in the cuvette holder of the spectrophotometer for approximately 5 min. prior to initiating the assay with the addition of enzyme (m1-1 isotype of GST; activity >100 U/mg). The enzyme stock purchased from the vendor was diluted 1:100 in 200 mM $NaHPO_4$ buffer (pH 6.5), and 2 μL of the diluted enzyme was added to initiate the reaction. The final amount of enzyme added to the assay was typically 0.002 U. Assays were run at 20° C. in 1 mL quartz cuvettes (Hellma Scientific). Slopes were measured in the linear range of the assay (i.e., typically between 5 to 10 min.). In assays where the effect of Tavocept™ on GST activity was measured, 20 μL of either a 500 mM, 166.7 mM, or 55.6 mM stock solution of Tavocept™ was added to standard reactions using 1 mM GSH as the enzyme substrate. Final reaction volumes were fixed at 1 mL by adjusting the amount of water added.

All UV-visible assays were performed using a Varian Cary 100 spectrophotometer equipped with a thermostatic jacketed multi-cell holder. The default parameters of the Cary Win UV Enzyme Kinetics application (version 2.00) were used; with the exceptions of using both the visible and deuterium lamps, and setting the wavelength to 340 nm, the temperature to 20° C., and the maximal duration of the assay at 30 minutes.

Figure 16:
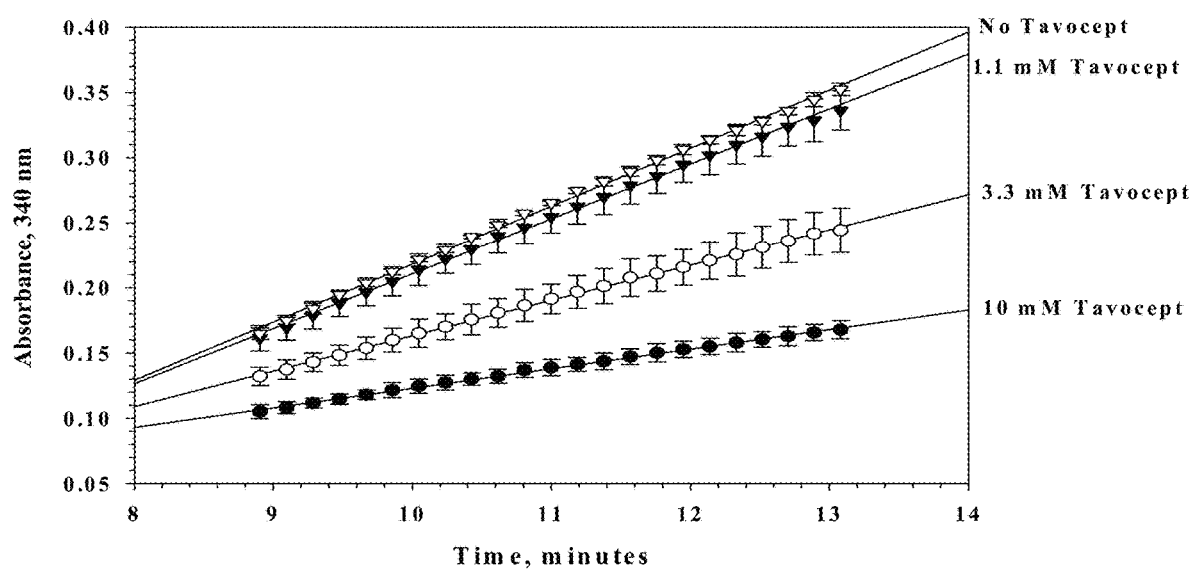
FIG. 16 illustrates, in graphical form, whether Tavocept™ can act as a substrate for GST or if Tavocept™ has an inhibitory or stimulatory effect on GST. The assay monitors the conjugation of reduced glutathione to 1-chloro-2, 4-dinitrobenzene (CDNB).

Raw data was obtained on a Cary 100 spectrophotometer. This data showed several phases to a typical reaction. The first phase was a baseline corresponding to the time prior to addition of enzyme (typically 2-5 min. in duration). Assays in the first phase of the reaction contained only substrate, buffer and (in some assays) Tavocept™. The spectrophotometer was put in pause mode while enzyme (GST) was added and mixed into the assay reactions. No absorbance values were collected during the process of enzyme addition. The region of experimental interest was during the linear phase of the enzyme reaction, which immediately followed the addition of enzyme. The linear phase is of experimental interest because it is when the classical model of Michaelis-Menton kinetics holds true. During this phase the substrate concentration is high (>Km for enzyme) and, therefore, the rate of catalysis is independent of the substrate concentration. It was during this time that reaction rates (i.e., slopes of change in absorbance with time) were measured using the Cary 100 software. The duration of the linear phase was between 5-10 minutes, depending upon the specific reaction conditions. Reactions were considered complete when substrate concentration was no longer saturating and became a rate limiting factor of the assay. When the substrate was limiting, the reaction rate deviated from linearity. This end phase of the reaction was typically observed after 10 to 15 minutes. Absorbance and time values during the end phase of the reaction were not used in slope calculations because the reaction was effectively over at this point as the reaction no longer followed the classical Michaelis-Menton model for enzyme kinetics. Completion of the reaction on the Cary software could be detected visually by overlaying a straight line beginning at the addition of enzyme and extending past the end phase of the assay curve. Upon completion of a set of reactions data was stored as an electronic "batch" file. Sigma Plot was used specifically to show the mean of assays run in triplicate with linear regression lines and error bars illustrating standard deviation. Descriptive statistics (mean and standard deviation) were used to describe and summarize the results of the experiments. The results of these experiments are illustrated in FIG. 16.

The GST reaction was performed in the presence of Tavocept™. Final Tavocept™ concentrations are shown to the right of each regression curve. Data points shown represents the average curve of triplicate experiments for each assay condition, and error bars are standard deviation. Assays were measured after the addition of GST in the linear range (i.e., 8.9 min. to 13.1 min.).

Figure 17:
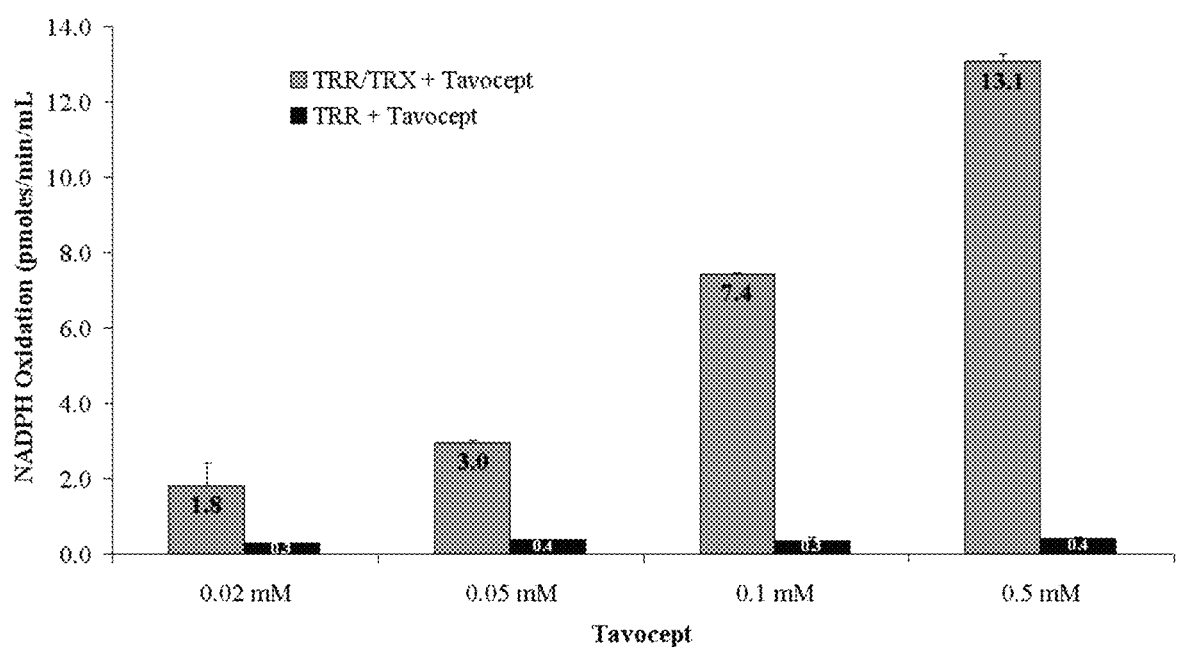
FIG. 17 illustrates, in graphical form, the individual slopes for each of the three assay runs for a given Tavocept™ concentration, the standard deviation, the mean, the relative enzyme activity, and percent inhibition. The slopes for each assay trial were calculated from the change in absorbance at 340 nm per minute in the linear portion of the assay and measured from 8.9 to 13.1 min. The relative activity was normalized using the slope mean to the reactions having no Tavocept™ added; and percent inhibition was calculated as the difference of relative activity from 100%.

The individual slopes for each of the three assay runs for a given Tavocept™ concentration, the standard deviation, the mean, the relative enzyme activity, and percent inhibition are listed in FIG. 17.

FIG. 17 shows the slopes for each assay trial, which were calculated from the change in absorbance at 340 nm per minute in the linear portion of the assay. In these examples, the slope was measured from 8.9 to 13.1 min. The relative activity was normalized using the slope mean to the reactions having no Tavocept™ added; and percent inhibition was calculated as the difference of relative activity from 100%.

Accordingly, the data obtained from both FIG. 16 and FIG. 17 illustrate that increased concentrations of Tavocept™ cause a marked increase in the percent of inhibition of GST catalysis in the conjugation of reduced glutathione to 1-chloro-2, 4-dinitrobenzene (CDNB), as initially illustrated in Reaction Scheme II, above. For example, an increase of Tavocept™ from 1.1 mM to 3.3 mM was shown to cause an increase in the percent inhibition from 5.6% to 39.0%. Thus, this relatively small increase in Tavocept™ concentration caused an approximate 6-times increase in GST inhibition.

One function of GST and related species (GSTs) is to protect mammalian cells against the neoplastic effects of electrophilic metabolites of carcinogens and reactive oxygen species by, e.g., catalyzing the conjugation of glutathione to a variety of electrophilic compounds. Moreover, GSTs are highly expressed in tumor tissue relative to normal tissues, are found in high levels in the plasma of cancer patients, and increased expression of GSTs has been linked to the development of cellular resistance to alkylating cytostatic drugs. Thus, it is probable that one possible mechanism of action of Tavocept™ may be to cause a change or changes in the intracellular oxidative metabolism (i.e., the oxidative/reductive potential) within tumor cells so as to increase the intracellular levels of physiologically-deleterious oxidative compounds. This change may, in turn, cause the tumor cell to exhibit greater sensitivity to a chemotherapeutic agent without directly affecting the mechanism of action of the chemotherapeutic agent itself.

II. Effects of Formula (I) Compounds on the Coupled GRX/GSH/GR System

Figure 2:
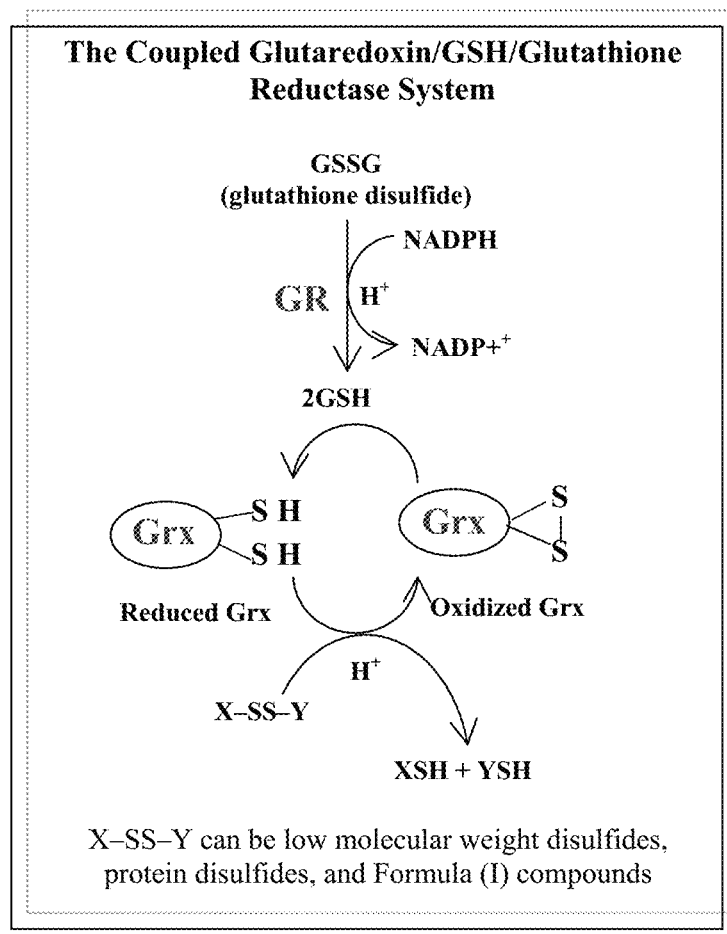
FIG. 2 illustrates the coupled glutaredoxin (Gxr)/glutathione (GSH)/glutathione reductase (GR) system.

FIG. 1 illustrates the involvement of (reduced) glutaredoxin in promoting cell growth and/or stimulating cell proliferation via several metabolic pathways. The glutaredoxin system consists of glutaredoxin, glutathione and glutathione reductase. It should be noted, however, that glutaredoxin is also involved in many other intracellular pathways. FIG. 2 illustrates the coupled glutaredoxin (GRX)/glutathione (GSH)/glutathione reductase (GR) system.

Table 4, below, illustrates that various Formula (I) compounds (i.e., dithiol-containing compounds) may act as alternative substrate inhibitors for the coupled GRX/GSH/GR system as measured by NADPH oxidation. The Formula (I) compound was utilized at a concentration of 0.5 mM.

TABLE 4

| | NADPH Oxidation (nmoles/min/mL)[1,2] | |
|---|---|---|
| Disulfide (0.5 mM) | [3]Thioredoxin Reductase only | Thioredoxin Reductase + Thioredoxin |
| BNP7787 | 0.3 ± 0.01 | 13.1 ± 0.2 |
| BNP7772 (GSSM) | 0.3 ± 0.02 | 14.1 ± 0.1 |
| BNP7766 (CSSM) | 0.2 ± 0.03 | 14.4 ± 0.2 |
| BNP7768 (HSSM) | 0.0 ± 0.03 | 8.6 ± 0.06 |
| BNP7774 (ECSSM) | 0.3 ± 0.02 | 9.6 ± 0.2 |
| BNP7776 (GlyCSSM) | 0.2 ± .04 | 15.8 ± 0.3 |

[1]Oxidation rates calculated from a minimum of triplicate assays.
[2]A two-way ANOVA analysis was performed on the whole dataset. The difference rates for type A reactions and type B reactions was statistically significant (p = .0001), and was affected by the disulfide used (p = .0001).
[3]Rates calculated from positive absorbance changes or absorbance changes of less than .0001 are shown as 0.0.

III. Effects of Formula (I) Compounds on the Coupled TX/TXR System

The TX system plays an important role in the redox regulation of a number of cellular processes, notably modulation of apoptosis and cellular proliferation. The system includes the selenoprotein, thioredoxin reductase (TXR), and its main substrate, thioredoxin (TX), as well as thioredoxin peroxidase (TPX). See, e.g., Zhong, L., et al., Rat and calf thioredoxin reductase are homologous to glutathione reductase with a carboxyl-terminal elongation containing a conserved catalytically active penultimate seloncysteine residue. *J. Biol. Chem.* 273: 8581-8591, 1998 Holmgren, A. Thioredoxin and glutaredoxin systems. *J. Biol. Chem.* 264: 13963-13966 (1989). TXR is a pyridine nucleotide-disulfide oxidoreductase, and catalyzes the NADPH-dependent reduction of the active site disulfide in oxidized thioredoxin (see, Reaction Scheme III; TRX-$S_2$) to give a dithiol in reduced thioredoxin (TX-(SH)$_2$). See, e.g., Zhong, L., et al. Rat and calf thioredoxin reductase are homologous to glutathione reductase with a carboxyl-terminal elongation containing a conserved catalytically active penultimate seloncysteine residue. *J. Biol. Chem.* 273:8581-8591 (1998). Reaction Scheme III, below, outlines the various reaction mechanisms involved in the TX redox regulation system.

Reaction Scheme III

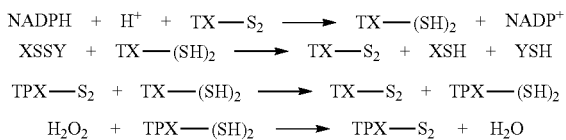

TX is a small disulfide reductase with a broad range of substrates and important functions in the redox modulation of protein signaling and the reductive activation of a number of important transcription factors. See, e.g., Welsh, S. J., et al., The thioredoxin redox inhibitors 1-methylpropyl 2-imidazolyl disulfide and pleurotin inhibit hypoxia-induced factor 1 alpha and vascular endothelial growth factor formation. *Mol. Cancer Therapy* 2:235-243 (2003). Like glutaredoxin (GRX), TX is only active in its reduced form (TX-(SH)$_2$) which serves as a hydrogen donor for ribonucleotide reductase and other redox enzymes, and acts in defense against changes in intracellular oxidative metabolism. While they share some substrate specificity, the TX system is more catalytically diverse than the GRX system and does not interact substantially with glutathione (GSH). See, e.g., Luthman, M., and Holmgren, A. Rat liver thioredoxin and thioredoxin reductase: purification and characterization. *Biochemistry* 21:6628-6633 (1982).

Figure 3:
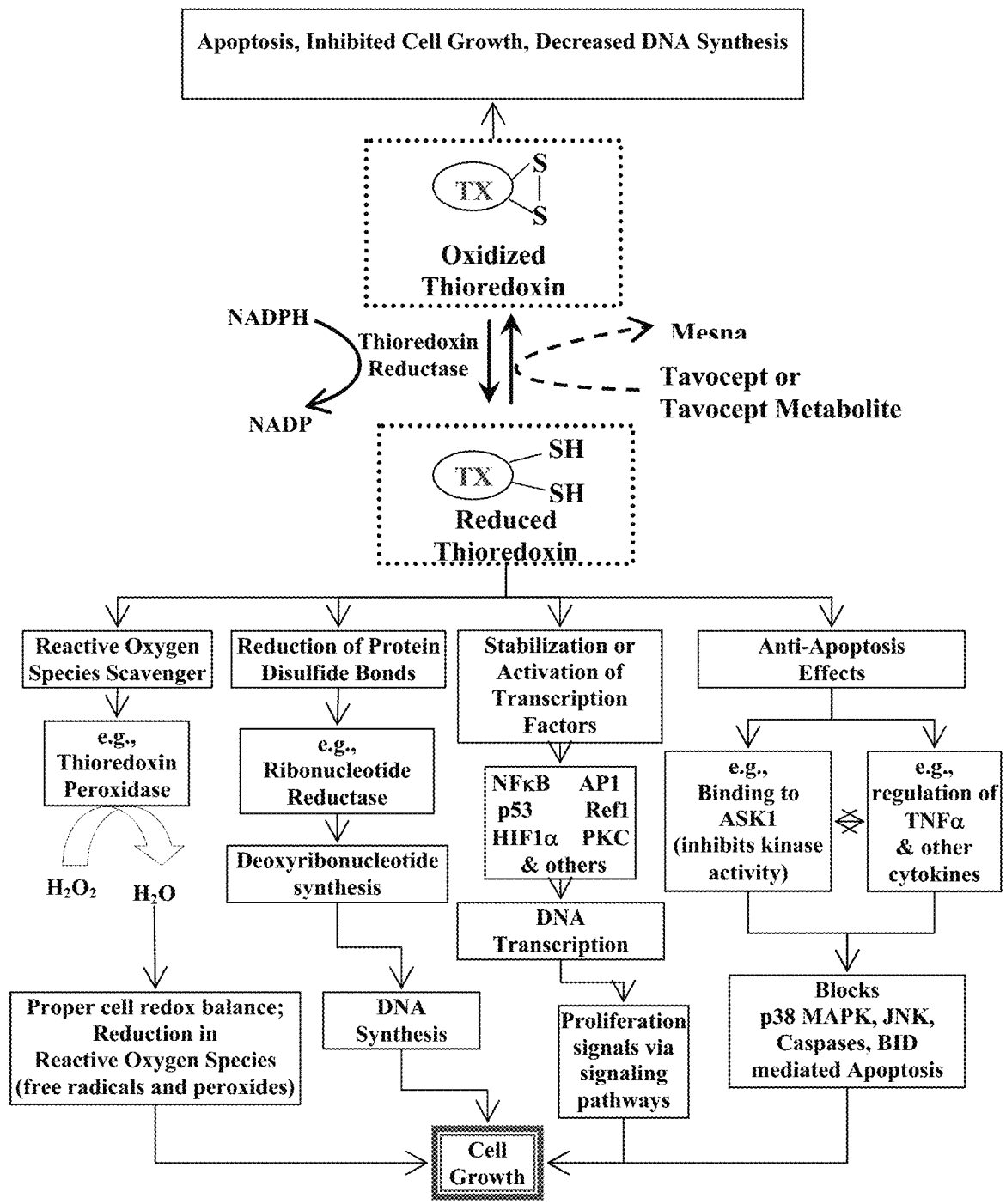
FIG. 3 illustrates several representative thioredoxin-related pathways involved in cell proliferation and apoptosis. For thioredoxin (TX) to promote cell growth, inhibit apoptosis or stimulate cell proliferation, it must be in the reduced form. It should be noted, however, that TX is also involved in many other intracellular pathways.
Figure 4:
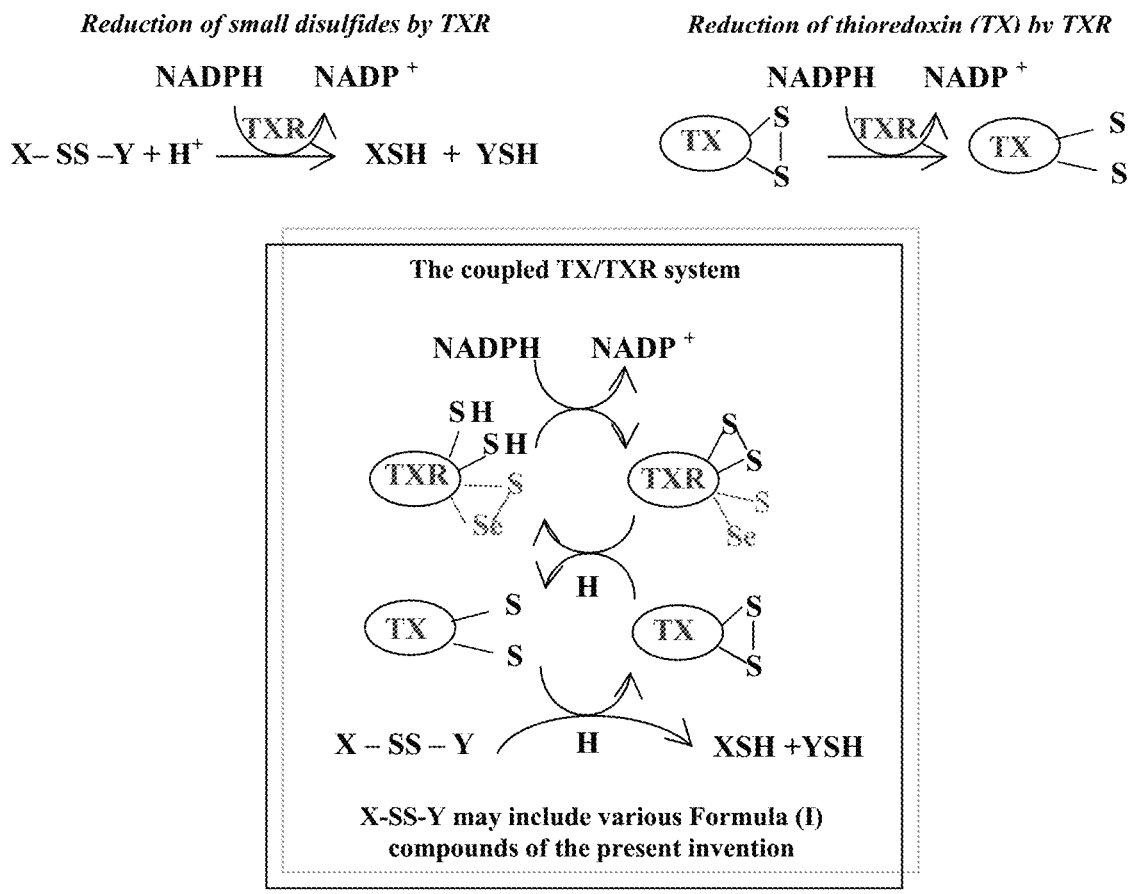
FIG. 4 illustrates the coupled thioredoxin (TX)/thioredoxin reductase (TXR) system.

FIG. 3 illustrates several representative thioredoxin-related pathways involved in cell proliferation and apoptosis. For thioredoxin (TX) to promote cell growth, inhibit apoptosis or stimulate cell proliferation, it must be in the reduced form. It should be noted, however, that TX is also involved in many other intracellular pathways. FIG. 4 illustrates the coupled thioredoxin (TX)/thioredoxin reductase (TXR) system.

The objective of the following experimental study was to determine if Tavocept™ has a detectable, direct interaction with the following oxidoreductase enzymes: glutathione reductase (GR); glutaredoxin (GRX); glutathione peroxidase (GPX); thioredoxin reductase (TXR); and thioredoxin (TX). Based upon the nature and magnitude of the interaction, it may be determined whether an interaction with redox balance enzymes could serve to explain clinical findings regarding Tavocept™ metabolism or its mechanism of action.

The activity of TXR and TX was determined by following NADPH oxidation at 340 nm according to the previously reported method. See, Luthman, M., and Holmgren, A. Rat liver thioredoxin and thioredoxin reductase: purification and characterization. *Biochemistry* 21:6628-6633 (1982). A typical assay mixture contained TR buffer (50 mM potassium phosphate, pH 7.0, 1 mM EDTA), 200 μM NADPH, 1.6 μg bovine TX, and one or more of the following: 4.8 μM TXR, 86 μM insulin, and one of the disulfides described herein. All disulfides were added to reactions as 10× solutions in TR buffer. The total volume of each reaction was 0.1 mL. Reactions were initiated by the addition of TX and were incubated at 25° C. for 40 min. The activity was calculated using a 4 min. linear portion of each reaction. Enzyme assays were carried out using either a Molecular Devices SpectraMaxPlus UV plate reader or a Varian Cary 100 UV-visible Spectrophotometer.

Data was then collected and plotted in Microsoft Excel. Error calculations, and graphical representations were performed in Microsoft Excel and Kaleidograph (ver. 3.5). Nonlinear data was graphically rendered using Kaleidograph. ANOVA and other statistical analyses were performed using SAS (ver. 8.2). Unless otherwise noted, significance level was set at 0.05, and error bars represent actual experimental standard deviation.

Figure 18:
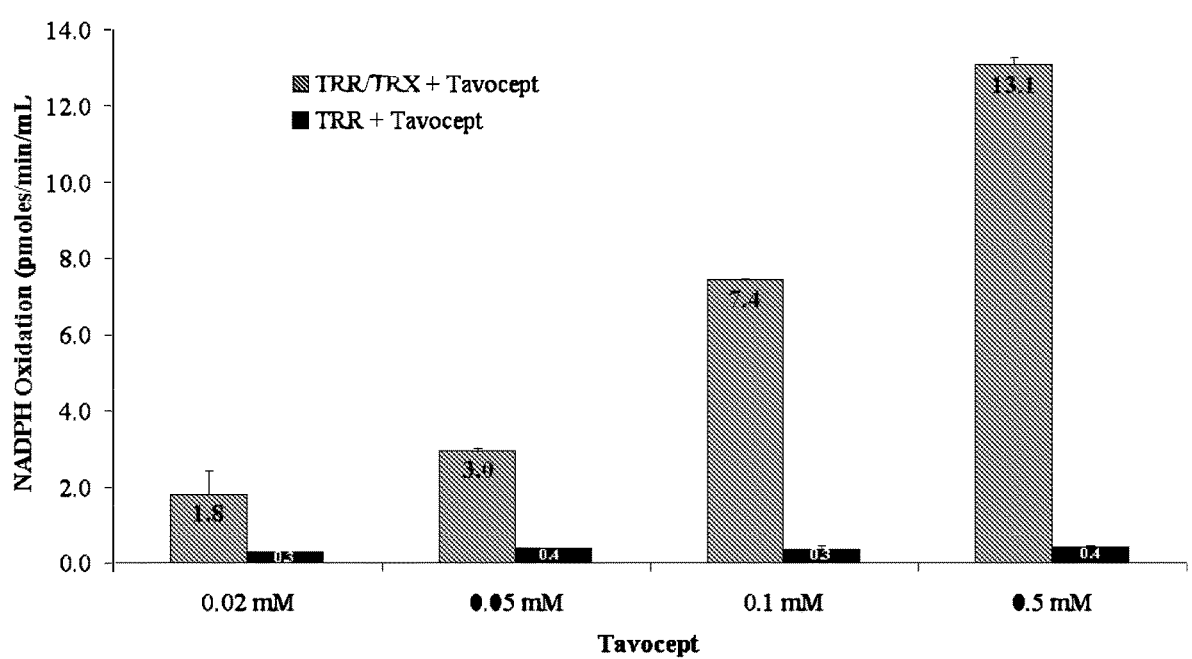
FIG. 18 is Table 5 which shows the activity of TXR and TX with Tavocept™.

The activity of TXR and TX with Tavocept™ is depicted in Table 5 shown in FIG. 18. Tavocept™ causes a concentration-dependent increase in NADPH oxidation by TXR in the presence of TX. In the absence of TX, the NADPH oxidation by TXR is indistinguishable from background. Based upon the magnitude and concentration-dependence of the observed oxidation responses, Tavocept™ is most likely a substrate for TX, but not for TXR. It should be noted that for the purposes of Table 5 only, thioredoxin is labeled TXR and thioredoxin reductase is labeled TRR.

Table 6, below, illustrates that various Formula (I) compounds (i.e., disulfide-containing compounds) of the present invention can serve as alternate substrate inhibitors for the coupled thioredoxin (TX)/thioredoxin reductase (TXR)/NADPH system as measured by the oxidation of NADPH. In Table 6, the Formula (I) compounds were utilized at a concentration of 0.5 mM.

TABLE 6

| Disulfide (0.5 mM) | NADPH Oxidation (nmoles/min/mL)[1,2] | | |
| --- | --- | --- | --- |
| | GR | GR + GSH | GR + GRX + GSH |
| BNP7787 (MSSM) | 0.0 ± 0.01 | 2.9 ± 1.6 | 15.3 ± 1.0 |
| BNP7772 (GSSM) | 8.0 ± 0.6 | 11.3 ± 0.8 | 71.0 ± 7.9 |
| BNP7766 (CSSM) | 0.0 ± 0.01 | 4.1 ± 1.3 | 28.3 ± 2.0 |
| BNP7768 (HSSM) | 0.16 ± 0.96 | 0.88 ± 0.2 | 10.7 ± 0.7 |
| BNP7774 (ECSSM) | 0.04 ± 0.12 | 2.4 ± 0.7 | 37.0 ± 2.1 |
| BNP7776 (GCSSM) | 0.0 ± 0.7 | 4.1 ± 1.0 | 22.0 ± 0.5 |
| BNP7774S (ECSSCE) | 0.1 ± 0.05 | 2.1 ± 0.2 | 22.4 ± 1.7 |
| BNP7776S (GCSSCG) | 0.0 ± 0.5 | 1.6 ± 0.6 | 15.3 ± 0.4 |

[1]Rates are average of least two separate experiments in triplicate (n = 6).
[2]Two-way ANOVA analysis of the whole dataset shows that A, B, and C rates are significantly different among the disulfides tested (p-value = .001). One-way ANOVA analyses for each disulfide show that (1) oxidation rates in the presence of GRX (reaction C conditions) were significantly increased, and (2) Rates in reaction B conditions were significantly increased for all disulfides except GSSM and HSSM.
[3]Absorbance changes of less than .0005 were assigned as 0.0.
[4]BNPXXXX refer to BioNumerik Pharmaceuticals, Inc. proprietary compounds which all contain a disulfide moiety (SS).

IV. Summary of Tavocept™-Related Studies on the TX and GRX Systems

Various experimental data indicates that Tavocept™ (BNP7787, dimesna) and Tavocept™-derived mesna disulfide heteroconjugates formed as a consequence of thiol-disulfide exchange reactions may interact with the thioredoxin (TX) and glutaredoxin (GRX) systems in the following ways:

1) Tavocept™ drives the oxidation of reduced thioredoxin to oxidized thioredoxin;
2) BNP7787 derived metabolites (BNP7772, BNP7766, BNP7768, BNP7774 and BNP7776) are substrates (i.e., alternative substrate inhibitors) for the coupled thioredoxin/thioredoxin reductase/NADPH (see, FIG. 3, FIG. 5, and Table 1);

3) Tavocept™ inhibits the TX/TXR catalyzed reduction of the insulin A-B chain disulfide bond (and could inhibit reduction of other protein disulfides by TX/TXR interfering with signaling pathways);
4) Although Tavocept™ is not a substrate for glutathione reductase (the enzyme that reduces the disulfide form of glutaredoxin), the Tavocept™ metabolite BNP7772 (a Tavocept™-derived mesna-disulfide heteroconjugate) functions as an alternative substrate inhibitor and as such may compete with the GR catalyzed reduction of glutathione disulfide. This could inhibit glutaredoxin related signaling and cell proliferation pathways (see, FIG. 1, FIG. 2; and Table 4);
5) The Tavocept™ metabolite, mesna, in combination with cisplatin enhanced the reduction of α-lipoic acid (TX/TXR substrate) or hydroxyethyldisulfide (GRX substrate) by whole cells and intracellularly this mesna/cisplatin effect is predicted to result in a shift in equilibrium towards oxidized thioredoxin and glutaredoxin); and
6) Whole cell mediated disulfide reduction declined in response to treatments with paclitaxel, cisplatin and Tavocept™, and intracellularly this could be coupled with an altered redox balance favoring oxidized thioredoxin and oxidized glutaredoxin. This altered redox state would be expected to result in increased apoptotic sensitivity and decreased cell proliferation.

V. Summary of Tavocept™-Related Cytotoxicity Studies in Human Cancer Cell Lines 1) In non-small cell lung carcinoma (NSCLC) cell lines, mesna (100 μM) in combination with paclitaxel enhanced the cytotoxic effect of paclitaxel in comparison to paclitaxel alone controls;
2) In NSCLC and ovarian cancer cell lines, mesna (100 μM) in combination with oxaliplatin markedly enhanced the cytotoxic effect of oxaliplatin in comparison to oxaliplatin alone controls. In this same study, a lesser increase in oxaliplatin cytotoxicity was observed in brain cancer cells that were treated with oxaliplatin and mesna; this effect in brain cancer cells was observable but not statistically significant; and
3) In NSCLC and breast cancer cell lines, Tavocept™ in combination with cisplatin resulted in an increase in cell death in comparison to cisplatin only controls.

VI. Japan Phase III Clinical Trial

A. Summary of the Objectives and Methods of the Japan Phase III Clinical Trial

Data was recently unblinded from a multicenter, double-blind, randomized, placebo-controlled Phase III clinical trial of the Formula (I) compound Tavocept™ (also known as BNP7787, disodium 2,2'-dithio-bis-ethane sulfonate, and dimesna) conducted in Japan and involving patients with advanced non-small cell lung carcinoma (NSCLC), including the adenocarcinoma sub-type, who received the chemotherapeutic drugs paclitaxel and cisplatin (for purposes of this document referred to as the "Japan Phase III Clinical Trial").

The primary objective of the Japan Phase III Clinical Trial was to show that the Formula (I) compound, Tavocept™, prevents and/or reduces peripheral neuropathy induced by paclitaxel+cisplatin combination therapy in patients with non-small cell lung carcinoma (NSCLC), including the adenocarcinoma sub-type.

Patients admitted into the trial included those patients without previous treatment (excluding surgical treatment, administration of Picibanil into the serous membrane, irradiation of 30% or less hematopoietic bone, or oral chemotherapeutic agents within 3 months of entry in the trial).

The Japan Phase III Clinical Trial was conducted as a double-blind study because peripheral neuropathy is diagnosed based on subjective symptoms evaluated through clinical interviews, lab tests, and the like. Accordingly, evaluations by both physicians and patients are highly important. The present trial was designed to show that Tavocept™ prevents and/or reduces peripheral neuropathy induced by paclitaxel and cisplatin in NSCLC patients, including the adenocarcinoma sub-type. A placebo was used as control since there is no established therapy or drug for preventing peripheral neuropathy. Because the severity of peripheral neuropathy is evaluated based on patient's reports (i.e., subjective symptoms), the Peripheral Neuropathy Questionnaire (PNQ©) was used in primary evaluation. CIPN-20 and NCI-CTC were used in secondary evaluation. The incidence and severity of adverse reactions, time to their onset, etc. and the like, were compared between patients treated with Tavocept™ and those given a placebo using the aforementioned methods.

In order to conduct the present trial, Tavocept™ (approximately 14-22 g/m$^2$, most preferably approximately 18.4 g/m$^2$) or placebo (0.9% NaCl) was administered to NSCLC, including the adenocarcinoma sub-type, patients receiving chemotherapy with paclitaxel (approximately 160-190 mg/m$^2$, most preferably approximately 175 mg/m$^2$) and cisplatin (approximately 60-100, most preferably approximately 80 mg/m$^2$), every 3 weeks (and repeated for a minimum of 2 cycles).

B. Summary of the Results of the Japan Phase III Clinical Trial

The Japan Phase III Clinical Trial data demonstrated medically-important reductions in chemotherapy-induced peripheral neuropathy for patients receiving Tavocept™ and chemotherapy compared to patients receiving chemotherapy and a placebo. In addition, there were concurrent observations in the clinical trial population of medically-important reductions in chemotherapy-induced vomiting/emesis and kidney damage.

The aforementioned clinical trial also provided a number of unexpected physiological results which have, heretofore, been unreported in any previous scientific or clinical studies. Importantly, the Japan Phase III Clinical Trial demonstrated increased survival times for patients with advanced non-small cell lung cancer (NSCLC) receiving Tavocept™ and chemotherapy. A medically-important increase in survival time was also observed in patients with the NSCLC adenocarcinoma sub-type receiving Tavocept™ and chemotherapy. In addition, these unexpected and novel results included, but were not limited to, (i) the differentiation of chemotherapy-induced peripheral neuropathy into an entirely new class of peripheral neuropathy, called "intermittent" or "sporadic" peripheral neuropathy; (ii) potentiation of the cytotoxic or apoptotic activities of chemotherapeutic agents in patients with non-small cell lung carcinoma (NSCLC), including the adenocarcinoma sub-type, receiving Tavocept™ and chemotherapy; (iii) increasing patient survival and/or delaying tumor progression while maintaining or improving the quality of life in patients with non-small cell lung carcinoma (NSCLC), including the adenocarcinoma sub-type, receiving Tavocept™ and chemotherapy; and (iv) the maintenance or stimulation of hematological function (e.g., an increase in hemoglobin, hematocrit, and erythrocyte levels), in patients with non-small cell lung carcinoma (NSCLC), including the adenocarcinoma sub-type, receiving Tavocept™ and chemotherapy.

FIG. 5 illustrates, in tabular form, the Primary Endpoint (i.e., the mitigation or prevention of patient peripheral neuropathy) of the Japan Phase III Clinical Trial supporting the present invention as determined utilizing the Peripheral Neuropathy Questionnaire) (PNQ©). Results illustrated in FIG. 5 demonstrate that there was an approximate 50% reduction in severe (Grade D or E) peripheral neuropathy in the patient population with non-small cell lung carcinoma (NSCLC), including the adenocarcinoma sub-type, who were treated with a paclitaxel/Tavocept™/cisplatin regimen in comparison to those patients who received a paclitaxel/saline placebo/cisplatin regimen.

FIG. 6 illustrates, in tabular form, an evaluation of the statistical power observed in the Japan Phase III Clinical Trial with respect to the Primary Endpoint (i.e., the mitigation or prevention of patient peripheral neuropathy), as measured by the Generalized Estimating Equation (GEE) statistical method. The numerical value of 0.1565 in the tabular row designated "Drug" under the tabular column designated "P-Value" in FIG. 6, demonstrates that there is only a 15.65% probability that the reduction in peripheral neuropathy observed for Tavocept™ in the Japan Phase III Clinical Trial is due to random chance alone.

FIG. 7 illustrates, in tabular form, a Secondary Endpoint (i.e., a decrease in patient hemoglobin, erythrocyte, and hematocrit levels) of the Japan Phase III Clinical Trial supporting the present invention, in patients receiving Tavocept™ and chemotherapy. Results illustrated in FIG. 7 demonstrate that only 2, 1, and 1 non-small cell lung carcinoma (NSCLC), including the adenocarcinoma sub-type, patients in the Tavocept™ arm of the study exhibited a Grade 3 (severe) decrease in hemoglobin, red blood cell, and hematocrit levels, respectively, in comparison to 8, 5, and 5 patients in identical categories in the placebo arm of the Japan Phase III Clinical Trial.

FIG. 8 illustrates, in tabular form, a Secondary Endpoint (i.e., tumor response rate to chemotherapy administration) of the Japan Phase III Clinical Trial supporting the present invention, in patient populations receiving either Tavocept™ or placebo, as measured by the physician or by the Independent Radiological Committee (IRC) criteria. As is shown in the portion of the table designated "Doctor", the Response Rate, as measured by physicians, in the Tavocept™ arm of the Japan Phase III Clinical Trial was 41.9% compared to a 33.0% Response Rate in the placebo arm. As shown in the portion of the table designated "IRC", the response rate as measured by the IRC in the Tavocept™ arm of the Japan Phase III Clinical Trial was 33.3% as compared to a 28.6% response rate in the placebo arm.

Figure 9:
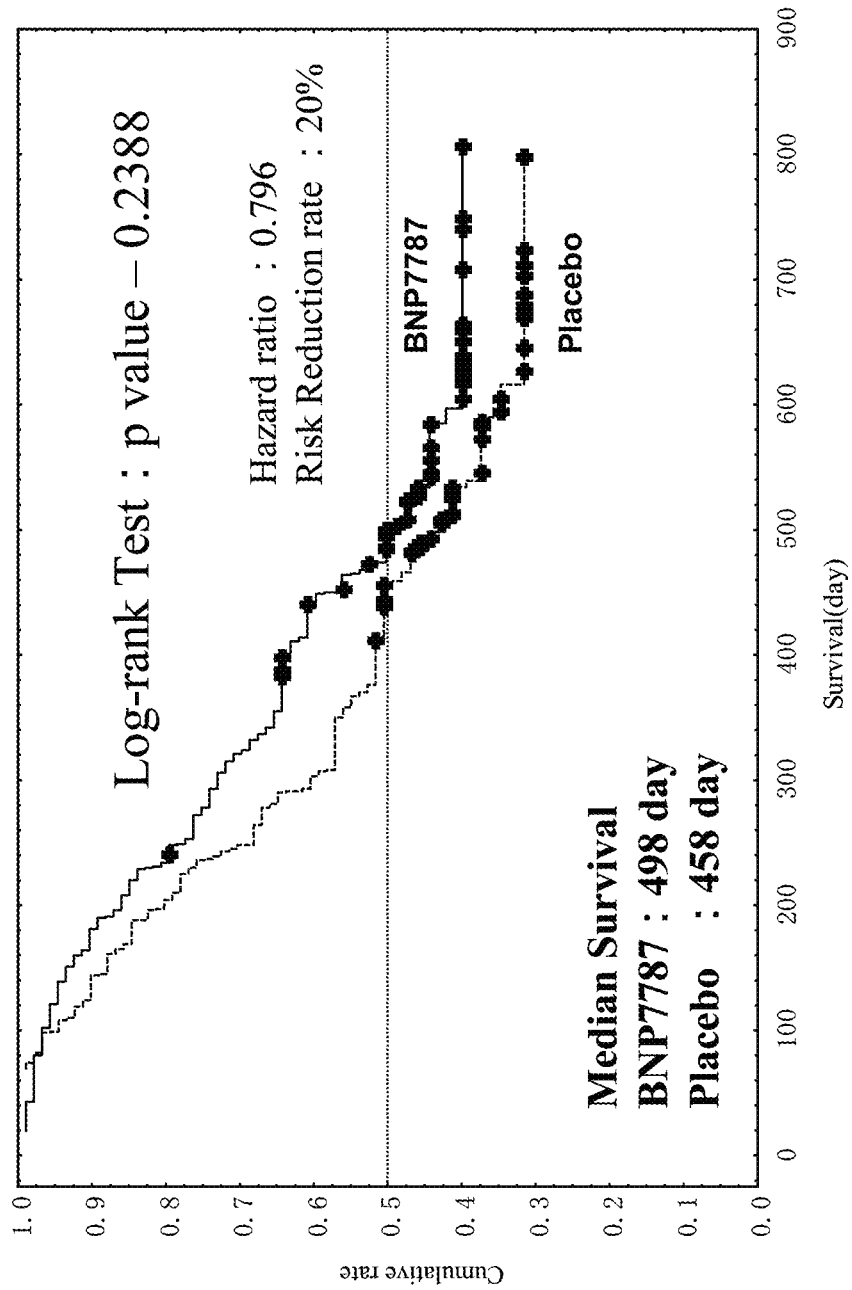
FIG. 9 illustrates, in graphical form, a Secondary Endpoint (i.e., patient survival) of the Japan Phase III Clinical Trial, in patient populations diagnosed with non-small cell lung carcinoma receiving either Tavocept™ (BNP7787) or placebo.

FIG. 9 illustrates, in graphical form, a Secondary Endpoint (i.e., patient survival) of the Japan Phase III Clinical Trial supporting the present invention, in patient populations receiving either Tavocept™ or placebo. Results illustrated in FIG. 9 demonstrate an increase in median survival time of up to 40 days in the portion of the patient population with non-small cell lung carcinoma (NSCLC), including the adenocarcinoma sub-type, who were treated with a paclitaxel/Tavocept™/cisplatin regimen in comparison to median survival time for those patients who received a paclitaxel/saline placebo/cisplatin regimen.

Figure 10:
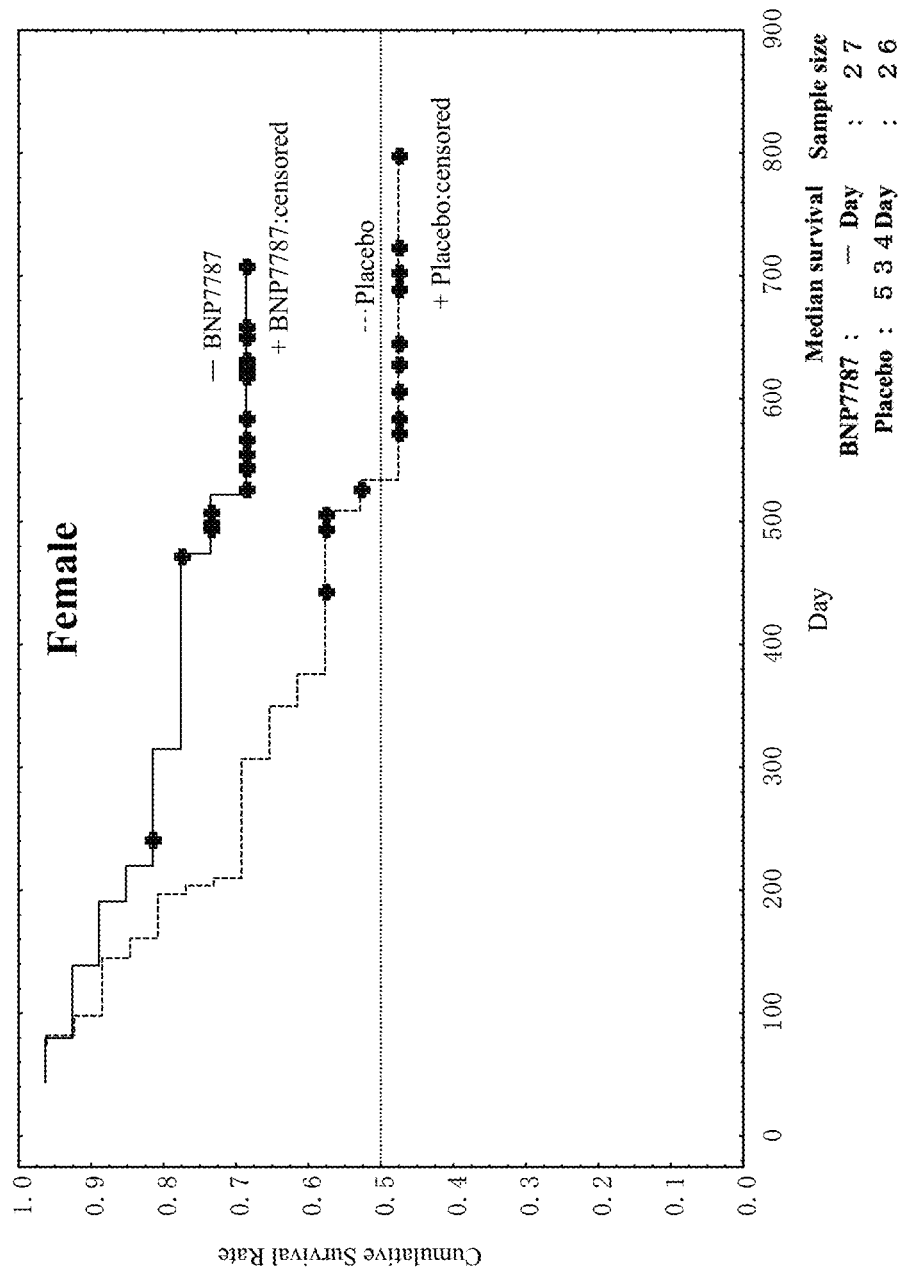
FIG. 10 illustrates, in graphical form, a Secondary Endpoint (i.e., patient survival) of the Japan Phase III Clinical Trial, in female patient populations receiving either Tavocept™ (BNP7787) or placebo.

FIG. 10 illustrates, in graphical form, a Secondary Endpoint (i.e., patient survival) of the Japan Phase III Clinical Trial supporting the present invention, in female patient populations receiving either Tavocept™ or placebo. Results in FIG. 10 demonstrate that the portion of the female patient population with non-small cell lung carcinoma (NSCLC), including the adenocarcinoma sub-type, who were treated with a paclitaxel/Tavocept™/cisplatin regimen had a longer survival period in comparison to the female patient population who received a paclitaxel/saline placebo/cisplatin regimen.

Figure 11:
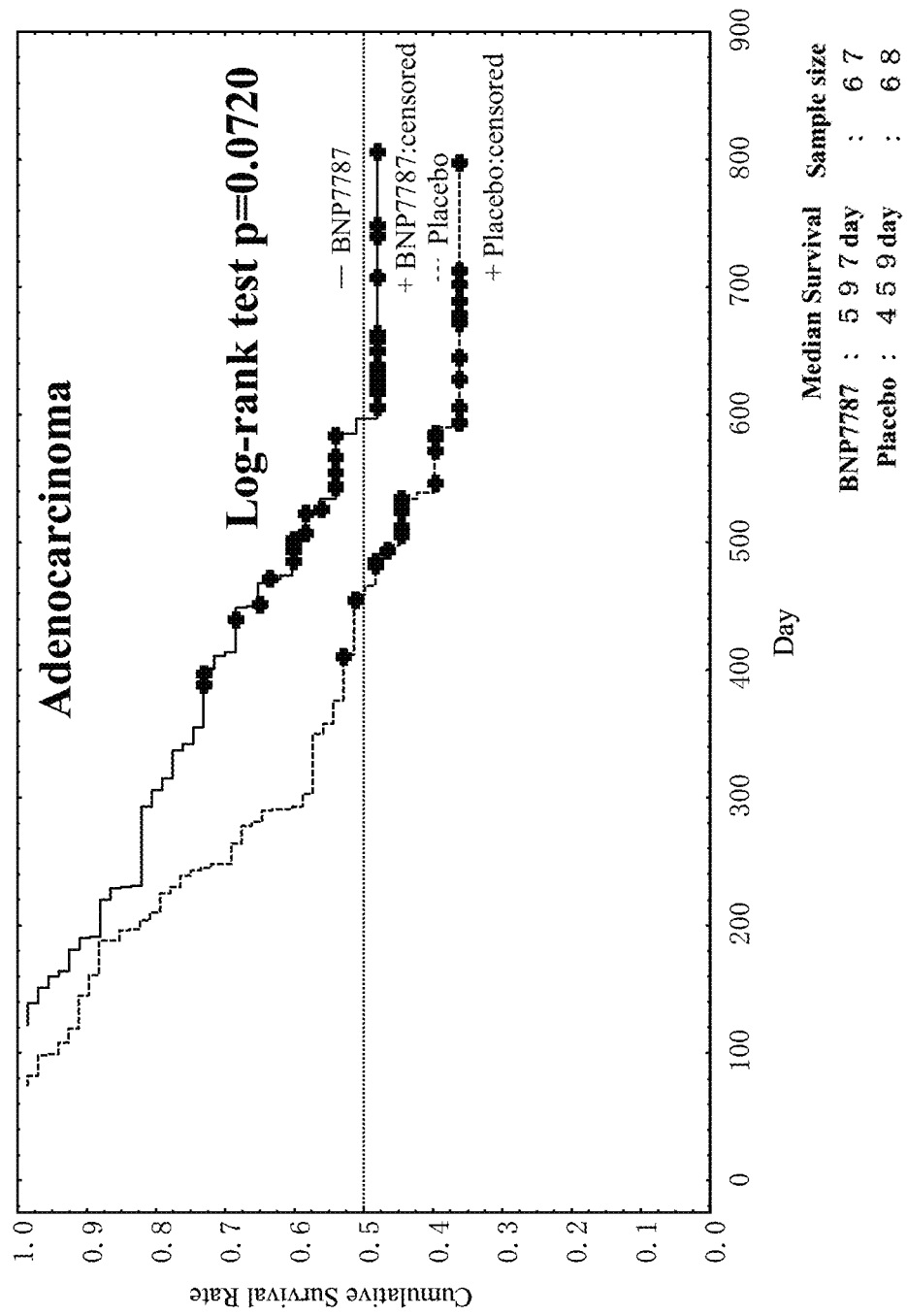
FIG. 11 illustrates, in graphical form, a Secondary Endpoint (i.e., patient survival) of the Japan Phase III Clinical Trial, in patient populations diagnosed with adenocarcinoma receiving either Tavocept™ (BNP7787) or placebo.

FIG. 11 illustrates, in graphical form, a Secondary Endpoint (i.e., patient survival) of the Japan Phase III Clinical Trial supporting the present invention, in patient populations diagnosed with the adenocarcinoma sub-type of non-small cell lung carcinoma (NSCLC) receiving either Tavocept™ or placebo. Results illustrated in FIG. 11 demonstrate an increase in median survival time of up to 138 days in the portion of the patient population with adenocarcinoma who were treated with a paclitaxel/Tavocept™/cisplatin regimen in comparison to the median survival time for those patients who received a paclitaxel/saline placebo/cisplatin regimen.

In addition, results from the Japan Phase III Clinical Trial also demonstrated reductions in: (i) fatigue (p=0.0163); (ii) nausea/vomiting (p=0.0240); (iii) anorexia (p=0.0029); (iv) diarrhea (p=0.0859); (v) constipation (p=0.1114); and (vi) insomnia (p=0.1108) in the portion of the patient population with non-small cell lung carcinoma (NSCLC) who were treated with a paclitaxel/Tavocept™/cisplatin regimen in comparison to those NSCLC patients who received a paclitaxel/saline placebo/cisplatin regimen.

The results from the Japan Phase III Clinical Trial described in the instant application represent medically important developments that support surprising new findings for Formula (I) compounds, including potential uses for: (i) increasing patient survival time in cancer patients receiving chemotherapy; (ii) causing cytotoxic or apoptotic potentiation of the anti-cancer activity of chemotherapeutic agents in cancer patients receiving chemotherapy; (iii) maintaining or stimulating hematological function in patients in need thereof, including cancer patients; (iv) maintaining or stimulating erythropoietin function or synthesis in patients in need thereof, including cancer patients; (v) mitigating or preventing anemia in patients in need thereof, including cancer patients; (vi) maintaining or stimulating pluripotent, multipotent, and unipotent normal stem cell function or synthesis in patients in need thereof, including cancer patients; (vii) promoting the arrest or retardation of tumor progression in those cancer patients receiving chemotherapy; and (viii) increasing patient survival and/or delaying tumor progression while maintaining or improving the quality of life in cancer patients receiving chemotherapy.

A. Summary of the Results of the U.S. Phase II NSCLC Clinical Trial

Data was recently unblinded from a United States (U.S.) multicenter Phase II clinical trial of the Formula (I) compound Tavocept™ (also known as BNP7787, disodium 2,2'-dithio-bis-ethane sulfonate, and dimesna) and involving patients with advanced, Stage IIIB/IV, non-small cell lung carcinoma (NSCLC), including the adenocarcinoma sub-type, who received the chemotherapeutic drugs docetaxel and cisplatin (for purposes of this document referred to as the "U.S. Phase II NSCLC Clinical Trial").

The U.S. Phase II NSCLC Clinical Trial disclosed in the present invention was used to ascertain the effect of a dose-dense administration of docetaxel and cisplatin every two weeks with concomitant administration of pegfilgrastim and darbepoetin alfa with and without administration of Tavocept™ (also referred to in the literature as disodium 2,2'-dithio-bis-ethane sulfonate, dimesna, or BNP7787) in patients with advanced stage (IIIB/IV) non-small cell lung carcinoma (NSCLC), including the adenocarcinoma sub-type. Whether or not Tavocept™ would affect the efficacy of the dose-dense docetaxel/cisplatin combination therapy was also evaluated based on the response rate, aggravation-free survival period, and total survival period. In order to make all these evaluations, in the Tavocept™ arm of the U.S. Phase II NSCLC Clinical Trial, docetaxel administration (75 mg/m$^2$; i.v. administration over a period of 1 hour on day one of the chemotherapy cycle) was immediately followed by the administration of Tavocept™ (approximately 40 grams; i.v. administration over a period of 30 minutes). The Tavocept™ administration was then immediately followed by the administration of cisplatin (75 mg/m$^2$; i.v. administration over a period of 1 hour) with adequate hydration. Darbepoetin alfa (200 μg; subcutaneous administration) was administered on day one of the chemotherapy cycle and pegfilgrastim (6 mg subcutaneous administration) was administered on day two of the chemotherapy cycle if the patient's hemoglobin levels were ≤11 g/dL. The aforementioned chemotherapy cycle was repeated every two weeks, for up to a total of six cycles. The other, non-Tavocept™ administration arm of the study was identical to the previously discussed Tavocept™ arm, with the exception that the docetaxel administration was immediately followed by cisplatin administration without an intermediate administration of Tavocept™. In addition, the incidence and severity of Grade 3 and Grade 4 adverse events were compared between patients in the Tavocept™ and non-Tavocept™ administration arms of the U.S. Phase II NSCLC Clinical Trial using the National Cancer Institute-Common Toxicity Criteria (NCI-CTC) questionnaire.

B. Summary of the Results of the U.S. Phase II NSCLC Clinical Trial

The U.S. Phase II NSCLC Clinical Trial data demonstrated medically-important reductions in the chemotherapy-induced side effects of dehydration, nausea, vomiting, and a dramatic reduction in hypomagnesaemia.

The aforementioned clinical trial also provided a number of unexpected physiological results which have, heretofore, been unreported in any previous scientific or clinical studies, with the exception of the Japan Phase III Clinical Trial. Similar to the results obtained in the Japan Phase III Clinical Trial, the U.S. Phase II NSCLC Clinical Trial demonstrated increased survival times for patients with advanced non-small cell lung cancer (NSCLC), including the adenocarcinoma sub-type, receiving Tavocept™ and chemotherapy. A marked increase in survival time was also observed in those patients with the adenocarcinoma non-small cell lung carcinoma (NSCLC) sub-type receiving Tavocept™ and chemotherapy. In addition, the unexpected and novel results for the Japan Phase III Clinical Trial and/or the U.S. Phase II NSCLC Clinical Trial included, but were not limited to: (i) potentiation of the cytotoxic or apoptotic activities of chemotherapeutic agents in patients with non-small cell lung carcinoma, including the adenocarcinoma sub-type, receiving Tavocept™ and chemotherapy and (ii) increasing patient survival and/or delaying tumor progression while concomitantly maintaining or improving the quality of life in patients with non-small cell lung carcinoma, including the adenocarcinoma sub-type, receiving Tavocept™ and chemotherapy due to a reduction in several chemotherapy-induced physiological side effects. It should be noted that in the U.S. Phase II NSCLC Clinical Trial, unlike the Japan Phase III Clinical Trial, the maintenance or stimulation of hematological function (e.g., an increase in hemoglobin, hematocrit, and erythrocyte levels), in patients with non-small cell lung carcinoma, including adenocarcinoma, receiving Tavocept™ and chemotherapy was not measured due to the fact that patients with hemoglobin levels ≤11 g/dL, received darbepoetin alfa (200 μg) and pegfilgrastim (6 mg) on day 1 and day 2 of the patient's chemotherapy cycle, respectively.

Figure 12:
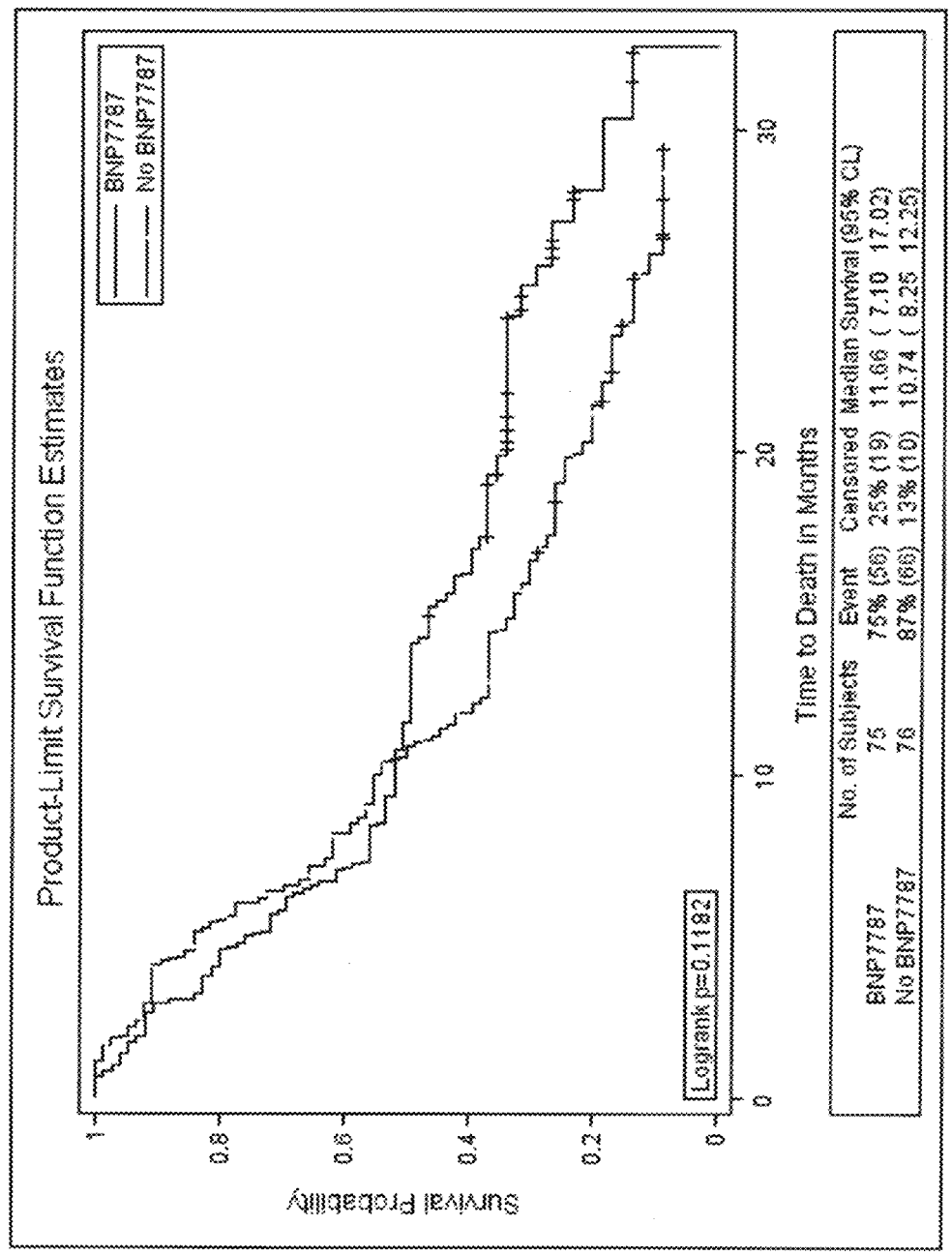
FIG. 12 illustrates, in graphical form, the median patient survival (i.e., time to death in months) in the U.S. Phase II NSCLC Clinical Trial, in patient populations diagnosed with non-small cell lung carcinoma receiving chemotherapy with either Tavocept™ (BNP7787) or no Tavocept™ treatment.

FIG. 12 illustrates, in graphical form, the median patient survival (i.e., time to death in months) in the U.S. Phase II NSCLC Clinical Trial, in patient populations diagnosed with non-small cell lung carcinoma, including the adenocarcinoma sub-type, receiving chemotherapy with either Tavocept™ (BNP7787) or no Tavocept™ treatment. The results indicate a 0.92 month increase in patient survival in the Tavocept™ arm of the study (11.66 months) versus the non-Tavocept™ arm (10.74 months) measured with a 95% confidence limit. The hazard ratio was 0.750.

FIG. 13 illustrates, in tabular form, patient overall survival (OS) and patient progression-free survival (PFS) in the U.S. Phase II NSCLC Clinical Trial, in patient populations diagnosed with non-small cell lung carcinoma, including the adenocarcinoma sub-type, receiving chemotherapy with either Tavocept™ (BNP7787) or no Tavocept™ treatment. The results indicate a 9.5% increase in patient progression-free survival (PFS) in the Tavocept™ arm of the study (18.7%) versus the non-Tavocept™ arm (9.25%) and an 11.2% increase in overall patient one-year survival (OS) rates in the Tavocept™ arm (50.7%) verses the non-Tavocept™ arm (39.5%), both values measured with a 95% confidence interval.

Figure 14:
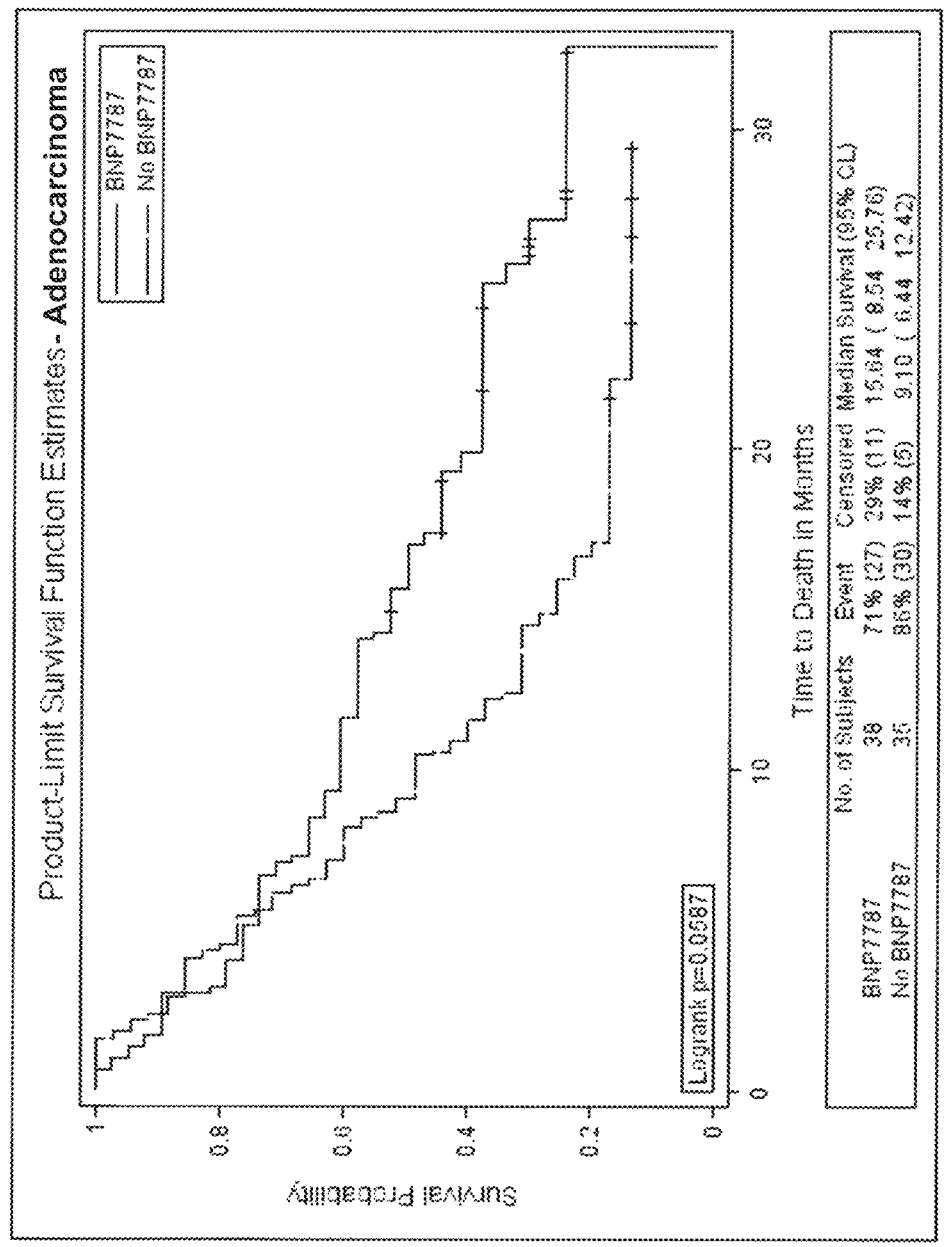
FIG. 14 illustrates, in graphical form, the median patient survival (i.e., time to death in months) in the U.S. Phase II NSCLC Phase II Clinical Trial, in patient populations diagnosed with adenocarcinoma receiving chemotherapy with either Tavocept™ (BNP7787) or no Tavocept™ treatment.

FIG. 14 illustrates, in graphical form, the median patient survival (i.e., time to death in months) in the U.S. Phase II NSCLC Phase II Clinical Trial, in patient populations diagnosed with adenocarcinoma receiving chemotherapy with either Tavocept™ (BNP7787) or no Tavocept™ treatment. The results indicate a 6.54 month increase in patient survival in the Tavocept™ arm of the study (15.64 months) versus the non-Tavocept™ arm (9.10 months). This value was measured with a 95% confidence limit. This represents a 40% reduction in the patient mortality rate. In addition, it should be noted that there were over double the number of patients in the Tavocept™ arm of the study (11 patients) verses the non-Tavocept™ arm (5 patients). The hazard ratio was 0.601.

FIG. 15 illustrates, in tabular form, the number of patients experiencing Grade 3 and Grade 4 treatment-related adverse events in the U.S. Phase II NSCLC Phase II Clinical Trial, in patient populations diagnosed with non-small cell lung carcinoma, including the adenocarcinoma sub-type, receiving chemotherapy with either Tavocept™ (BNP7787) or no Tavocept™ treatment. The results indicate a 50% reduction in dehydration, a 38.5% reduction in nausea, a 71.5% reduction in vomiting, and a 100% reduction in hypomagnesaemia in the patients in the Tavocept™ arm of the study versus the non-Tavocept™ arm.

In summation, the Applicant believes the experimental and clinical data obtained from the Japan Phase III Clinical Trial and the U.S. Phase II NSCLC Clinical Trial, discussed above, supports the ability of Tavocept™ to cause a marked increase in the survival time of patients with non-small cell lung carcinoma (NSCLC), and especially in patients with the adenocarcinoma NSCLC sub-type. It is important to note that the patient populations in the U.S. Phase II NSCLC Clinical Trial and Japan Phase III Clinical Trial taken together represent a diverse sampling of patients having different ethnicities. Additional experimental and clinical evaluation will lend continued support for the ability of Tavocept™ to increase the survival time of patients with cancer, wherein the cancer either: (i) overexpresses thioredoxin or glutaredoxin and/or (ii) exhibits evidence of thioredoxin-mediated or glutaredoxin-mediated resistance to the chemotherapeutic agent or agents used to treat said patient with cancer.

All patents, publications, scientific articles, web sites, and the like, as well as other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicant reserves the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicant reserves the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in the written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y". The letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicant reserves the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A method for treatment of a subject suffering from cancer who has previously received administration of one or more chemotherapeutic agents;
    wherein (i) said cancer either overexpresses thioredoxin or glutaredoxin and/or exhibits evidence of thioredoxin-mediated or glutaredoxin-mediated resistance to the chemotherapy agent or agents used to treat said patient with cancer; (ii) said thioredoxin or glutaredoxin overexpression and/or said thioredoxin-mediated or glutaredoxin-mediated treatment resistance is quantitatively determined by use of an analytical methodology selected from the group consisting of fluorescence in situ hybridization (FISH), nucleic acid microarray analysis, immunohistochemistry (IHC), and radioimmunoassay (RIA); and (iii) if the prior chemotherapeutic agents received by said subject included taxane and platinum agents, the administration of the taxane-containing chemotherapy agent occurred prior to the administration of the platinum-containing chemotherapy agent; and wherein said method for treatment comprises the administration of a medically-sufficient dose of disodium 2,2'-dithio-bis-ethane sulfonate to said subject with cancer in an amount sufficient to provide a therapeutic benefit following the time said subject has previously received administration of chemotherapeutic agents.

2. A method for maintaining or stimulating pluripotent, multipotent, and unipotent normal stem cell function in a patient suffering from cancer who has previously received administration of one or more chemotherapeutic agents, wherein said method is comprised of the administration of a medically-sufficient dose of disodium 2,2'-dithio-bis-ethane sulfonate to said patient, and (i) the cancer is selected from the group consisting of gastric cancer, esophageal cancer, cancer of the biliary tract, endometrial cancer, and hepatic cancer, (ii) said cancer overexpresses thioredoxin or glutaredoxin; (iii) said thioredoxin or glutaredoxin overexpression is quantitatively determined by use of an analytical methodology selected from the group consisting of fluorescence in situ hybridization (FISH), nucleic acid microarray analysis, immunohistochemistry (IHC), and radioimmunoassay (RIA); and (iv) if the prior chemotherapeutic agents received by said patient included taxane and platinum agents, the administration of the taxane-containing chemotherapy agent occurred prior to the administration of the platinum-containing chemotherapy agent.

3. The method of claim 2, wherein said platinum chemotherapy agent or agents are selected from the group consisting of: cisplatin, carboplatin, oxaliplatin, satraplatin, picoplatin, tetraplatin, platinum-DACH, and analogs and derivatives thereof.

4. The method of claim 2, wherein said taxane chemotherapy agent or agents are selected from the group consisting of: docetaxel, paclitaxel, polyglutamylated forms of paclitaxel, liposomal paclitaxel, and analogs and derivatives thereof.

5. The method of claim 1 or claim 2, wherein the taxane and/or platinum-containing chemotherapy agents are paclitaxel and/or cisplatin.

6. A method for maintaining or stimulating erythropoietin function or synthesis in a subject suffering from cancer who has previously received administration of one or more chemotherapeutic agents, wherein said method is comprised of the administration of a medically-sufficient dose of disodium 2,2'-dithio-bis-ethane sulfonate to said subject, and (i) the cancer is selected from the group consisting of gastric cancer, esophageal cancer, cancer of the biliary tract, endometrial cancer, and hepatic cancer, (ii) said cancer overexpresses thioredoxin or glutaredoxin; (iii) said thioredoxin or glutaredoxin overexpression is quantitatively determined by use of an analytical methodology selected from the group consisting of fluorescence in situ hybridization (FISH), nucleic acid microarray analysis, immunohistochemistry (IHC), and radioimmunoassay (RIA); and (iv) if the prior chemotherapeutic agents received by said subject included taxane and platinum agents, the administration of the taxane-containing chemotherapy agent occurred prior to the administration of the platinum-containing chemotherapy agent.

7. The method of claim 1, wherein the cancer is selected from the group consisting of gastric cancer, esophageal cancer, cancer of the biliary tract, endometrial cancer, and hepatic cancer.

8. A method for treatment of a subject suffering from cancer after said subject has previously received administration of one or more chemotherapeutic agents; wherein (i) the cancer is selected from the group consisting of gastric cancer, esophageal cancer, cancer of the biliary tract, endometrial cancer, and hepatic cancer, (ii) said cancer either overexpresses thioredoxin or glutaredoxin; (iii) said thioredoxin or glutaredoxin overexpression is quantitatively determined by use of an analytical methodology selected from the group consisting of fluorescence in situ hybridization (FISH), nucleic acid microarray analysis, immunohistochemistry (IHC), and radioimmunoassay (RIA); and (iv) if the prior chemotherapeutic agents received by said subject included taxane and platinum agents, the administration of the taxane-containing chemotherapy agent occurred prior to the administration of the platinum-containing chemotherapy agent;

and wherein said method for treatment comprises the administration of disodium 2,2'-dithio-bis-ethane sulfonate to said subject in an amount sufficient to provide a therapeutic benefit following the time said subject has previously received administration of chemotherapeutic agents.

* * * * *